United States Patent
Goguen et al.

(10) Patent No.: US 8,716,283 B2
(45) Date of Patent: May 6, 2014

(54) TYPE III SECRETION INHIBITORS, ANALOGS AND USES THEREOF

(75) Inventors: Jon Goguen, Holden, MA (US); Ning Pan, Boylston, MA (US); Kyungae Lee, Newton, MA (US)

(73) Assignees: University of Massachusetts, Boston, MA (US); President and Fellows of Harvard College, Cambridge, MA (US)

( * ) Notice: Subject to any disclaimer, the term of this patent is extended or adjusted under 35 U.S.C. 154(b) by 152 days.

(21) Appl. No.: 12/742,043

(22) PCT Filed: Apr. 1, 2009

(86) PCT No.: PCT/US2009/002022
§ 371 (c)(1), (2), (4) Date: Oct. 14, 2010

(87) PCT Pub. No.: WO2009/145829
PCT Pub. Date: Dec. 3, 2009

(65) Prior Publication Data
US 2011/0034463 A1    Feb. 10, 2011

Related U.S. Application Data

(63) Continuation-in-part of application No. PCT/US2008/012610, filed on Nov. 7, 2008.

(60) Provisional application No. 61/072,712, filed on Apr. 1, 2008, provisional application No. 61/002,316, filed on Nov. 7, 2007.

(51) Int. Cl.
*A61K 31/44* (2006.01)
*C07D 213/84* (2006.01)

(52) U.S. Cl.
USPC .............. 514/235.5; 514/253.12; 514/318; 514/350; 514/353; 514/367; 546/193; 546/298; 546/306

(58) Field of Classification Search
USPC ......... 514/235.5, 253.12, 318, 350, 353, 367; 546/193, 298, 306
See application file for complete search history.

(56) References Cited

U.S. PATENT DOCUMENTS

| | | |
|---|---|---|
| 6,136,542 A | 10/2000 | Demers et al. |
| 6,586,200 B2 | 7/2003 | Omura et al. |

(Continued)

FOREIGN PATENT DOCUMENTS

| | | |
|---|---|---|
| EP | 0 387 070 A2 | 9/1990 |
| WO | WO-99/58714 A2 | 11/1999 |

(Continued)

OTHER PUBLICATIONS

2nd paragraph supplemental guideline, p. 1, 64-67 (2011).*

(Continued)

*Primary Examiner* — Celia Chang
(74) *Attorney, Agent, or Firm* — Wolf, Greenfield & Sacks, P.C.

(57) ABSTRACT

The invention, in some aspects, relates to compounds and compositions useful for inhibiting Type III secretion systems in pathogenic bacteria, such as *Yersinia Pestis*. In some aspects, the invention relates to methods for discovering inhibitors of the Type III secretion system and uses of such inhibitors in the treatment and prevention of disease.

11 Claims, 28 Drawing Sheets

(56) References Cited

U.S. PATENT DOCUMENTS

| | | |
|---|---|---|
| 7,232,569 B2 | 6/2007 | Frey et al. |
| 2004/0106553 A1 | 6/2004 | Alekshun et al. |
| 2006/0134724 A1 | 6/2006 | Kauppi et al. |

FOREIGN PATENT DOCUMENTS

| | | | |
|---|---|---|---|
| WO | WO-00/78726 A1 | 12/2000 | |
| WO | WO-2006/076009 A2 | 7/2006 | |
| WO | WO-2007/131622 A1 | 11/2007 | |
| WO | WO2009061491 | * | 5/2009 |

OTHER PUBLICATIONS

Casadevall et al. "Virulence factors . . . " H. water and health vol. 7S1, p. S2-S18 (2009).*

Ferracci et al. "Selectiion and characterization . . . " Mol. Microbi. 57(4) p. 970-987 (2005).*

Isomorphism Wikipedia p. 1 (2012).*

Kueyh et al "Bacterial outer . . . " Genes Dev. v.19 p. 2645-2655 (2005).*

Nordfelth et al. "Small molecule . . . " Infection and Immunity v.73(5) p. 3104-3114 (2005).*

Ompndi et al. "Polymorphism and phase . . . " Crys. Eng. Comm. Roy. Soc. Chem. vol. 7, p. 690-700 (2005).*

Wierenga et al. "High throughput . . . " J. bop,p;. Screen 13:415-423 (2008).*

PCT/US2008/012610, Aug. 10, 2009, Invitation to Pay Additional Fees.

PCT/US2008/012610, Oct. 30, 2009, International Search Report and Written Opinion.

PCT/US2008/012610, May 20, 2010, International Preliminary Report on Patentability.

PCT/US2009/002022, Oct. 21, 2009, International Search Report and Written Opinion.

PCT/US2009/002022, Oct. 14, 2010, International Preliminary Report on Patentability.

Abe et al., Type-III effectors: sophisticated bacterial virulence factors. C R Biol. May 2005;328(5):413-28.

Adams et al., The chemotherapeutic efficacy of imidocarb dihydrochloride on concurrent bovine anaplasmosis and babesiosis. II. The effects of multiple treatments. Trop Anim Health Prod. May 1974;6(2):79-84.

Bailey et al., Small molecule inhibitors of type III secretion in Yersinia block the Chlamydia pneumoniae infection cycle. FEBS Lett. Feb. 20, 2007;581(4):587-95. Epub Jan. 17, 2007.

Ben-Gurion et al., Essential virulence determinants of different Yersinia species are carried on a common plasmid. Plasmid. Mar. 1981;5(2):183-7.

Boland et al., Status of YopM and YopN in the Yersinia Yop virulon: YopM of Y. enterocolitica is internalized inside the cytosol of PU5-1.8 macrophages by the YopB, D, N delivery apparatus. EMBO J. Oct. 1, 1996;15(19):5191-201.

Cornelis, The Yersinia Ysc-Yop 'type III' weaponry. Nat Rev Mol Cell Biol. Oct. 2002;3(10):742-52.

Deng et al., Regulation of type III secretion hierarchy of translocators and effectors in attaching and effacing bacterial pathogens. Infect Immun. Apr. 2005;73(4):2135-46.

Ferber et al., Plasmids in Yersinia pestis. Infect Immun. Feb. 1981;31(2):839-41.

Gauthier et al., Transcriptional inhibitor of virulence factors in enteropathogenic Escherichia coli. Antimicrob Agents Chemother. Oct. 2005;49(10):4101-9.

Håkansson et al., The YopB protein of Yersinia pseudotuberculosis is essential for the translocation of Yop effector proteins across the target cell plasma membrane and displays a contact-dependent membrane disrupting activity. EMBO J. Nov. 1, 1996;15(21):5812-23.

Higuchi et al., Studies on the nutrition and physiology of Pasteurella pestis. III. Effects of calcium ions on the growth of virulent and avirulent strains of Pasteurella pestis. J Bacteriol. Mar. 1959;77(3):317-21.

Hung, Chemotherapeutic efficacy of imidocarb dipropionate on experimental Eperythrozoon ovis infection in sheep. Trop Anim Health Prod. May 1986;18(2):97-102.

Jones et al., In vitro evaluation of CENTA, a new beta-lactamase-susceptible chromogenic cephalosporin reagent. J Clin Microbiol. May 1982;15(5):954-8.

Kauppi et al., Targeting bacterial virulence: inhibitors of type III secretion in Yersinia. Chem Biol. Mar. 2003;10(3):241-9.

Keyser et al., Virulence blockers as alternatives to antibiotics: type III secretion inhibitors against Gram-negative bacteria. J Intern Med. Jul. 2008;264(1):17-29. doi: 10.1111/j.1365-2796.2008.01941.x. Epub Apr. 3, 2008.

Linington et al., Caminoside A, an antimicrobial glycolipid isolated from the marine sponge Caminus sphaeroconia. Org Lett. Nov. 14, 2002;4(23):4089-92.

Marketon et al., Plague bacteria target immune cells during infection. Science. Sep. 9, 2005;309(5741):1739-41. Epub Jul. 28, 2005.

Mueller et al., The V-antigen of Yersinia forms a distinct structure at the tip of injectisome needles. Science. Oct. 28, 2005;310(5748):674-6.

Muschiol et al., A small-molecule inhibitor of type III secretion inhibits different stages of the infectious cycle of Chlamydia trachomatis. Proc Natl Acad Sci U S A. Sep. 26, 2006;103(39):14566-71. Epub Sep. 14, 2006.

Nordfelth et al., Small-molecule inhibitors specifically targeting type III secretion. Infect Immun. May 2005;73(5):3104-14.

Rosqvist et al., Intracellular targeting of the Yersinia YopE cytotoxin in mammalian cells induces actin microfilament disruption. Infect Immun. Dec. 1991;59(12):4562-9.

Rosqvist et al., Target cell contact triggers expression and polarized transfer of Yersinia YopE cytotoxin into mammalian cells. EMBO J. Feb. 15, 1994;13(4):964-72.

Wiley et al., Induction of the Yersinia type 3 secretion system as an all-or-none phenomenon. J Mol Biol. Oct. 12, 2007;373(1):27-37. Epub Aug. 17, 2007.

Wolf et al., Treatment of Chlamydia trachomatis with a small molecule inhibitor of the Yersinia type III secretion system disrupts progression of the chlamydial developmental cycle. Mol Microbiol. 2006;61(6):1543-55.

Zhang et al., A simple statistical parameter for use in evaluation and validation of high throughput screening assays. J Biomol Screen. Apr. 1999;4(2):67-73.

* cited by examiner

Analogs - ELISA Assay of YopH Secretions

1.2

1.3

2.1
2.2

4.1

4.2

70,966 Compounds/Extracts Were Screened in Duplicates

| Library Name | Plates | Compound |
|---|---|---|
| Biomol-TimTec1 | 25 | 8,518 |
| ChemDiv1 | 49 | 17,248 |
| ChemDiv2 | 25 | 8,560 |
| ChemDiv3 | 47 | 16,544 |
| Enamine1 | 18 | 6,004 |
| IF Lab 1 | 19 | 6,543 |
| Maybridge4 | 13 | 4,576 |
| mix Commercial 5 | 1 | 268 |
| Peakdale 2 | 1 | 352 |
| Phillipines plant extracts 1 | 1 | 200 |
| Phillipines plant extracts 2 | 2 | 648 |
| Star Foundation Extracts 1 | 3 | 1,025 |
| BIOMOL ICCB Known Bioactives | 2 | 480 |
| 12 | 206 | 70,966 |

Fig. 17C

TYPE III SECRETION INHIBITORS, ANALOGS AND USES THEREOF

RELATED APPLICATIONS

This application is a national stage filing under 35 U.S.C. §371 of international application PCT/US2009/002022, filed Apr. 1, 2009, which was published under PCT Article 21(2) in English, which claims the benefit under 35 U.S.C. §119(e) of the filing date of U.S. Provisional Application U.S. Ser. No. 61/072,712 filed Apr. 1, 2008, and which is a continuation-in-part of international application PCT/US2008/012610, filed Nov. 7, 2008, which was published under PCT Article 21(2) in English, which claims the benefit under 35 U.S.C. §119(e) of the filing date of U.S. Provisional Application U.S. Ser. No. 61/002,316 filed Nov. 7, 2007. The entire teachings of the referenced applications are expressly incorporated herein by reference.

GOVERNMENT FUNDING

This invention was made with Government support from the National Institutes of Health under Grant No. U54 AI1057159. The Government has certain rights in the invention.

BACKGROUND OF INVENTION

1. Field of Invention

The invention relates to methods for discovering inhibitors of the Type III secretion system and uses of such inhibitors in the treatment and prevention of disease.

2. Discussion of Related Art

A broad clinical spectrum of disease is associated with infection by pathogenic gram-negative bacteria. A variety of pathogenic gram-negative bacteria, such as *Yersinia pestis*, *Y. pseudotuberculosis* and *Y. enterocolitica*, utilize a plasmid-encoded type III secretion system (T3SS) to promote infection by delivering pathogenic proteins into the cytosol of host target cells. The injected proteins interfere with host cell signaling pathways and other cellular processes, thereby allowing the organism to avoid the host immune system and establish systemic infections. This T3SS is absolutely required for virulence of these pathogenic organisms. Thus, the T3SS is an attractive target for the development of novel therapeutics for treatment and prevention of disease brought on by infection by such pathogens. While the need for such therapeutics is well recognized, this need remains to be fulfilled in a clinically significant way.

SUMMARY OF INVENTION

*Yersinia pestis* and other pathogenic Yersinae, *Y. pseudotuberculosis* and *Y. enterocolitica*, utilize a plasmid encoded type III secretion system (T3SS) to promote infection by injecting a battery of effector proteins known as Yops (*Yersinia* outer proteins) into the cytosol of host cells that come into contact with the bacteria during infection. Type III secretion (T3S) is absolutely required for *Yersinia* virulence, which makes T3SS an attractive target in the development of new therapeutics. A novel high throughput screening (HTS) method is developed and used to screen a diverse collection of compound libraries to find small molecules that inhibit type III secretion in *Y. pestis*. The initial HTS of 70,966 compounds and mixtures from a diverse collection of libraries resulted 431 primary hits. Eight compounds were selected from among the strong and moderate hits for further analysis in secondary assays. Four of the eight compounds effectively inhibited Yop secretion at micromolar concentrations. With some compounds, differential inhibition among Yop species was observed. The compounds did not inhibit bacterial growth at the concentrations used in the inhibition assays. Three compounds protected HeLa cells from type III secretion-dependent cytotoxicity. Of the eight compounds examined in secondary assays, four show good promise as leads for structure-activity relationship (SAR) studies. They are a diverse group, each having chemical scaffold not only distinct from each other, but also distinct from previous described candidate type III inhibitors. The type III secretion (T3S) inhibitors are useful for the treatment and prevention of disease caused by gram-negative bacterial pathogens comprising the T3S system. In some aspects, the invention relates to the discovery of analogs of certain T3S inhibitor compounds that were identified using the screening methods disclosed herein.

According to some aspects, methods for decreasing virulence of a bacterium are provided. In some embodiments, the methods involve contacting a bacterium with at least one compound (e.g., 1, 2, 3, 4, 5, or more different compounds) that inhibits a type III secretion system.

In some embodiments of the methods disclosed herein, the bacterium is a *Yersinia* species.

In some embodiments of the methods disclosed herein, the *Yersinia* species is *Yersinia pestis*, *Yersinia pseudotuberculosis*, or *Yersinia enterocolitica*.

In some embodiments of the methods disclosed herein, the bacterium is selected from the group consisting of: *Yersinia pestis*, *Yersinia enterocolitica*, *Yersinia pseudotuberculosis*, *Salmonella enterica*, *Escherichia coli*, *Shigella dysenteriae*, *Shigella flexneri*, *Shigella boydii*, *Shigella sonnei*, *Bordetella pertussis*, *Bordetella parapertussis*, *Bordetella bronchiseptica*, *Pseudomonas aeruginosa*, *Burkholderia pseudomallei*, *Vibrio parahaemolyticus*, *Vibrio cholerae*, *Chlamydia trachomatis*, *Chlamydia pneumoniae*, and *Chlamydia psittaci*.

In some embodiments of the methods disclosed herein, the bacterium is in a subject.

In some embodiments of the methods disclosed herein, the subject has a disease, or is at risk of a disease, caused by the bacterium.

In some embodiments of the methods disclosed herein, the disease is selected from the group consisting of: bubonic plague, pneumonic plague, septicemic plague, enterocolitis, mesenteric lymphadenitis, typhlitis, typhoid-like disease, enteric fever, intestinal inflammation, bacteremia, septicemia, bloody diarrhea, renal failure, septic shock, bacillary dysentery (shigellosis), sporadic dysentery, whooping cough, kennel cough, atrophic rhinitis, respiratory illness, pneumonia, chronic airway infection, urinary tract infection, clinical infections, melioidosis, noninflammatory secretory diarrhea, inflammatory diarrhea, sexually transmitted infection, and psittacosis.

In some embodiments of the methods disclosed herein, the subject is a human.

In some embodiments of the methods disclosed herein, the bacterium is a biowarfare agent.

According to some aspects, methods for treating a subject that has a disease, or is at risk of having a disease, caused by a bacterium that has a type III secretion system are provided. In some embodiments, the methods involve administering to the subject a therapeutically effective amount of a pharmaceutical composition comprising at least one compound that inhibits a type III secretion system.

In some embodiments of the methods disclosed herein, the at least one compound that inhibits a type III secretion system is selected from the group consisting of:

(a) a compound of the formula:

or a pharmaceutically acceptable salt thereof,
wherein:
R1 is selected from the group consisting of:
—O—(C1-C5)alkyl,
—NH—(C1-C5)alkyl,
—NH$_2$, and
—OH, and R2 is wherein:
R3 and R4 are joined as a five- or six-member heterocyclic ring that may be further substituted at any one position with —CO—O—(C1-C5)alkyl or (C1-C5)alkyl, or
R3 is —H or —(C1-C5)alkyl and
R4 is selected from the group consisting of:
—(C1-C5)alkyl,
—(C3-C8)cycloalkyl,
—(C1-C5)alkyl-O—(C1-C5)alkyl,
—(C1-C5)alkyl-hydroxyl,
-phenyl, and
—(C1-C5)alkyl-phenyl,
wherein the phenyl group may be independently substituted at one, two, or three positions with —(C1-C5)alkyl or -halogen, and
R5 is selected from the group consisting of:
—(C1-C5)alkyl,
—(C3-C8)cycloalkyl,
-phenyl, and
—(C1-C5)alkyl-phenyl,
wherein the phenyl group may be substituted at one, two, or three positions with a substituent independently selected from the group consisting of:
—(C1-C5)alkyl,
—O—(C1-C5)alkyl,
-halogen,
—NO$_2$,
—CF$_3$, and
—OCF$_3$;

(b) a compound of the formula:

or a pharmaceutically acceptable salt thereof,
wherein:
each of $X^1$ and $X^3$ is a —(C1-C5)alkyl or —NH$_2$,
$X^2$ is —O—, —SO$_2$—, or —S—, and
n and m are integers between 0 and 4;

(c) a compound of the formula:

or a pharmaceutically acceptable salt thereof,
wherein:
R6 is selected from the group consisting of:

wherein i is an integer from 0 to 2, and wherein each $X^5$ is independently selected from the group consisting of:
—(C1-C6)alkyl,
—O—(C$_1$-C$_6$)alkyl,
—CO—(C1-C6)alkyl,
—CO—O—(C1-C6)alkyl,
—NO$_2$, —CN,
-halogen,
—CF₃,

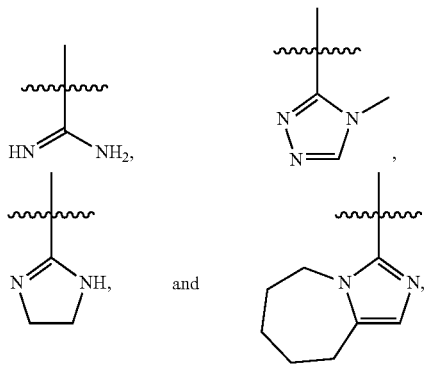

R7 is =O or =S,
R8 is selected from the group consisting of:
  -hydrogen,
  —CF₃,

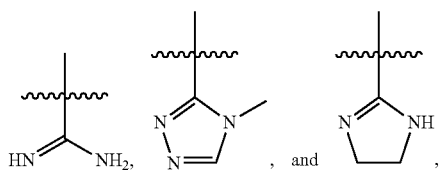

X⁴ is -halogen, and
p is 0 or 1;
(d) a compound of the formula:

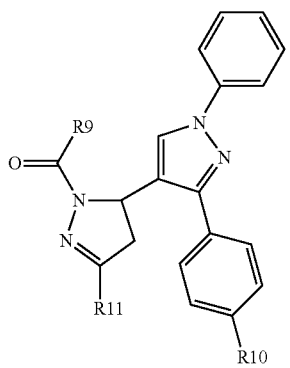

or a pharmaceutically acceptable salt thereof,
  wherein:
  R9 is selected from the group consisting of:
    —(C1-C5)alkyl,
    —(C1-C5)alkyl-CO₂H, and

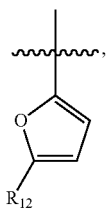

wherein R12 is -halogen,
R10 is selected from the group consisting of:
  -hydrogen,
  —(C1-C6)alkyl, and
  —O—(C1-C6)alkyl;
R11 is selected from the group consisting of:

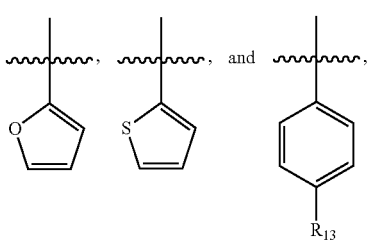

wherein R13 is -hydrogen or —(C1-C6)alkyl; and
(e) a compound of the formula:

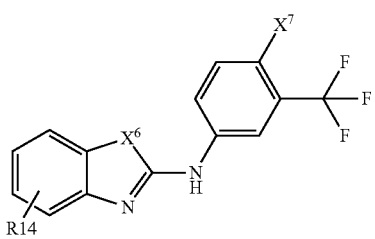

or a pharmaceutically acceptable salt thereof,
  wherein:
  R14 is

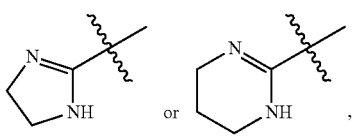 [SMILES: *C1=NCCN1 ; *C1=NCCCN1]

X⁶ is —O— or —S— or —NH—, and
X⁷ is -halogen;
thereby decreasing virulence of the bacterium.

In some embodiments of the methods disclosed herein, the at least one compound has a structure selected from the group consisting of:

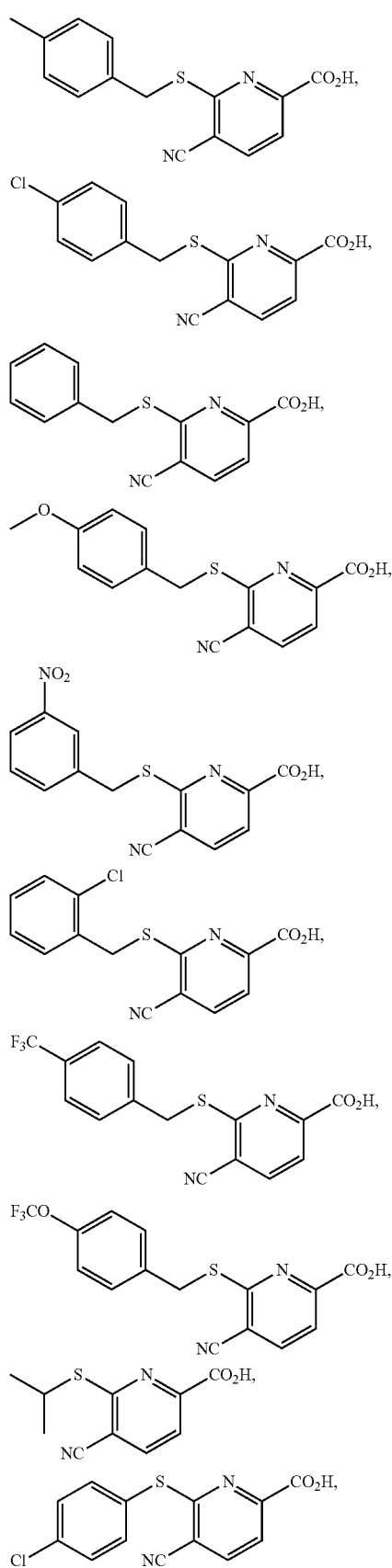
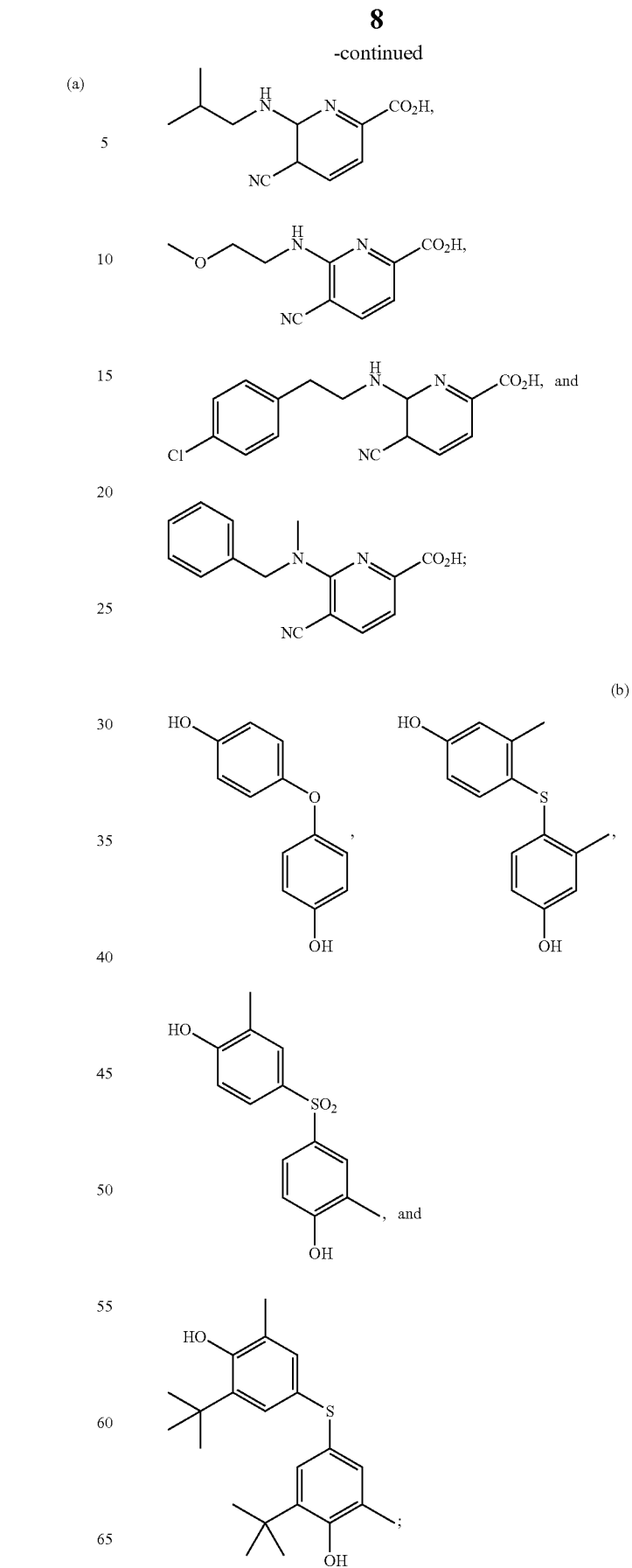

-continued
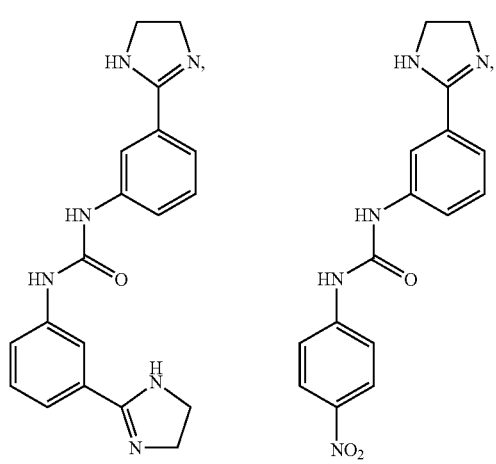
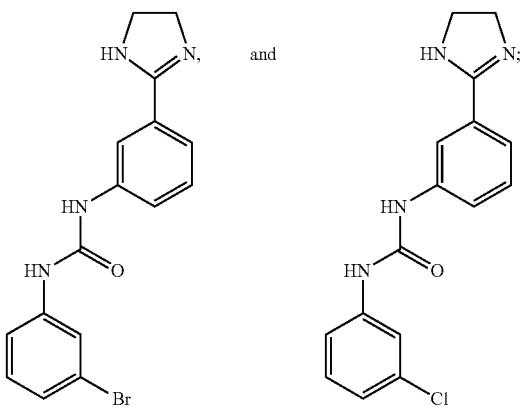
(c)
-continued
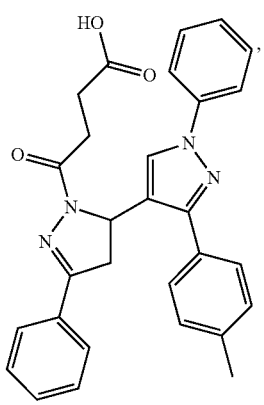
(d)
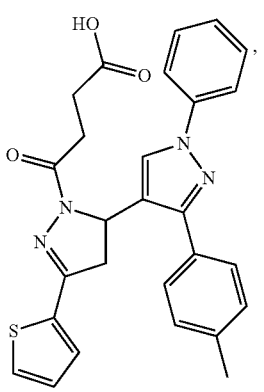
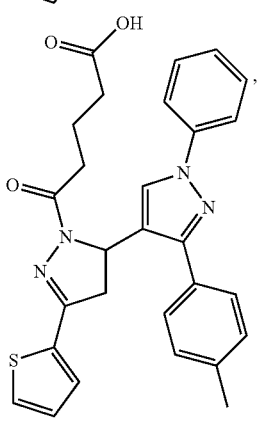

-continued

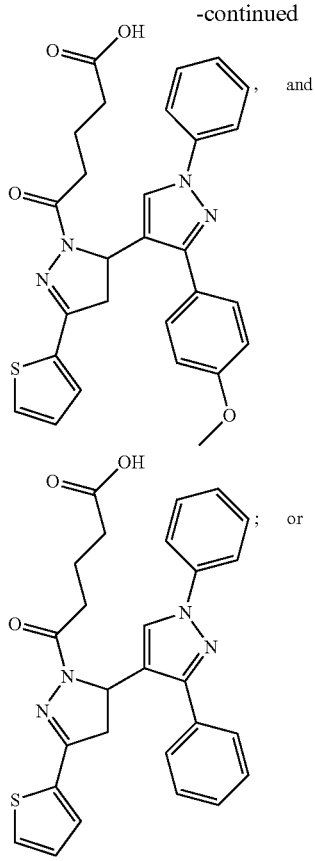

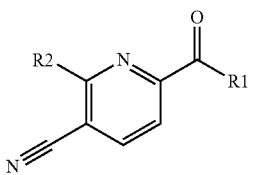

or a pharmaceutically acceptable salt thereof,
and if R1 is —OH, and R2 is

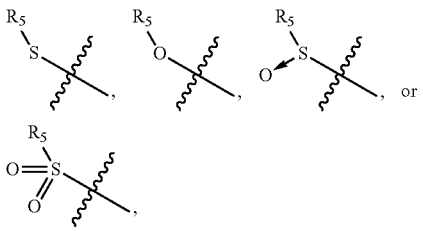

then R5 is not

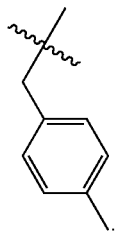 [SMILES: *Cc1ccc(C)cc1]

In some embodiments of the methods disclosed herein, if the at least one compound is a compound of the formula:

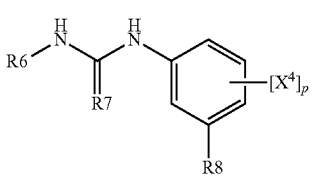

or a pharmaceutically acceptable salt thereof,
and R6 is

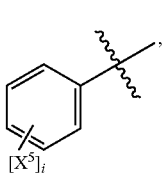

In some embodiments of the methods disclosed herein, if the at least one compound is a compound of the formula:

then each $X^5$ is not:

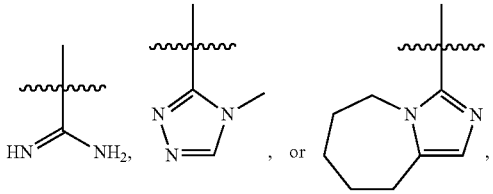

and R8 is not:

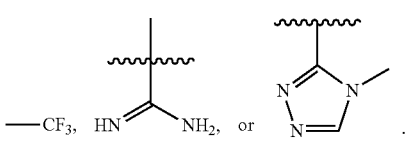

In some embodiments of the methods disclosed herein, the at least one compound is not a compound of the formula:

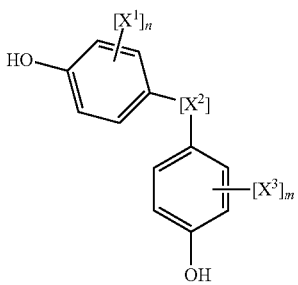

or a pharmaceutically acceptable salt thereof.

In some embodiments of the methods disclosed herein, the at least one compound is not a compound of the formula:

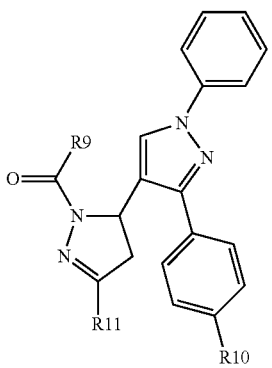

or a pharmaceutically acceptable salt thereof.

In some embodiments of the methods disclosed herein, if the at least one compound is a compound of the formula:

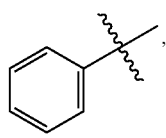 [SMILES: *c1ccccc1]

or a pharmaceutically acceptable salt thereof, and if R8 is hydrogen and R7 is =O, then R6 is not

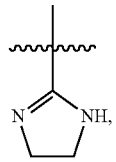 [SMILES: *C1=NCCN1]

and if R8 is

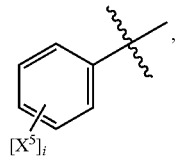

R7 is =O and R6 is

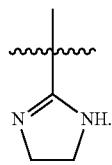

then $X^5$ is not

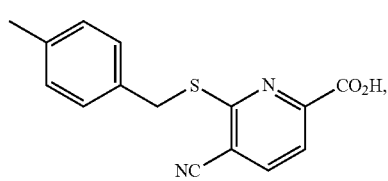

In some embodiments, the at least one compound is not a compound listed in Table 1, 2, 11 or 12, or pharmaceutically acceptable salts thereof.

In some embodiments, the at least one compound is not a compound selected from:

-continued

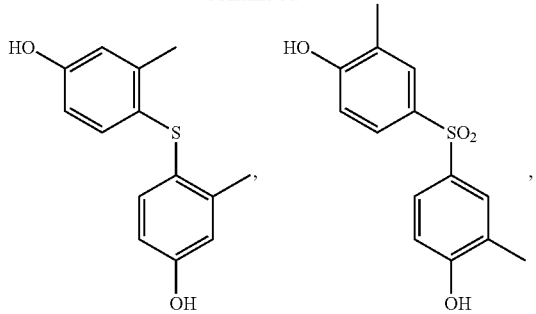

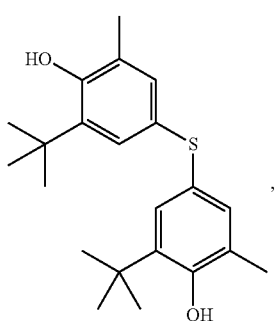

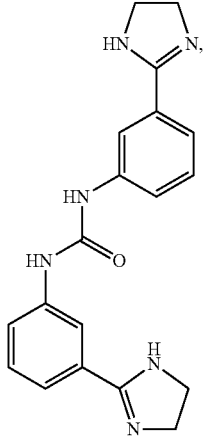

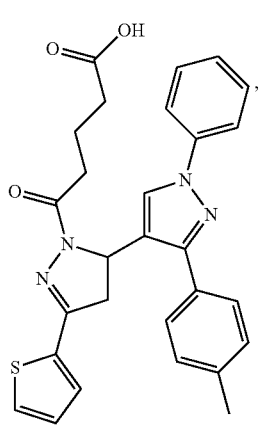

-continued

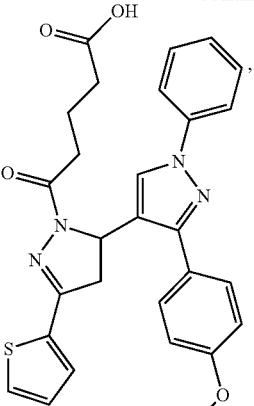

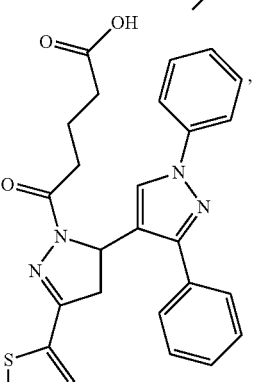

and pharmaceutically acceptable salts thereof.

According to some aspects, methods for identifying a compound that inhibits low-calcium response in a bacterium are provided. In some embodiments, the methods involve:

(a) combining (i) a population of the bacterium, wherein the bacterium comprises a type III secretion system, with (ii) a sample of a test compound;

(b) incubating the combination in $Ca^{++}$-depleted broth under conditions suitable for testing the low-calcium response; and (c) determining growth of the population, wherein an increase in growth compared to a reference is associated with inhibition of the low-calcium response in the bacterium by the test compound, thereby identifying a test compound that inhibits low-calcium response in the bacterium.

In some embodiments, the methods for identifying a compound that inhibits low-calcium response in a bacterium further comprise:

(a) combining (i) a population of the bacterium, comprising the type III secretion system, with (ii) a sample of the test compound, (b) incubating the combination in $Ca^{++}$-supplemented broth, and (c) determining growth of the population in the $Ca^{++}$-supplemented broth.

In some embodiments, the bacterium further comprises a reporter gene, wherein the level of expression of the reporter gene provides a measure of growth of the population of the bacterium. In certain embodiments, the reporter gene is a lux operon. In one embodiment, the lux operon is from *Photorhabdus luminescence*.

In some embodiments, the methods for identifying a compound that inhibits low-calcium response in a bacterium further comprise:

(a) combining (i) a sample population of the bacterium, comprising the type III secretion system, with (ii) a sample of the test compound, (b) incubating the combination in $Ca^{++}$-depleted broth, (c) measuring the level of at least one protein secreted by the type III secretion system in the broth, and (d) comparing the level of the at least one protein to a reference, wherein a decrease in the level of the at least one protein, compared with the reference, indicates that the test compound inhibits the type III secretion system.

In some embodiments of the methods for identifying a compound that inhibits low-calcium response in a bacterium, the bacterium is a *Yersinia* species. In certain embodiments, the *Yersinia* species is *Yersinia Pestis, Yersinia pseudotuberculosis*, or *Yersinia enterocolitica*. In other embodiments, the bacterium is selected from: *Yersinia pestis, Yersinia enterocolitica, Yersinia pseudotuberculosis, Salmonella enterica, Escherichia coli, Shigella dysenteriae, Shigella flexneri, Shigella boydii, Shigella sonnei, Bordetella pertussis, Bordetella parapertussis, Bordetella bronchiseptica, Pseudomonas aeruginosa, Burkholderia pseudomallei, Vibrio parahaemolyticus, Vibrio cholerae, Chlamydia trachomatis, Chlamydia pneumoniae*, and *Chlamydia psittaci.*

In some embodiments, the conditions suitable for testing a low-calcium response in the bacterium comprise incubation of the bacterium at a temperature above 34 degrees Celsius.

In some embodiments, the conditions suitable for testing a low-calcium response in the bacterium comprise incubation of the bacterium at a temperature of approximately 37 degrees Celsius.

In some embodiments, the at least one protein secreted by the type III secretion system is a *Yersinia* outer protein (Yop). In certain embodiments, the Yop is YopM, YopH, or YopD.

In some embodiments, the methods for identifying a compound that inhibits low-calcium response in a bacterium further comprise examining the test compound in a cytotoxicity assay. In certain embodiments, the cytotoxicity assay comprises incubating a sample of the test compound with a eukaryotic cell under conditions suitable for measuring survival of the eukaryotic cell in the presence of the test compound. In some embodiments, the eukaryotic cell is a mammalian cell. In some embodiments, measuring survival comprises performing microscopy of the eukaryotic cell.

In some embodiments, the methods for identifying a compound that inhibits low-calcium response in a bacterium may be implemented for screening a library of one or more test compounds, e.g., in a high-throughput manner. In certain embodiments, the high-throughput manner comprises autodispensing the population of bacteria into multiwell plates. In certain embodiments, the high-throughput manner comprises performing a pin transfer of the one or more test compounds into multiwell plates.

According to some aspects compounds are provided that have the formula:

or a pharmaceutically acceptable salt thereof, wherein:

R1 is selected from the group consisting of:

—O—(C1-C5)alkyl,

—NH—(C1-C5)alkyl,

—$NH_2$, and

—OH, and

R2 is or 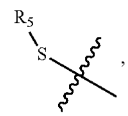 , 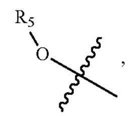 ,

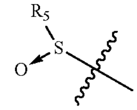

, 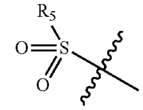 , wherein:

R3 and R4 are joined as a five- or six-member heterocyclic ring that may be further substituted at any one position with —CO—O—(C1-C5)alkyl or (C1-C5) alkyl, or R3 is —H or —(C1-C5)alkyl and R4 is selected from the group consisting of:

—(C1-C5)alkyl,

—(C3-C8)cycloalkyl,

—(C1-C5)alkyl-O—(C1-C5)alkyl,

—(C1-C5)alkyl-hydroxyl,

-phenyl, and

—(C1-C5)alkyl-phenyl, wherein the phenyl group may be independently substituted at one, two, or three positions with —(C1-C5)alkyl or -halogen, and R5 is selected from the group consisting of:

—(C1-C5)alkyl,

—(C3-C8)cycloalkyl,

-phenyl, and

—(C1-C5)alkyl-phenyl, wherein the phenyl group may be substituted at one, two, or three positions with a substituent independently selected from the group consisting of:

—(C1-C5)alkyl,

—O—(C1-C5)alkyl,

-halogen,

—$NO_2$,

—$CF_3$, and

—$OCF_3$, and wherein if R1 is —OH, then R5 is not

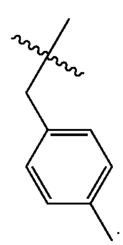 [SMILES: *Cc1ccc(C)cc1]

In certain embodiments, the compound is selected from the group consisting of:

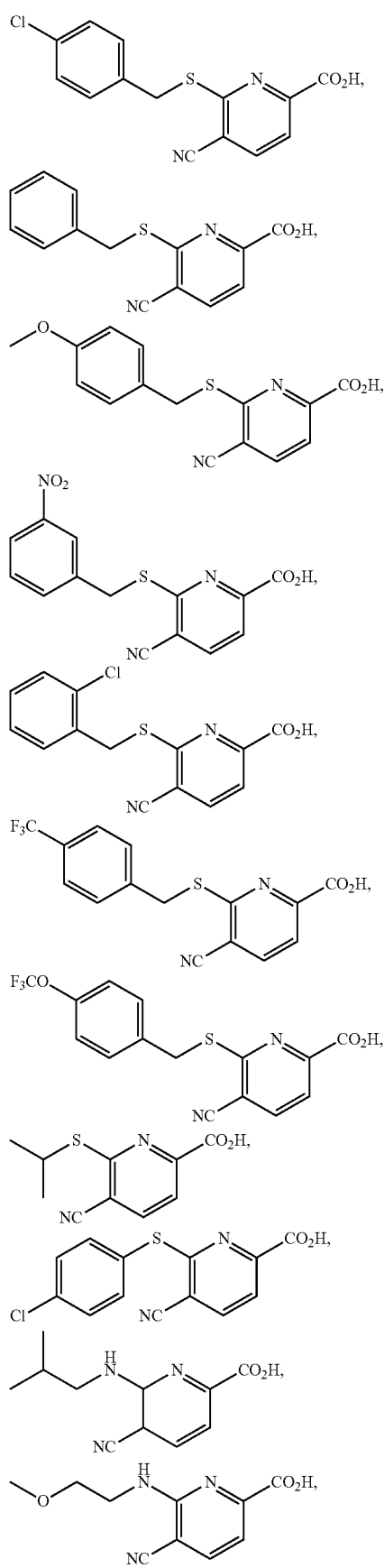

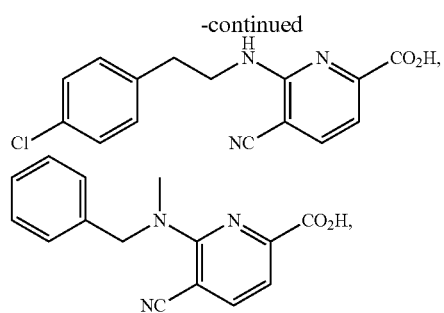

and pharmaceutically acceptable salts thereof.

According to some aspects compounds are provided that have the formula:

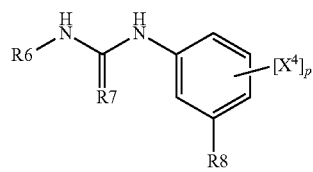

or a pharmaceutically acceptable salt thereof,
wherein:
R6 is selected from the group consisting of:

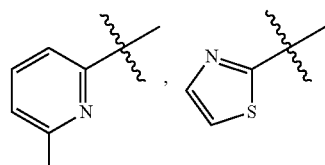

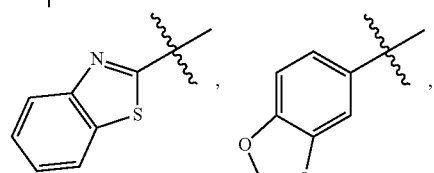

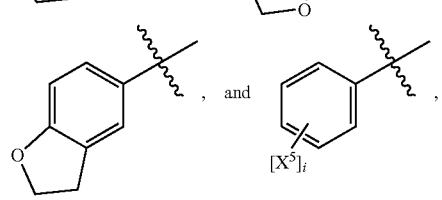

wherein i is an integer from 0 to 2, and wherein each $X^5$ is independently selected from the group consisting of:
—(C1-C6)alkyl,
—O—$(C_1$-$C_6)$alkyl,
—CO—(C1-C6)alkyl,
—CO—O—(C1-C6)alkyl,
—$NO_2$,
—CN,
-halogen,
—$CF_3$, and

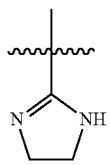

R7 is =O or =S,
R8 is -hydrogen or

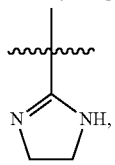

wherein if R8 is hydrogen and R7 is =O, then R6 is not

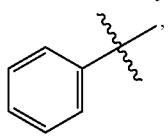

and wherein if R8 is

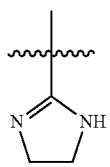 [SMILES: *C1=NCCN1]

and R7 is =O, then $X^5$ is not

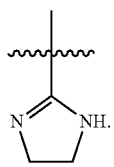 [SMILES: *C1=NCCN1]

$X^4$ is -halogen, and
p is 0 or 1.

In certain embodiments, the compound is selected from the group consisting of:

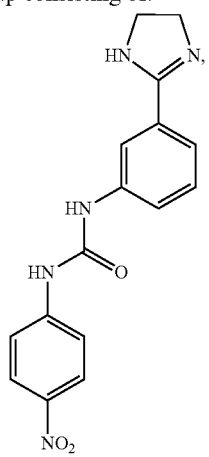
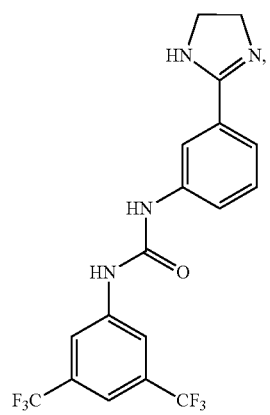
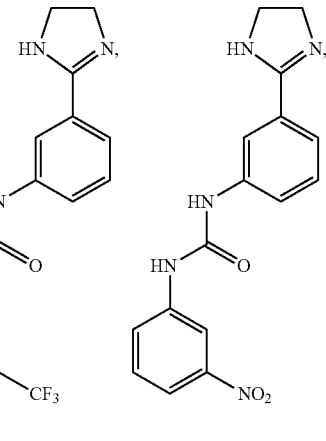
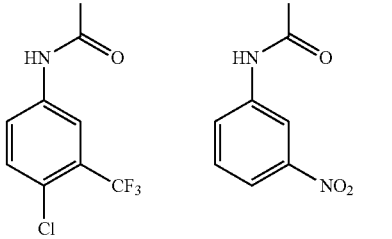
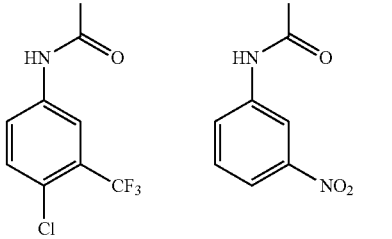
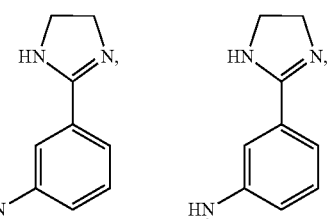
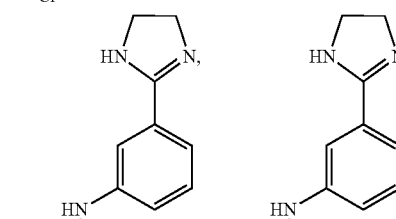
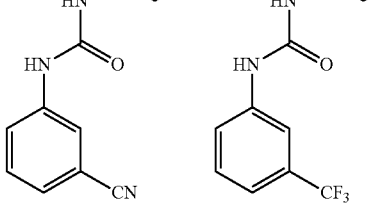
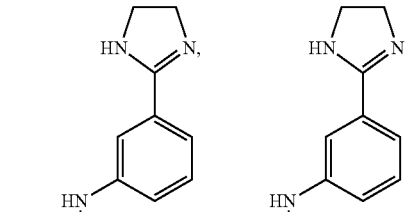
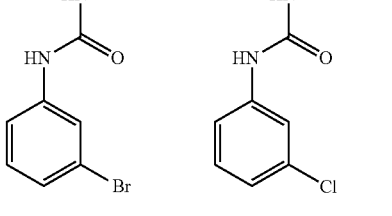
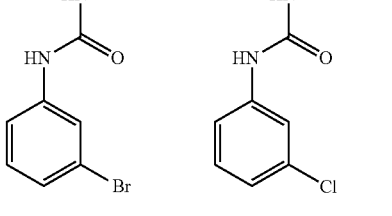

and pharmaceutically acceptable salts thereof.

According to some aspects compounds are provided that have the formula:

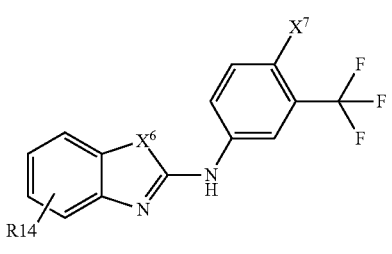

or a pharmaceutically acceptable salt thereof, wherein:
R14 is

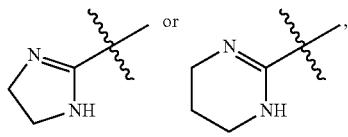 [SMILES: *C1=NCCN1 ; *C1=NCCCN1]

$X^6$ is —O— or —S— or —NH—, and
$X^7$ is -halogen.

In some embodiments, the compound has a formula selected from the group consisting of:

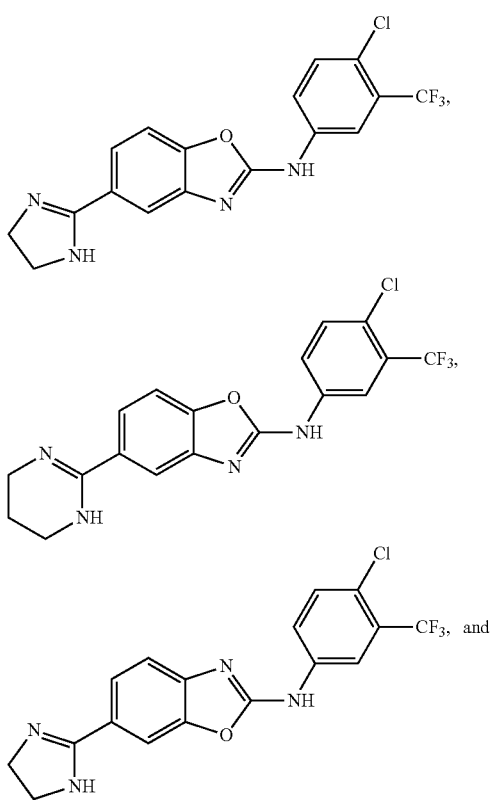

pharmaceutically acceptable salts thereof.

In some embodiments, the compounds disclosed herein inhibit type III secretion in a bacterium.

In some embodiments, compositions are provided that comprise a compound disclosed herein. In some embodiments, the compositions further comprise a pharmaceutically acceptable carrier. In some embodiments, the compound of the composition is provided in an amount effective for inhibiting a type III secretion system of a bacterium in a subject. In some embodiments, the bacterium is selected from the group consisting of: Yersinia pestis, Yersinia enterocolitica, Yersinia pseudotuberculosis, Salmonella enterica, Escherichia coli, Shigella dysenteriae, Shigella flexneri, Shigella boydii, Shigella sonnei, Bordetella pertussis, Bordetella parapertussis, Bordetella bronchiseptica, Pseudomonas aeruginosa, Burkholderia pseudomallei, Vibrio parahaemolyticus, Vibrio cholerae, Chlamydia trachomatis, Chlamydia pneumoniae, and Chlamydia psittaci.

In some embodiments, Type III secretion inhibitor compounds are provided (e.g., as listed in FIG. 3, FIG. 10, Table 1-8 and Tables 11-12).

In some embodiments, the disclosure provides the use of a therapeutically effective amount of any of the compounds disclosed herein in the manufacture of a medicament. In some embodiments, the compounds inhibit Type III secretion of a bacterium (e.g., a Yersinia sp.). In some embodiments, the medicaments are useful for treating a subject (e.g., a subject infected with a bacterium, e.g., a bacterium disclosed herein).

DETAILED DESCRIPTION

Plague is a widespread zoonotic disease and has had devastating effects on the human population throughout history. *Yersinia pestis*, the causative agent of plague, and other pathogenic yersinae (*Y. pseudotuberculosis* and *Y. enterocolitica*) comprise a type III secretion system (T3SS) expressed by a 70 kb plasmid termed pCD1 (sometimes called pYV). *Yersinia* spp. utilize the plasmid encoded T3SS to promote infection by injecting a set of *Yersinia* outer proteins (Yops) into the cytosol of eukaryotic host cells, causing inhibition of the innate immune response, which enables *Yersinia* spp. to survive and multiply in the lymphoid tissues of their host. T3SS is absolutely required for *Yersinia* virulence and is present in many other gram-negative species, including *Salmonella* spp., *Shigella* spp., *Pseudomonas aeruginosa*, entheropathogenic *Escherichia coli* (EPEC), enterohemorragic *E. coli* (EHEC), and *Chlamydia* spp.

The virulence plasmid encodes the Yop virulon, a system which is composed of a secretion apparatus, called Ysc injectisome, devoted to the secretion of Yop proteins; a deliver system, which is made of YopB, YopD, and LcrV, designed to translocate other Yops across the target cell membrane; a regulation system that controls the transcription and secretion; a set of small individual chaperones, called the Syc proteins; and an array of effector Yops (YopH, YopE, YopM, YopO/YpkA, YopP). This mixture of the Yop effector proteins disarm target cells or disrupt their signaling cascades and block the response of the host immune system to infection. The transcription of the Yop virulon genes is regulated by temperature, by extracellular calcium, and by the activity of the secretion apparatus, e.g. its contact with a eukaryotic cell. T3SS-associated genes are maximally expressed at 37° C. with depletion of extracellular calcium. This is known as low-calcium response (LCR), also characterized by restriction of the bacterial growth above 34° C. Although why the lack of calcium results in induction, and how exactly induction prevents growth, are still not clear, researchers had found that a temperature-dependent transcriptional activator LcrF regulates the expression of Yop genes. In the presence of calcium, Yop secretion is blocked during in vitro growth. LcrQ, YopD and their respective chaperones, including LcrH, are implicated during the process, which function to prevent high-level transcription before triggering T3SS. LcrH is also an important mediator of $Ca^{2+}$ regulation of pCD1-encoded genes in Yersinia.

Figure 12:
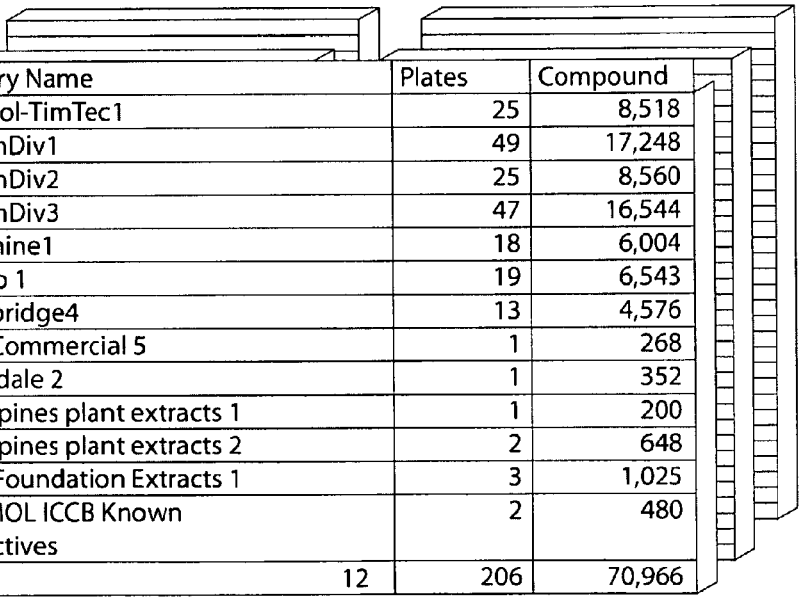
FIG. 12. Overview of the HTS compound and extract library.

Type III Secretion (T3S), which has since proven to be essential to virulence in at least 25 gram-negative species and is certainly among the most import discoveries in pathogenic microbiology, was first recognized by the remarkable insight of Hans Wolf-Watz and collaborators during study of Y. pseudotuberculosis in the early 1990s (Rosqvist et al., 1991; Rosqvist et al., 1994). However, the first in vitro phenotype directly related to T3S was observed more than 40 years earlier. Unfortunately, while rather useful as a tool, this phenotype was quite confusing and bore no obvious relationship to virulence. Virulent Y. pestis strains were observed to grow well in common laboratory media when incubated at temperatures below 30° C., but not when incubated at 37° C. Curiously, prolonged incubation at 37° C. did lead to growth, but the bacteria recovered from such cultures were avirulent. Addition of skim milk to the medium allowed the growth of virulent strains at 37° C., and the key component of skim milk was ultimately found to be calcium (Higuchi et al., 1959). Later studies showed that this requirement for calcium, along with the production of certain antigens, was dependent on the presence of a 70 kb plasmid, referred to as pCD1 (Ben-Gurion and Shafferman, 1981; Ferber and Brubaker, 1981). Spontaneous loss of, or formation of deletions within, this plasmid during prolonged incubation both permitted growth at 37° C. in the absence of calcium, but also lead to avirulence. This requirement for calcium at 37° C. is, at least in part, directly related to the activation of T3S: in the absence of calcium at approximately 37° C. induction of T3S occurs in all three *Yersinia* species and growth is simultaneously arrested or greatly slowed. Growth after prolonged incubation without calcium results from loss or mutation of pCD1, resulting in dysfunction of the T3S system, and therefore loss of virulence.

The secretion system is an attractive target in the development of new therapeutic antimicrobial agents (antibiotic compounds), and several inhibitory compounds from a 9,400 compound library, by using a transcriptional reporter gene assay, controlled by yopE promoter, in *Y. pseudotuberculosis* have been identified (Kauppi et al 2003). The compounds inhibit the reporter gene expression from yopE promoter and Yop secretion with no or modest effect on bacterial growth. INP0400, an analog of INP0007, was later proven to have some efficacy in treatment of mice infected with the intracellular pathogen *C. trachomatis*. Since type III secretion is controlled by other complex regulations beside the transcriptional level regulation, screening T3SS inhibitors using a different assay could presumably result in different set of compounds.

Applicants developed and conducted a novel whole-bacteria luminescence high-throughput screening (HTS) in *Y. pestis*. The assay is based on the temperature and $Ca^{2+}$ regulation of the T3SS, and the link between the regulation and the bacterial growth. The link of the in vitro growth defect and T3SS provide an opportunity to find small molecules that are able to promote bacterial growth in vitro and at same time inhibit the T3S in *Y. pestis*. In this study, Applicants disclose the characterization of a new set of inhibitors of T3S. The compounds are selected from the HTS, in which Applicants screened 70,966 compounds and mixtures from 13 small molecule and extract libraries. The selected compounds are from the strong and the moderate primary hits and their chemical structures are distinct from each other and from reported T3SS inhibitors. To explore the range of the inhibition spectrum Applicants also tested the compounds in enteropathic *E. coli* (EPEC).

Small molecule inhibitors of T3S are useful both as therapeutics and as probes of T3SS function. Moreover, such inhibitors are effective against a range of pathogens that have a T3SS. In contrast with antibiotics that target a broad spectrum of pathogens, with T3SS inhibitor based antibiotic compound it may be beneficial, but not necessary, to determine if an infecting bacteria has a T3SS. On the other hand, use of broad-spectrum antibiotics has selected for resistance, which is now a serious problem for treatment of some pathogens, a problem that is likely to become more widespread. For certain organisms, like *Y. pestis*, which have marked potential for misuse in biological terrorism or warfare (biological warfare/biowarfare), and for which engineering of multiple antibiotic resistance is relatively simple, development of alternative therapeutics may be prudent. For these reasons, in addition to their utility as research tools, development and evaluation of specific inhibitors of key virulence functions like T3S is useful in discovery of new therapeutics. Moreover, the antibiotic compounds disclosed herein are useful for treating infections caused by bacteria that are resistant to other antibiotics (e.g., broad-spectrum antibiotics).

Several efforts to develop small molecule inhibitors and related technology specifically targeting T3SS have been reported. Abe et al. described a T3S inhibitor screening assay (Abe, 2002). Caminoside A, from the extract of the marine sponge *Caminus sphaeroconia*, showed potent activity in another screen for bacterial T3S inhibitors. Bioassay guided fractionation of the extract led to the isolation of the novel antimicrobial glycolipid caminoside A (Linington et al., 2002). Kauppi et al. developed a reporter gene screening assay, and screened a 9,400 compound-library (Kauppi et al., 2003) (Nordfelth et al., 2005). Screening for T3S inhitors in pathogenic *E. coli* (Gauthier et al., 2005) has also been reported.

Screening for Antibiotic Compounds Affecting Type III Secretion Systems:

In one embodiment Applicants disclose a rapid, convenient, and inexpensive method for high-throughput screen for type III secretion (T3S) inhibitors in, for example, *Y. pestis*. Other pathogenic microorganisms described herein that comprise a Type-III secretion system can also be used. In comparison with previously reported techniques, this method is faster, simpler to execute, and requires minimal reagents other than bacteriological media and the compounds to be tested. The method is based on the expectation that at least some classes of T3S inhibitors (e.g., small-molecules that block Type III secretion) will suppress the low calcium response (LCR).

Provided herein, are methods of screening for inhibitor molecules using high-throughput screening. A high-throughput screening assay is an assay that allows the screening of one or more inhibitor molecules in parallel. In one embodiment, using the screening assay described above, 70,966 compounds (FIG. 12) were screened using the method disclosed herein. Generally the screening method involves assaying for inhibitor molecules that affect the low calcium response in bacteria comprising a type III secretion system in order to identify compounds that affect type III secretion. The assay comprises at least one candidate inhibitor molecule, also referred to as a test compound. Typically, in a screening assay, a plurality of assays are run in parallel (e.g., in a high-throughput manner) and each assay is carried out with a different test compound. In some embodiments, the test compounds are pooled such that each assays contains a plurality of test compounds. Thus, test compounds can be purified compounds or a mixture of compounds (e.g., pooled test compounds, extracts, such as plant extracts). Methods for purification of compounds and identification of an active compound in a mixture are well known in the art. The assay may contain at least one negative control compound (e.g., an inactive compound), at least one positive control compound (e.g., an active compound), and a no compound control (e.g., a vehicle control).

In one embodiment, the assay is conducted with test compounds tested at different concentrations to examine the response to the various concentrations (i.e., a dose response analysis). Typically, one of these concentrations serves as a negative control, i.e., at zero concentration of candidate inhibitor molecule or at a concentration of candidate inhibitor molecule below the limits of assay detection.

The high-throughput screening assay may be based in a multiwell plate (e.g. 384-well plate). In one aspect, a bacterial cell is contacted with at least one candidate test compound in a multiwell plate. The level of growth of the bacteria is determined using methods disclosed herein. For example, the growth of a luminescent bacterial population can be assayed by measuring relative luminescence units (RLU) in the population compared with a reference (e.g., background RLU).

Depending on the specific assay used, the effects of test compounds on the bacteria are assayed at about 1, 2, 3, 4, 5, 10, 15, 20, 24, 36, 48, 60, 72, or 96 hours after the addition of test compounds. In a preferred embodiment of the invention, bacterial growth is assayed after an overnight (e.g., 12-24 hrs) incubation with test compounds. One of ordinary skill in the art is able to determine a suitable incubation time for assaying test compounds.

In certain embodiments, a specially constructed an avirulent Y. pestis strain, which meets the requirements for exemption for Select Agent status—and thus can be used outside of BSL-3 laboratories and secure facilities—but retains the intact T3S system, is used. Key properties of this specially constructed avirulent Y. pestis strain relevant to the screening assay include strong luminescence, the addition of a selectable marker to pCD1 that allows selection for retention of this plasmid, and stabilization of pCD1 against spontaneous deletion. In combination, these features permit the detection of potential T3S inhibitors by measuring bacterial growth (e.g., based on luminescence). Specially constructed strains of other pathogenic microorganism described herein that comprise a Type-III secretion system are contemplated and can be used with the screening methods described herein.

In one embodiment, a luminescent Y. pestis strain is constructed by introducing the lux operon from Photorhabdus luminescence contained in plasmid pML001 (AmpR), and a pCD1 derivative, pCD1K22, marked with a Mariner transposon derivative conferring kanamycin resistance, but lacking the Mariner transposase function and thus incapable of transposition. The location of this insertion is selected to reduce the rate of spontaneous internal deletions in pCD1. The invention is not limited to these DNA/plasmid constructs and other similar constructs are contemplated to produce test pathogen strains. In certain embodiments, a T3S deficient luminescent Y. pestis strain is constructed as a control. One example of such a control strain is JG406 (JG401 pCD1−).

In one embodiment, screening comprises measuring relative luminescent (light) units (RLU) as an indication of number of bacterial cells in a population. In certain embodiments, an increase in luminescence indicates an increase in bacterial cell number in a population (i.e., bacterial growth). The invention is not limited to this method of growth detection. Other suitable methods for detecting growth are well-known to one of ordinary skill in the art. For example, growth of bacterial populations can be measured by any one of the following methods known in the art: direct microscopic counting of cells, viable cell counting (e.g., colony counts), liquid culture turbidity measurements, measurement of biomolecular content (e.g., total protein, total DNA and total RNA), measurement of biochemical activity (e.g. $O_2$ uptake, $CO_2$ production, and ATP production), and measurement of dry weight or wet weight of cells or volume of cells after centrifugation.

In one embodiment, high throughput screening for inhibitors of T3S (e.g., in Yersinia) is performed. At approximately 37° C. with low or no $Ca^{2+}$ in bacterial culture, Y. pestis perform T3S with minimal, or no, growth. In one embodiment, active small molecules are identified that convert the phenotype to growth with no or reduced T3S (that increase RLU). In one embodiment a secondary confirmation screening assay is performed by adding selected primary hits (active small molecules) to the bacterial culture. Cultures then are incubated overnight at approximately 37° C., after which the RLU is measured. In addition to JG401, JG406 (T3S deficient) is also used in the secondary screening to ensure the tested compounds do not act as general bacterial growth inhibitors.

In one embodiment a follow-up assay for inhibition of T3S is performed. For example, Y. pestis overnight culture in TB is subcultured into brain-heart infusion (BHI) broth, then incubated at approximately 30° C. with aeration until mid-log phase. Test compounds at the desired concentrations are then added to the bacterial cultures. The cultures are shifted to approximately 37° C. for two to four hours to induce T3S, centrifuged, and the resulting supernatant assayed are for secreted proteins (e.g., Yops) via antibody-based enzyme-linked immunosorbent assay (ELISA) and immunoblot (other methods for protein detection are appropriate and will be known to one of ordinary skill in the art). Specific antibodies (e.g., anti-Yop antibodies) are typically used in these assays. However the invention is not limited to the use of specific antibodies. For example, if the assay comprises recombinant Yop proteins fused with non-Yop epitope tags, then use of antibodies to the non-Yop epitope tags (e.g., Hemagglutinin-based HA-tags) are possible.

Figure 3:
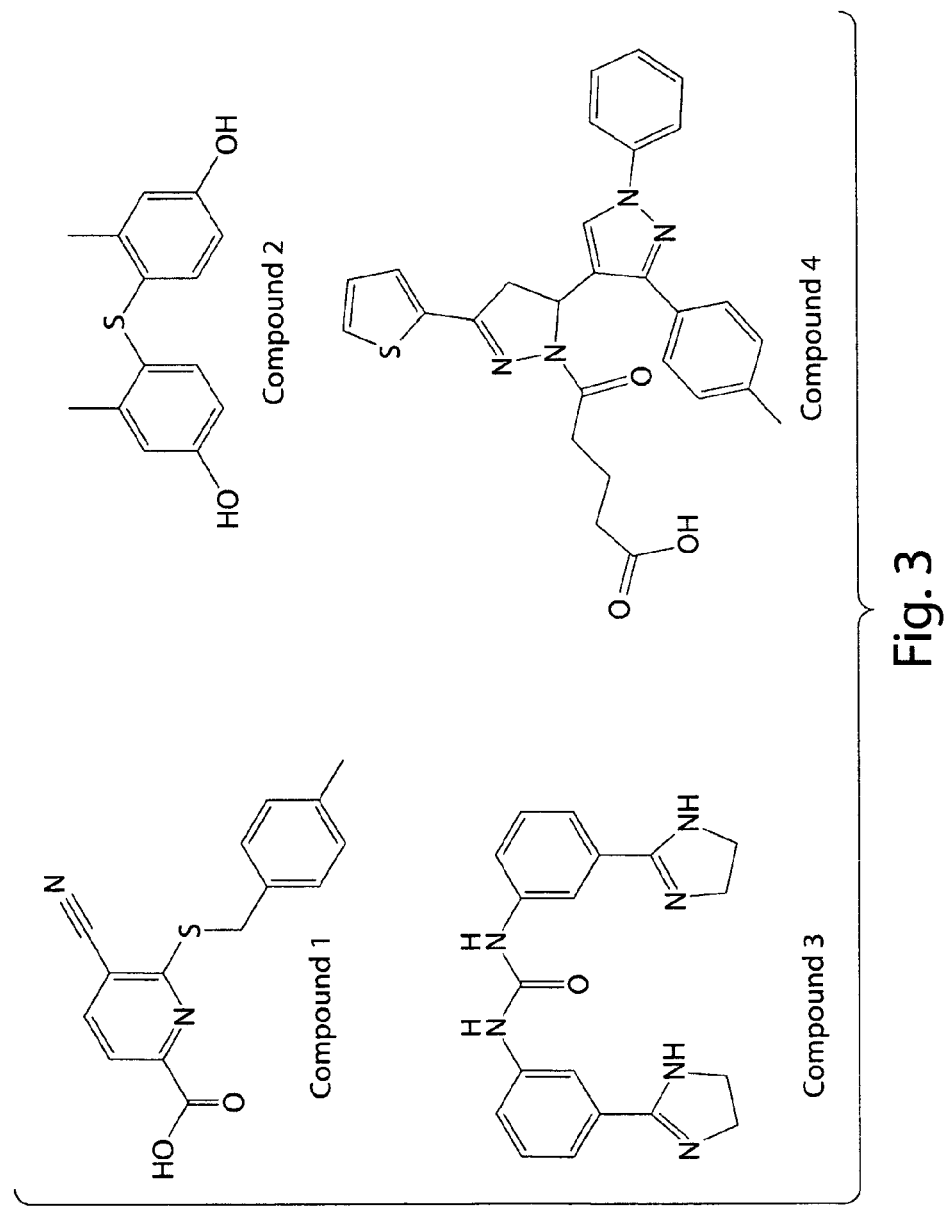
Figure 4A:
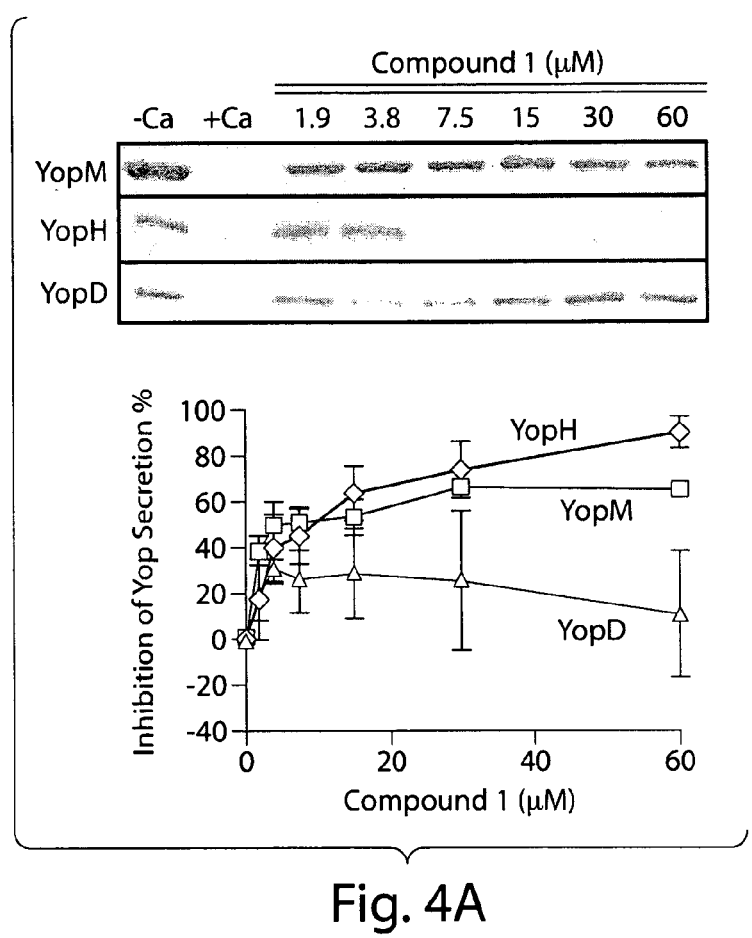
Figure 4B:
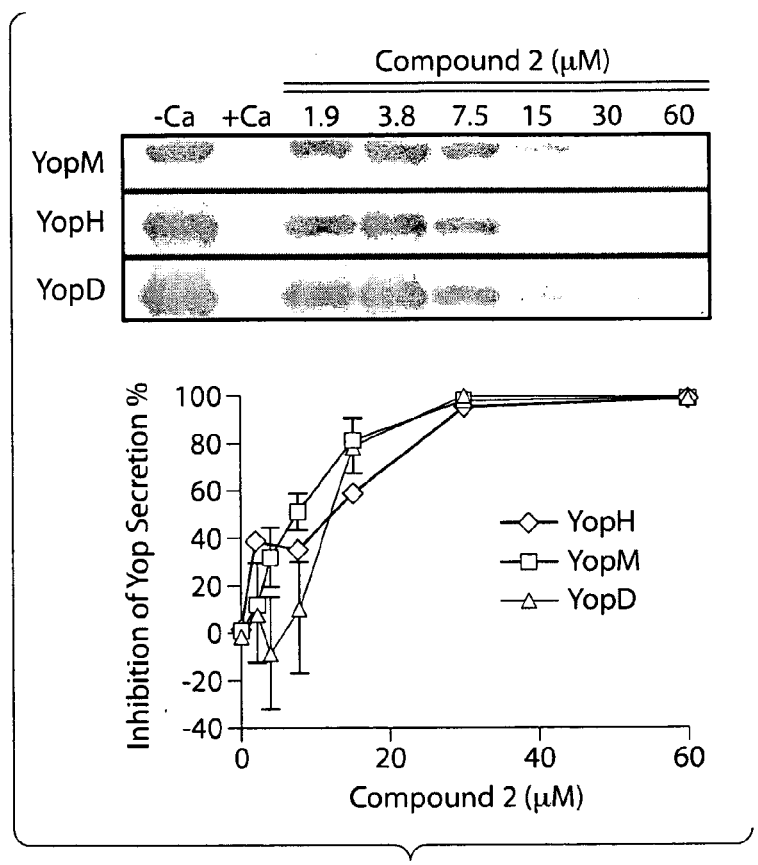
Figure 4C:
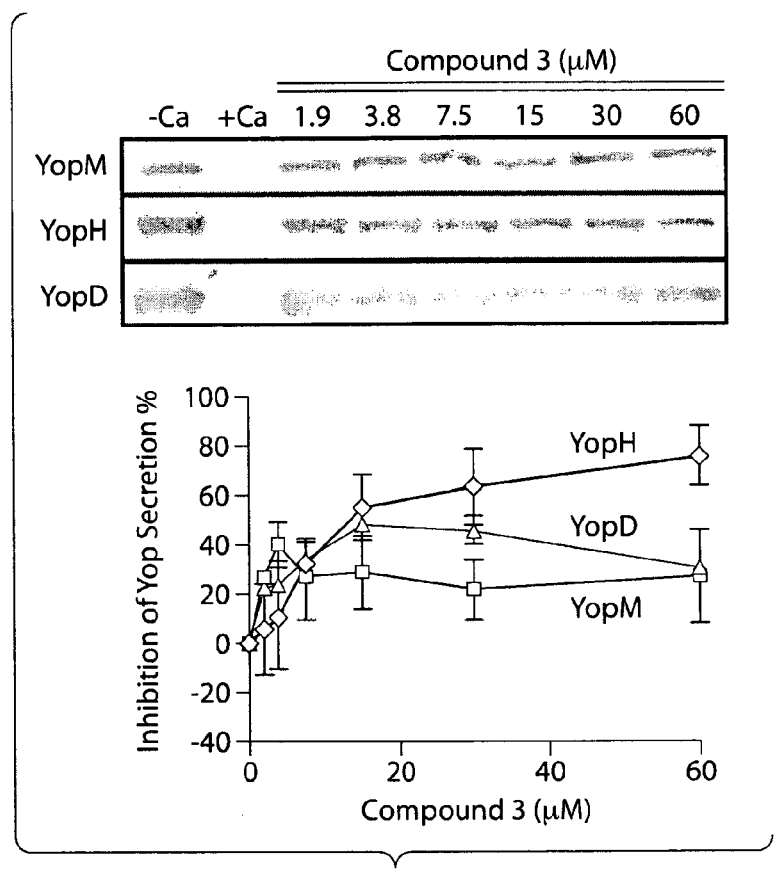
Figure 4D:
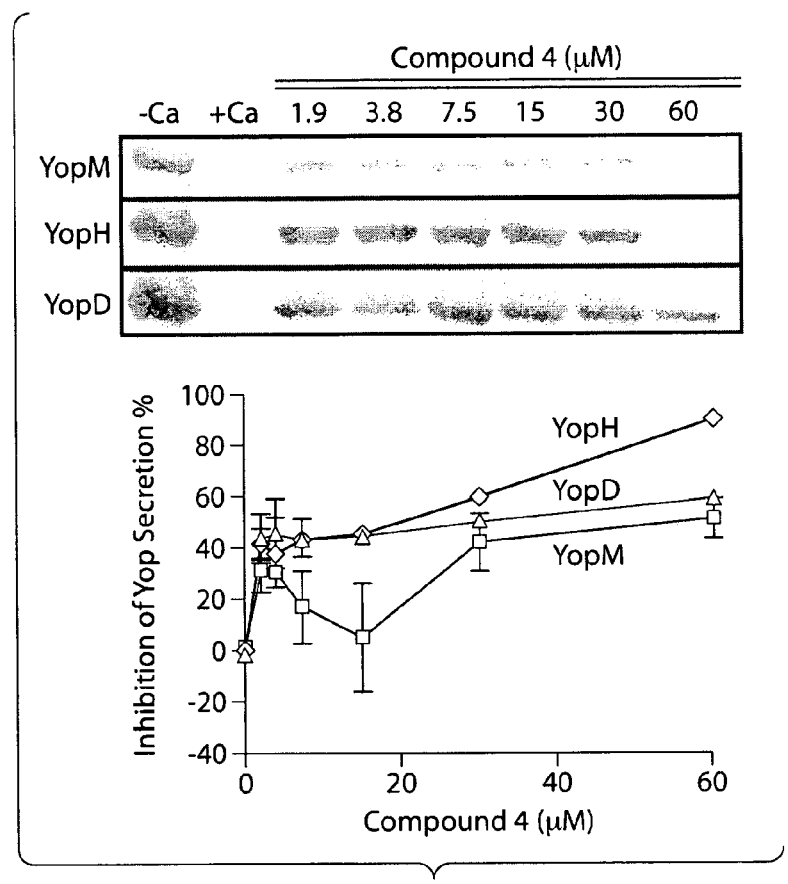
Figure 5:
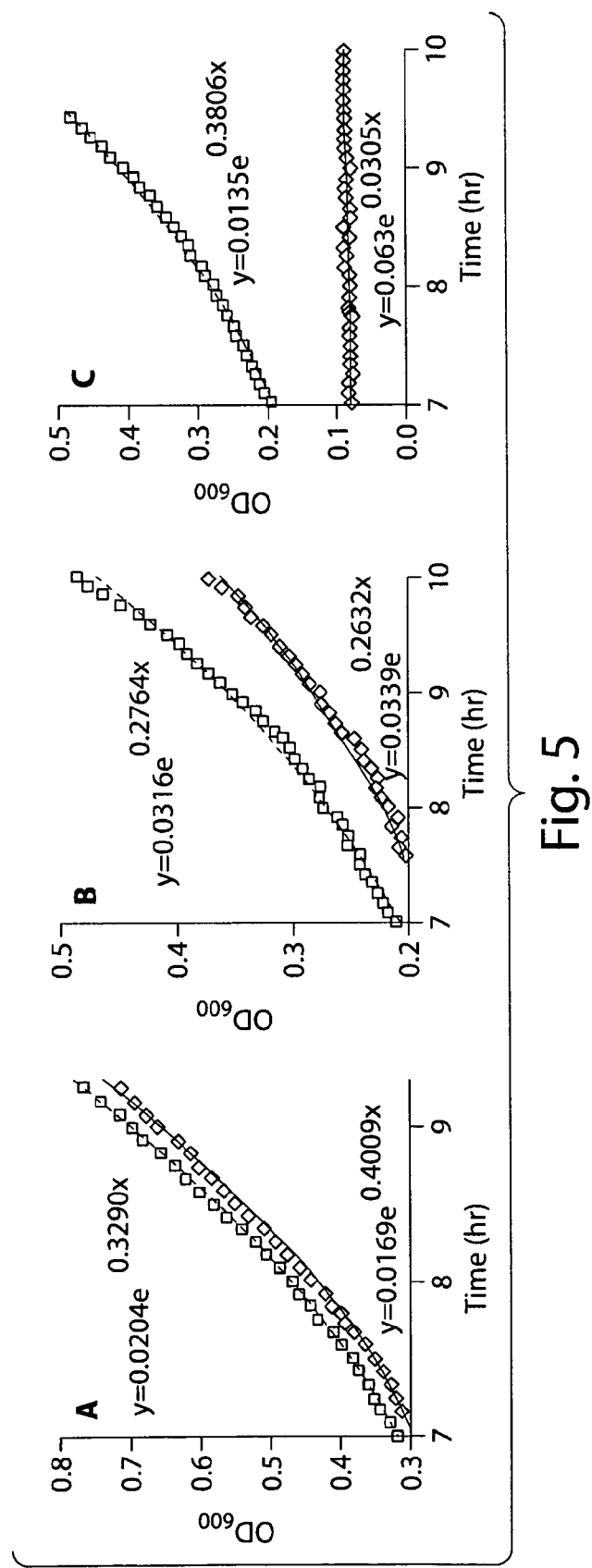
Figure 6:
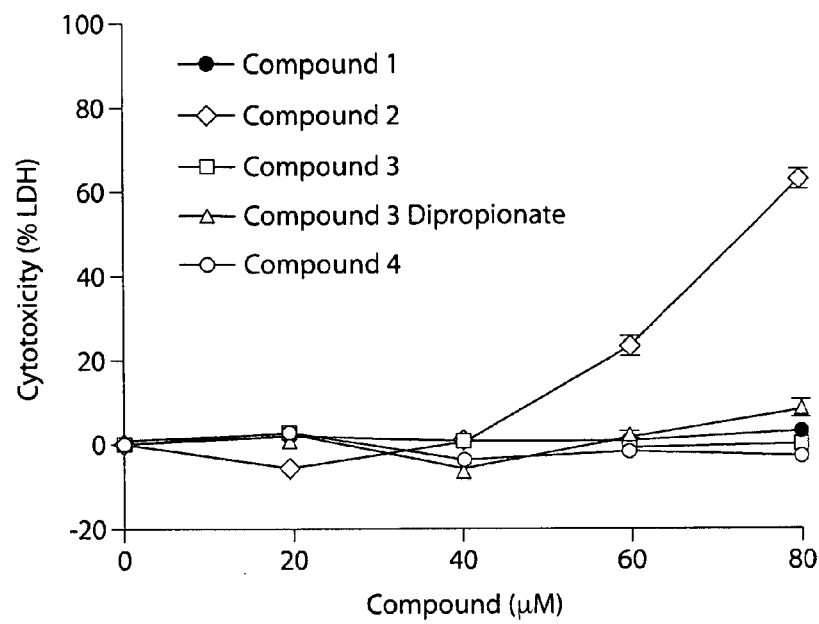
Figure 7A:
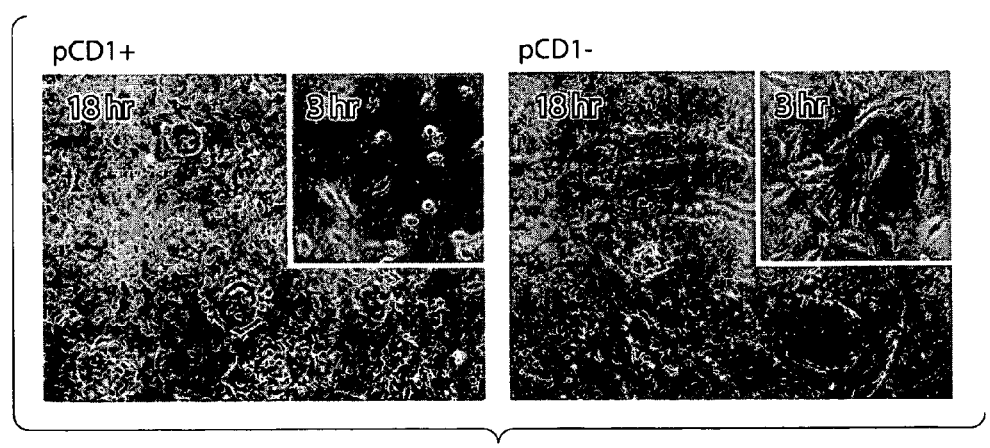
FIG. 7. Effect of compounds on T3S mediated cytotoxic response of HeLa cells infected by *Y. pestis*. (A) HeLa cells infected with *Y. pestis* JG153 (D122) (pCD1+, positive control) (left) and JG154 (pCD1−, negative control, right). The images were taken at 3 hr and 18 hr postinfection for low and high magnified images respectively. (B) The inhibition data obtained by addition of different concentrations of compounds 1, 3 (dipropionate), and 4 to Hela cells infected by *Y. pestis*. The morphological changes of HeLa cells were measured at 3 hr post-infection. Inhibition (%)=[1−(exp. roundup cell−roundup $cell_{-CT}$)/(roundup $cell_{+CT}$−roundup $cell_{-CT}$)]×100. Error bars represent standard deviations of the means from three assays.
Figure 7B:
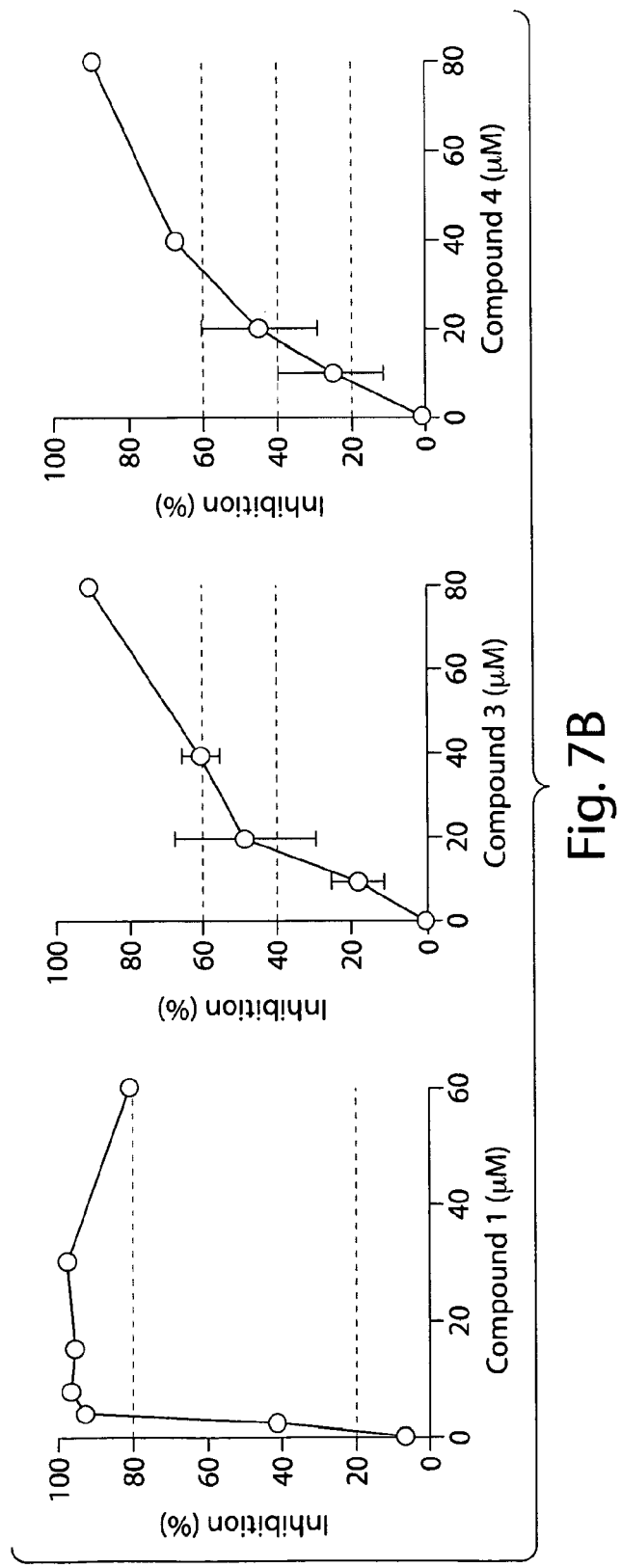
Figure 8:
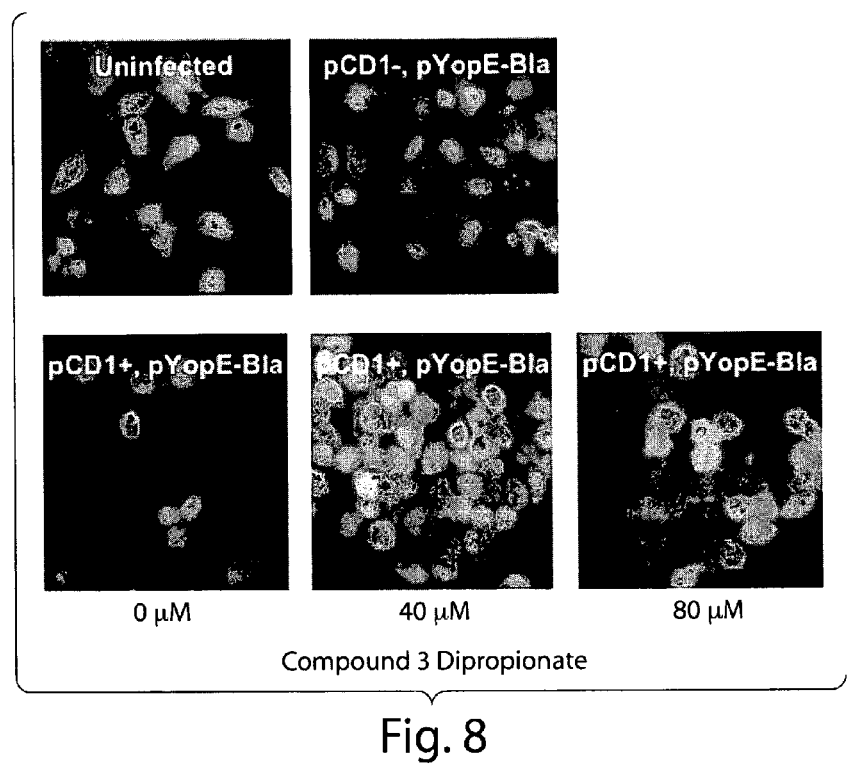
FIG. 8. Compound 3 dipropionate inhibits YopE-Bla translocation to HeLa cells. HeLa cells were infected by JG153 (pMM85, expressing YopE-Bla) then incubated at 37° C. for 3 hr. Compound 3 dipropionate was added to the cells culture at the time of infection prior the incubation. CCF2-AM was added and live cells were visualized by fluorescence microscopy. Bla: β-lactamase.
Figure 9:
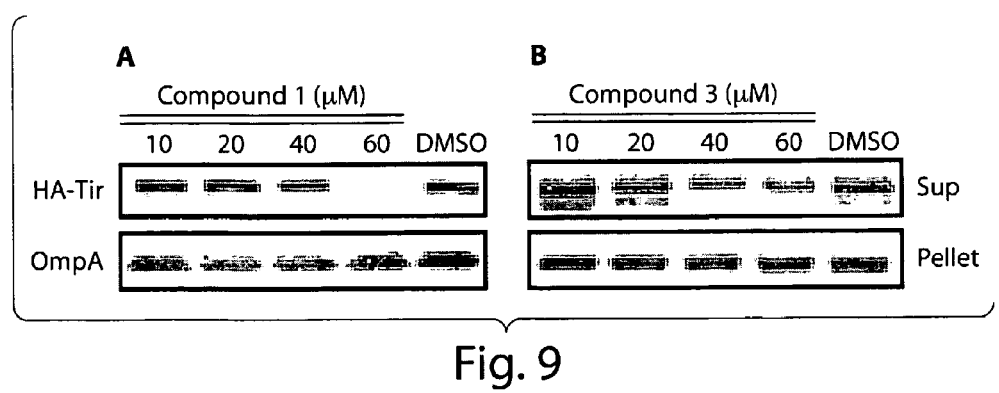
FIG. 9. Compounds 1 and 3 inhibit Type III secretion by enteropathogenic *E. coli*. Bacterial lysates (pellet) were subjected to anti-OmpA immunoblotting to determine the relative amount of EPEC tir expressing HA-tagged EPEC Tir after incubation in the presence of increasing concentrations of Compound 1(A) or Compound 3(B) or DMSO. In parallel, culture supernatants (Sup) were subjected to anti-HA immunoblotting to detect secreted HA-tagged EPEC Tir.
Figure 10:
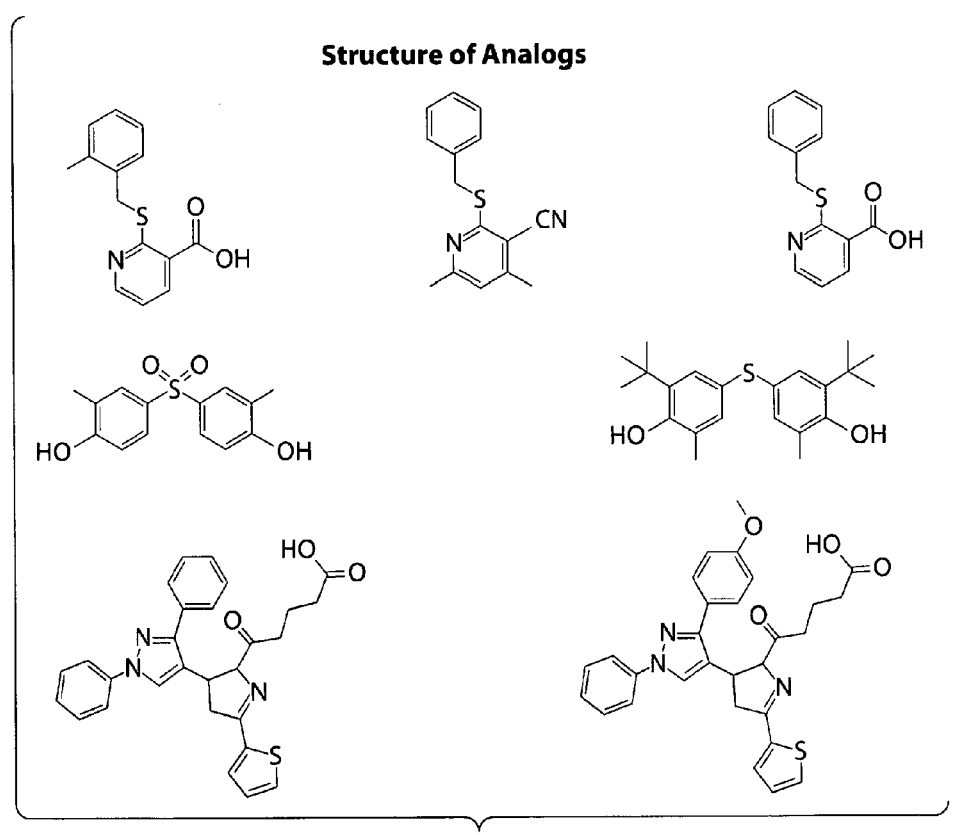
FIG. 10. Structure of analogs of compounds identified in the HTS.
Figure 11A:
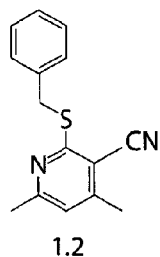
FIG. 11. Activity of analog compounds.
Figure 11A:
Figure 11A:
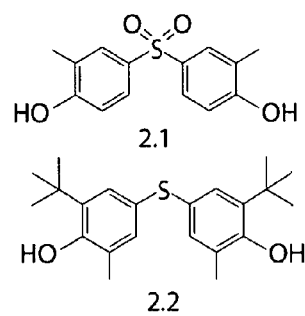
Figure 11A:
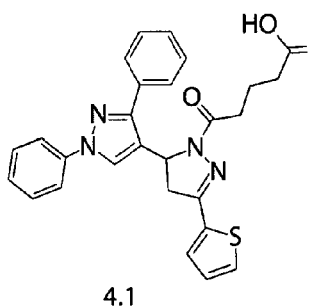
Figure 11A:
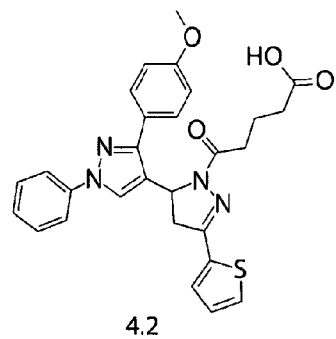
Figure 11B:
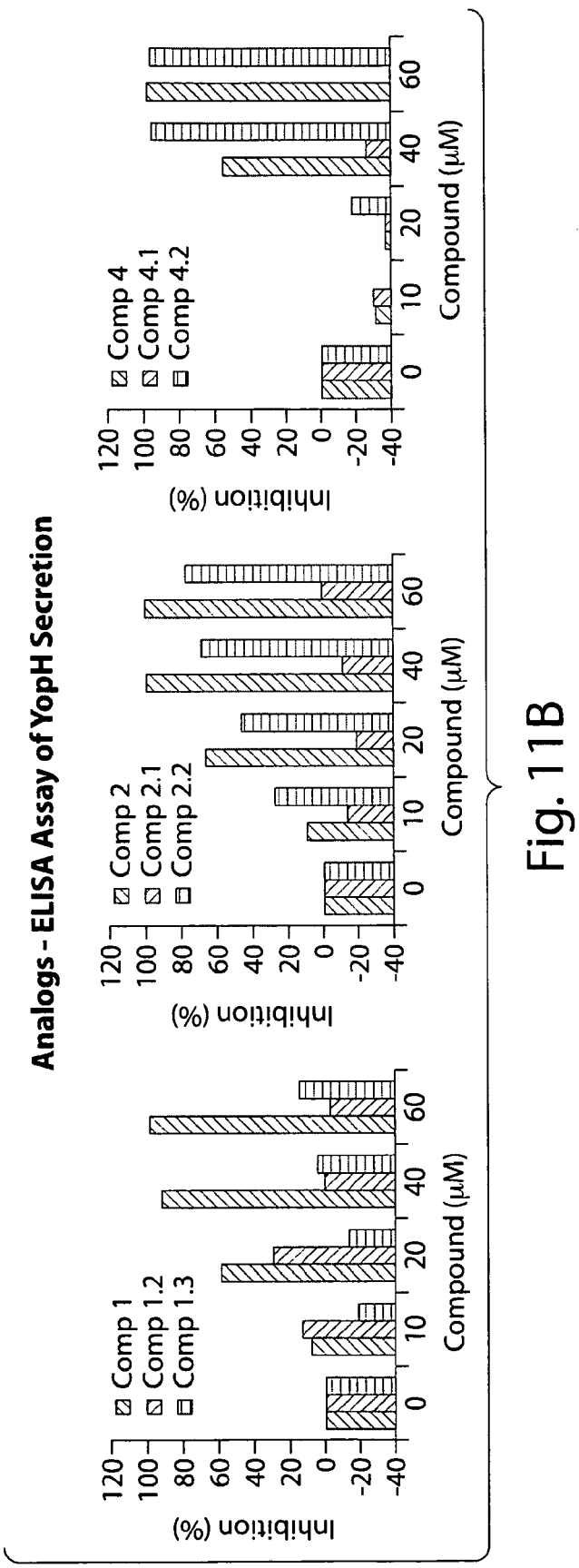

Type III Secretion Inhibitors:

Although it is indirect, measuring luminescence as a surrogate for growth and using growth as a surrogate for inhibition of secretion, is not only rapid, inexpensive, and convenient but also clearly yields bonafide T3S inhibitors. Because positive results depend on growth of the bacteria, this assay has the substantial advantage of efficiently excluding compounds that inhibit bacterial growth, and hence those that inhibit essential bacterial functions. This presumably excludes a wide range of compounds (e.g. protein or RNA synthesis inhibitors) that might yield false positives in more direct secretion assays. In one embodiment, disclosed herein, Applicants identified inhibitors by this method that are chemically diverse, each having a chemical scaffold distinct from one another, and also distinct from previous described candidate type III inhibitors. Examples of Type III secretion inhibitors identified through this screen are outlined in FIG. 3, FIG. 10, Table 1-8 and Tables 11-12, which are also referred to herein as "antibiotic molecules" and, equivalently, "T3S inhibitors".

Methods for synthesizing the compounds disclosed herein will be apparent to the skilled artisan. Exemplary methods are provided herein in the Examples. It is to be understood that these methods are not limiting and that other suitable methods known in the art may be used to synthesize the compounds disclosed herein. In some embodiments, the compounds are commercially available compounds.

The term "alkyl" as used herein refers to a saturated linear or branched-chain monovalent or divalent hydrocarbon radical of one to eighteen carbon atoms, wherein the alkyl radical may be optionally substituted independently with one or more substituents as described herein. Examples of alkyl groups include C1-C8 hydrocarbon moieties such as methyl (Me, —CH3), ethyl (Et, —CH2CH3), 1-propyl (n-Pr, n-propyl, —CH2CH2CH3), 2-propyl (i-Pr, i-propyl, —CH(CH3)2), 1-butyl (n-Bu, n-butyl, —CH2CH2CH2CH3), 2-methyl-1-propyl (1-Bu, i-butyl, —CH2CH(CH3)2), 2-butyl (s-Bu, s-butyl, —CH(CH3)CH2CH3), 2-methyl-2-propyl (t-Bu, t-butyl, —C(CH3)3), 1-pentyl (n-pentyl, —CH2CH2CH2CH2CH3), 2-pentyl (—CH(CH3)CH2CH2CH3), 3-pentyl (—CH(CH2CH3)2), 2-methyl-2-butyl (—C(CH3)2CH2CH3), 3-methyl-2-butyl (—CH(CH3)CH(CH3)2), 3-methyl-1-butyl (—CH2CH2CH(CH3)2), 2-methyl-1-butyl (—CH2CH(CH3)CH2CH3), 1-hexyl (—CH2CH2CH2CH2CH2CH3), 2-hexyl (—CH(CH3)CH2CH2CH2CH3), 3-hexyl (—CH(CH2CH3)(CH2CH2CH3)), 2-methyl-2-pentyl (—C(CH3)2CH2CH2CH3), 3-methyl-2-pentyl (—CH(CH3)CH(CH3)CH2CH3), 4-methyl-2-pentyl (—CH(CH3)CH2CH(CH3)2), 3-methyl-3-pentyl (—C(CH3)(CH2CH3)2), 2-methyl-3-pentyl (—CH(CH2CH3)CH(CH3)2), 2,3-dimethyl-2-butyl (—C(CH3)2CH(CH3)2), 3,3-dimethyl-2-butyl (—CH(CH3)C(CH3)3, 1-heptyl, and 1-octyl.

The term "cycloalkyl" as used herein refers to a monovalent or divalent saturated cyclic hydrocarbon radical of one to eighteen carbon atoms, wherein the cycloalkyl radical may be optionally substituted independently with one or more substituents as described herein. Examples of cycloalkyl groups include cyclopropyl, cyclobutyl, cyclopentyl, cyclohexyl, cycloheptyl, and cyclooctyl.

The terms "heterocycle," "heterocyclyl", "heterocyclic ring" refer to a saturated, a partially unsaturated (i.e., having one or more double and/or triple bonds within the ring) carbocyclic radical of 3 to 20 ring atoms in which at least one ring atom is a heteroatom independently selected from nitrogen, oxygen and sulfur, the remaining ring atoms being carbon, where one or more ring atoms is optionally substituted independently with one or more substituents described below. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7 and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The heterocyclyl may be a carbon-linked radical or heteroatom-linked radical. The term "heterocycle" includes heterocycloalkoxy. "Heterocyclyl" also includes radicals where heterocycle radicals are fused with a carbocyclic, heterocyclic, aromatic or heteroaromatic ring. Examples of heterocyclic radicals include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo [4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (O) moieties are pyrimidinonyl and 1,1-dioxo-thiomorpholinyl. The heterocycle groups herein are optionally substituted independently with one or more substituents as described herein.

The term "halogen" refers to —Br, —Cl, —I, and —F.

"Substituted alkyl", "substituted aryl", "substituted heterocyclyl", mean alkyl, aryl, heterocyclyl and carbocyclyl respectively, in which one or more hydrogen atoms are each independently replaced with a substituent. Typical substituents include, but are not limited to, X, R, O—, —OR, —SR, —NR2, —NR3, =NR, =N—OR, =O, —CX3, —CN, —OCN, —SCN, —N=C=O, —NCS, —NO, —NO2, =N2, —N3, NC(=O)R, —C(=O)R, —C(=O)NR2, —SO3-, —SO3H, —S(=O)2R, —OS(=O)2OR, —S(=O)2NR, —S(=O)R, —OP(=O)(OR)2, —P(=O)(OR)2, —PO3, —PO3H2, —C(=O)R, —C(=O)X, —C(=S)R, —CO2R, —CO2-, —C(=S)OR, —C(=O)SR, —C(=S) SR, —C(=O)NR2, —C(=S)NR2, and —C(=NR)NR2, where each X is independently a halogen (F, Cl, Br, or I), and each R is independently H, C1-C18 alkyl, C6-C20 aryl, C3-C14 heterocycle, protecting group or prodrug moiety. Alkylene, alkenylene, and alkynylene groups as described above may also be similarly substituted.

TABLE 1

Examples of Type III Secretion Inhibitors (Antibiotic Molecules)

| Structure | Constituents |
|---|---|
| 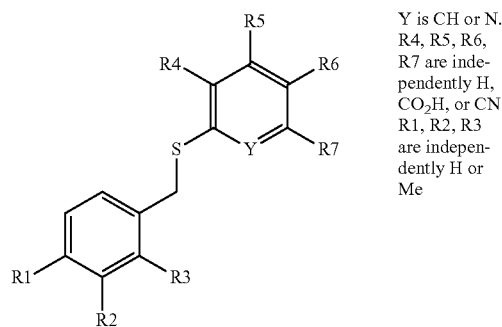 | Y is CH or N. R4, R5, R6, R7 are independently H, CO₂H, or CN R1, R2, R3 are independently H or Me |

TABLE 1-continued
Examples of Type III Secretion Inhibitors (Antibiotic Molecules)
| Structure | Constituents |
|---|---|
| 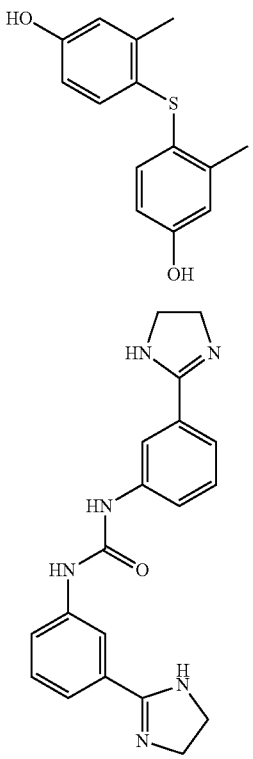 | |
| 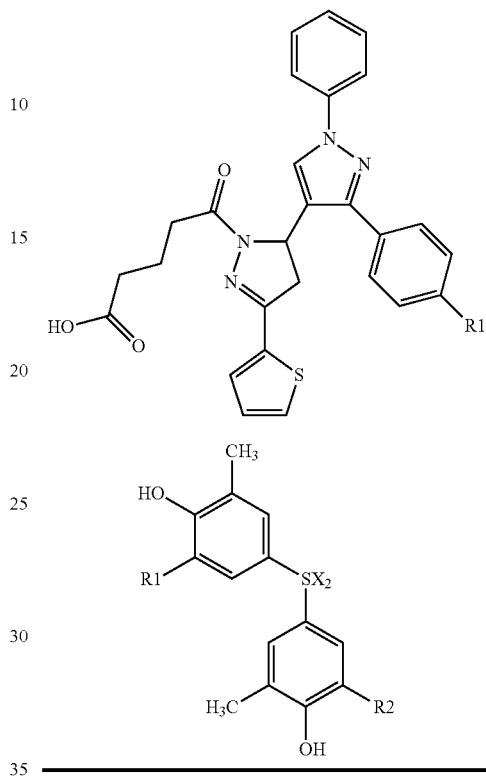 | R1 is H, Me or OMe |
| 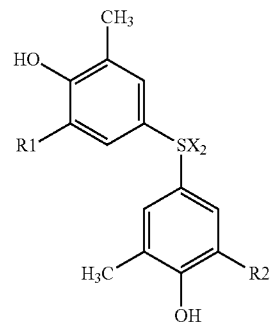 | X is absent or O<br>R1 and R2 are independently H or tert-butyl |
TABLE 2
Commercially Available T3S Inhibitor Analogs
| Structure | Sample ID | Source/Available Compound |
|---|---|---|
| 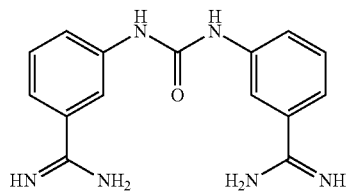 [SMILES: N=C(N)c1cccc(NC(=O)Nc2cccc(C(=N)N)c2)c1] | 3-1 | Tim Tec |
| 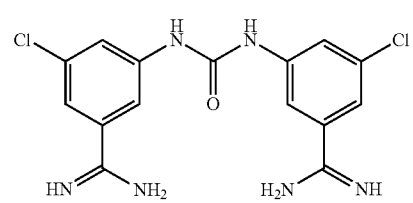 [SMILES: N=C(N)c1cc(Cl)cc(NC(=O)Nc2cc(Cl)cc(C(=N)N)c2)c1] | 3-2 | |

TABLE 2-continued

Commercially Available T3S Inhibitor Analogs

| Structure | Sample ID | Source/Available Compound |
|---|---|---|
| 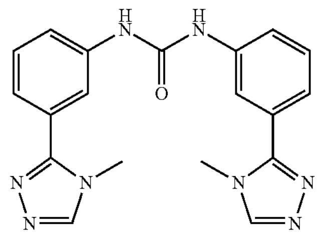 [SMILES: Cn1cnnc1-c1cccc(NC(=O)Nc2cccc(-c3nncn3C)c2)c1] | 3-3 | Scientific Exchange |
| 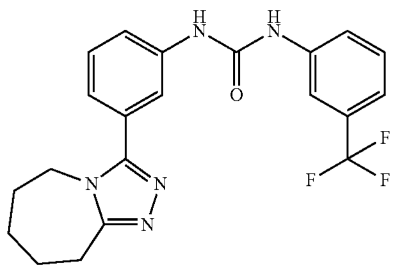 [SMILES: O=C(Nc1cccc(-c2nnc3n2CCCCC3)c1)Nc1cccc(C(F)(F)F)c1] | 3-4 | Enamine |
| 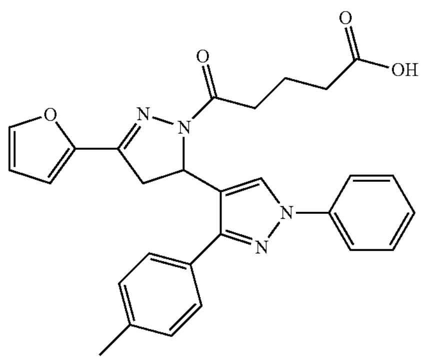 [SMILES: Cc1ccc(-c2nn(-c3ccccc3)cc2C2CC(c3ccco3)=NN2C(=O)CCCC(=O)O)cc1] | 4-3 | Enamine |
| 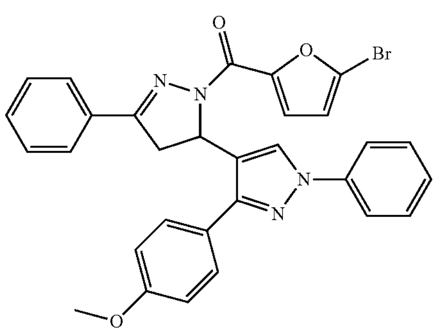 [SMILES: COc1ccc(-c2nn(-c3ccccc3)cc2C2CC(c3ccccc3)=NN2C(=O)c2ccc(Br)o2)cc1] | 4-4 | Enamine |
| 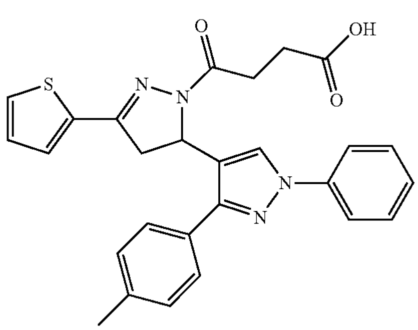 [SMILES: Cc1ccc(-c2nn(-c3ccccc3)cc2C2CC(c3cccs3)=NN2C(=O)CCC(=O)O)cc1] | 4-5 | Analogix |

TABLE 2-continued

Commercially Available T3S Inhibitor Analogs

| Structure | Sample ID | Source/Available Compound |
|---|---|---|
| 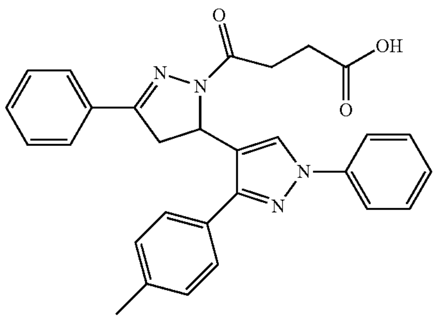 [SMILES: Cc1ccc(-c2nn(-c3ccccc3)cc2C2CC(c3ccccc3)=NN2C(=O)CCC(=O)O)cc1] | 4-6 | Analogix |
| 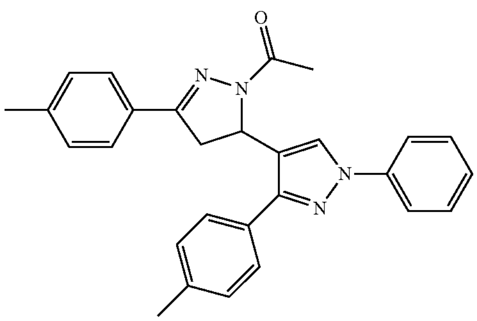 [SMILES: CC(=O)N1N=C(c2ccc(C)cc2)CC1c1cn(-c2ccccc2)nc1-c1ccc(C)cc1] | 4-7 | Enamine |
| 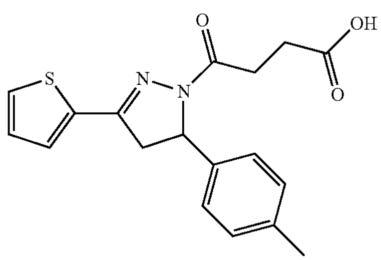 [SMILES: Cc1ccc(C2CC(c3cccs3)=NN2C(=O)CCC(=O)O)cc1] | 4-8 | Analogix |
| 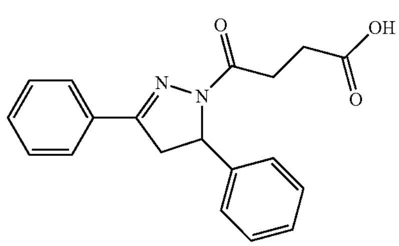 [SMILES: O=C(O)CCC(=O)N1N=C(c2ccccc2)CC1c1ccccc1] | 4-9 | Enamine |

TABLE 2-continued

Commercially Available T3S Inhibitor Analogs

| Structure | Sample ID | Source/Available Compound |
|---|---|---|
| 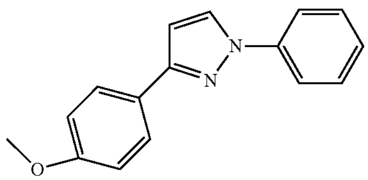 [SMILES: COc1ccc(-c2ccn(-c3ccccc3)n2)cc1] | 4-11 | Chembridge |
| 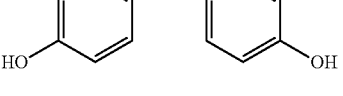 | 2-3 | Sigma-Aldrich |
| 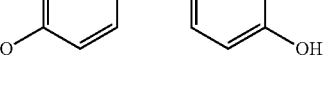 | 2-4 | Chembridge |
|  | 3-5 | Sigma-Aldrich |
|  | 3-6 | TimTec |

Note:
Sample ID indicates "Compound#"-"Analog#" (e.g., 3-1 denotes analog 1 of compound 3)

TABLE 3

Compound 1 Analogs—First round of Medicinal Chemistry.

| ID | X | MW | comment | Sample ID |
|---|---|---|---|---|
| 3-71-1 | 4-Cl | 304.8 | | MC1_1-1 |
| 3-71-2 | 4-H | 270.3 | | MC1_1-2 |
| 3-71-3 | 4-OMe | 300.3 | | MC1_1-3 |
| 3-71-4 | 3-NO$_2$ | 315.3 | | MC1_1-4 |
| 3-71-5 | 2-Cl | 304.8 | | MC1_1-5 |
| 3-71-6 | 3-Me | 284.3 | | MC1_1-6 |
| 3-71-7 | 4-Me | 284.3 | Lead 1 | MC1_1-7 |
| 3-71-8 | 4-CF$_3$ | 338.3 | | MC1_1-8 |
| 3-71-9 | 4-OCF$_3$ | 354.3 | | MC1_1-9 |

TABLE 4

Compound 1 Analogs—Second round of Medicinal Chemistry.

| ID | Structure | Sample ID |
|---|---|---|
| 3-78-1 | isopropyl-S- | MC1_2-1 |
| 3-78-2 | cyclohexyl-S- | MC1_2-2 |
| 3-78-3 | 4-chlorophenyl-S- | MC1_2-3 |

TABLE 4-continued

Compound 1 Analogs—Second round of Medicinal Chemistry.

| ID | Structure | Sample ID |
|---|---|---|
| 3-83-1 | HO–(CH2)3–NH– | MC1_2-4 |
| 3-83-2 | Et2N– | MC1_2-5 |
| 3-83-3 | 4-(EtO2C)-piperidin-1-yl | MC1_2-6 |
| 3-83-4 | 2-(CO2Et)-piperidin-1-yl | MC1_2-7 |
| 3-83-5 | isopentyl-NH– | MC1_2-8 |
| 3-83-6 | isobutyl-NH– | MC1_2-9 |
| 3-83-7 | iPr-NH– | MC1_2-10 |
| 3-83-8 | 4-methylpiperazin-1-yl | MC1_2-11 |
| 3-83-9 | MeO-CH2CH2-NH– | MC1_2-12 |
| 3-83-10 | HO-(CH2)3-NH– | MC1_2-13 |
| 3-83-11 | morpholin-4-yl | MC1_2-14 |
| 3-83-12 | piperidin-1-yl | MC1_2-15 |
| 3-83-13 | pyrrolidin-1-yl | MC1_2-16 |
| 3-83-14 | PhCH2-NH– | MC1_2-17 |
| 3-83-15 | PhCH2-N(Me)– | MC1_2-18 |
| 3-83-16 | 4-Cl-C6H4-CH2CH2-NH– | MC1_2-19 |

TABLE 5

Compound 1 Analogs—Third round of Medicinal Chemistry.

| ID | Structure | Sample ID |
|---|---|---|
| 3-97 | 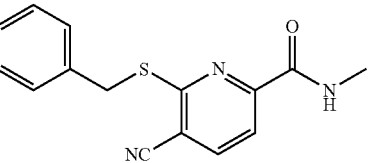 | MC1_3-1 |

TABLE 5-continued

Compound 1 Analogs—Third round of Medicinal Chemistry.

| ID | Structure | Sample ID |
|---|---|---|
| 3-98 | methyl 6-((4-chlorobenzyl)thio)-5-cyanopicolinate | MC1_3-2 |
| 3-99 | 6-((4-chlorobenzyl)thio)-5-cyanopicolinamide | MC1_3-3 |

TABLE 6

Compound 3 Analogs—First round of Medicinal Chemistry.

| ID | Structure | Salt | FW | Sample ID |
|---|---|---|---|---|
| 2-147-1 | 1-(4-ethoxyphenyl)-3-(3-(4,5-dihydro-1H-imidazol-2-yl)phenyl)urea | HCl salt | 360.8 | MC3_1-1 |
| 2-147-2 | 1-(3-nitrophenyl)-3-(3-(4,5-dihydro-1H-imidazol-2-yl)phenyl)urea | HCl salt | 361.8 | MC3_1-2 |
| 2-147-3 | 1-(3-cyanophenyl)-3-(3-(4,5-dihydro-1H-imidazol-2-yl)phenyl)urea | HCl salt | 341.8 | MC3_1-3 |
| 2-147-4 | methyl 3-(3-(3-(4,5-dihydro-1H-imidazol-2-yl)phenyl)ureido)benzoate | HCl salt | 374.8 | MC3_1-4 |
| 2-147-5 | 1-(benzo[d][1,3]dioxol-5-yl)-3-(3-(4,5-dihydro-1H-imidazol-2-yl)phenyl)urea | HCl salt | 360.8 | MC3_1-5 |

TABLE 6-continued

Compound 3 Analogs—First round of Medicinal Chemistry.

| ID | Structure | Salt | FW | Sample ID |
|---|---|---|---|---|
| 2-147-6 | 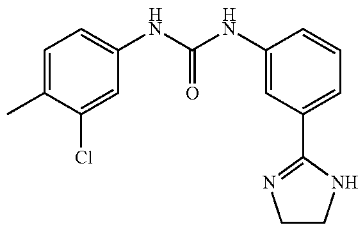 [SMILES: Cc1ccc(NC(=O)Nc2cccc(C3=NCCN3)c2)cc1Cl] | HCl salt | 365.3 | MC3_1-6 |
| 2-147-7 | 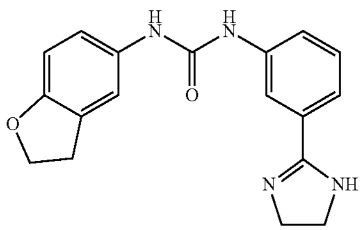 [SMILES: O=C(Nc1cccc(C2=NCCN2)c1)Nc1ccc2c(c1)CCO2] | HCl salt | 358.8 | MC3_1-7 |
| 2-147-8 | 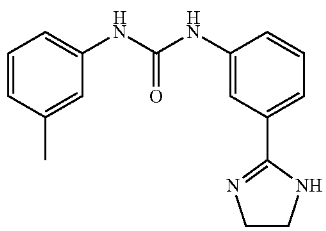 [SMILES: Cc1cccc(NC(=O)Nc2cccc(C3=NCCN3)c2)c1] | HCl salt | 330.8 | MC3_1-8 |
| 2-147-9 | 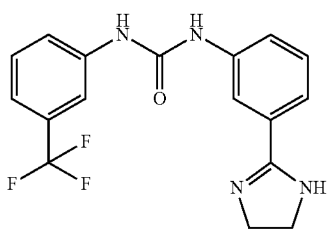 [SMILES: O=C(Nc1cccc(C2=NCCN2)c1)Nc1cccc(C(F)(F)F)c1] | HCl salt | 384.8 | MC3_1-9 |
| 2-147-10 | 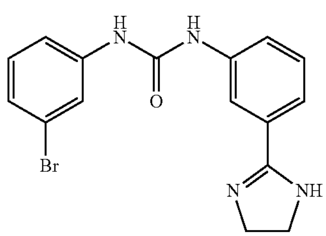 [SMILES: O=C(Nc1cccc(Br)c1)Nc1cccc(C2=NCCN2)c1] | HCl salt | 395.7 | MC3_1-10 |
| 2-147-11 | 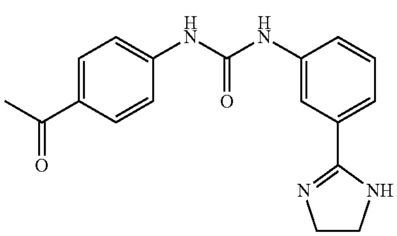 [SMILES: CC(=O)c1ccc(NC(=O)Nc2cccc(C3=NCCN3)c2)cc1] | HCl salt | 358.8 | MC3_1-11 |
| 2-145-1 | 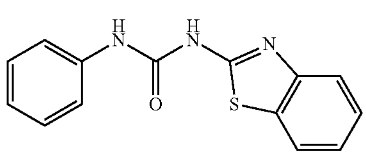 [SMILES: O=C(Nc1ccccc1)Nc1nc2ccccc2s1] | | 269.3 | MC3_1-12 |

TABLE 6-continued
Compound 3 Analogs—First round of Medicinal Chemistry.
| ID | Structure | Salt | FW | Sample ID |
|---|---|---|---|---|
| 2-145-2 | 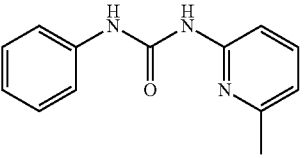 [SMILES: Cc1cccc(NC(=O)Nc2ccccc2)n1] | | 227.3 | MC3_1-13 |
| 2-145-3 | 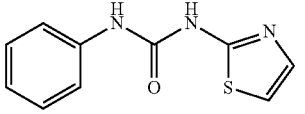 [SMILES: O=C(Nc1ccccc1)Nc1nccs1] | | 219.3 | MC3_1-14 |
| 2-146-1 | 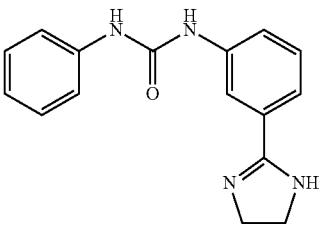 [SMILES: O=C(Nc1ccccc1)Nc1cccc(C2=NCCN2)c1] | HCl salt | 316.8 | MC3_1-15 |
| 2-146-2 | 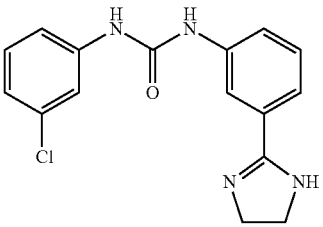 [SMILES: O=C(Nc1cccc(Cl)c1)Nc1cccc(C2=NCCN2)c1] | HCl salt | 351.2 | MC3_1-16 |
| 2-146-3 | 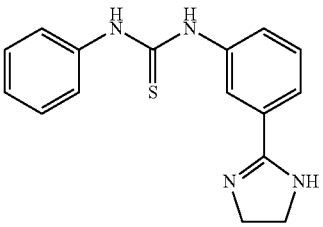 [SMILES: S=C(Nc1ccccc1)Nc1cccc(C2=NCCN2)c1] | HCl salt | 332.9 | MC3_1-17 |

TABLE 7

Compound 3 Analogs—Second round of Medicinal Chemistry.

| ID | Structure | FW | Sample ID |
|---|---|---|---|
| 3-64-1 | 4-EtO$_2$C-phenyl | 388.8 | MC3_2-1 |
| 3-64-2 | 4-Br-phenyl | 395.7 | MC3_2-2 |
| 3-64-3 | 2,5-diCl-phenyl | 385.7 | MC3_2-3 |
| 3-64-4 | 2,4-diCl-phenyl | 385.7 | MC3_2-4 |
| 3-64-5 | 2-Cl-phenyl | 351.2 | MC3_2-5 |
| 3-64-6 | 2-NO$_2$-phenyl | 361.8 | MC3_2-6 |
| 3-64-7 | 4-NO$_2$-phenyl | 361.8 | MC3_2-7 |
| 3-64-9 | 3,5-bis(CF$_3$)-phenyl | 452.8 | MC3_2-8 |
| 3-64-10 | 2-Cl-5-CF$_3$-phenyl | 419.2 | MC3_2-9 |
| 3-64-11 | 4-Cl-3-CF$_3$-phenyl | 419.2 | MC3_2-10 |
| 3-64-13 | 4-NC-phenyl | 341.8 | MC3_2-11 |
| 3-64-15 | 2-MeO-phenyl | 346.8 | MC3_2-12 |
| 3-64-16 | 2,4-diF-phenyl | 352.8 | MC3_2-13 |
| 3-64-17 | 2-Me-phenyl | 330.8 | MC3_2-14 |

TABLE 8

Compound 3 Analogs—Third round of Medicinal Chemistry.

| ID | Structure | Sample ID |
|---|---|---|
| 3-92 | [structure: 4-chloro-3-(trifluoromethyl)phenyl-NH-benzoxazole with imidazoline] | MC3_3-1 |
| 3-93 | [structure: 4-chloro-3-(trifluoromethyl)phenyl-NH-benzoxazole with tetrahydropyrimidine] | MC3_3-2 |
| 3-100 | [structure: regioisomer of 3-92] | MC3_3-3 |
| 3-101 | [structure: benzimidazole analog] | MC3_3-4 |

Note:
Sample ID in tables 3 through 8, indicates "Compound#"_"Round#"_"Analog#" and MC indicates "Medicinal Chemistry". (e.g., MC1_1-1 denotes compound 1, medicinal chemistry round 1, analog 1).

Gram-Negative Bacteria (Pathogens) and Associated Diseases

A diverse variety of gram-negative pathogens use type III secretion as a virulence mechanism. The following is a non-limiting list of such pathogenic organisms: *Yersinia* species (*Y. pestis, Y. enterocolitica, Y. pseudotuberculosis*); *Salmonella enterica* serovars (*Typhimurium, Typhi, Paratypi, Sendai, Dublin*, and *Choleraesuis*); Enteropathic (EPEC) and Enterohemorragic (EHEC) *E. coli*; *Shigella* species (*S. dysenteriae, S. flexneri, S. boydii*, and *S. sonnei* [multiple serotypes]); *Bordetella* species (*B. pertussis, B. parapertussis*, and *B. bronchiseptica*); *Pseudomonas aeruginosa; Burkholderia pseudomallei, Vibrio parahaemolyticus; V. cholerae*; and *Chlamydia* species (*C. trachomatis, C. pneumoniae*, and *C. psittaci*). The methods described herein are useful to identify inhibitors of pathogens using type III secretion as a virulence mechanism including, but not limited to, all of the aforementioned pathogens.

Gram-negative pathogens that use type III secretion as a virulence mechanism cause a diverse repertoire of diseases/ailments. For example, *Yersinia* species cause plague (bubonic, pneumonic, and septicemic) (*Y. pestis*), enterocolitis and mesenteric lymphadenitis (*Y. enterocolitica* and *Y. pseudotuberculosis*). *Salmonella enterica* serovars cause enterocolitis in humans and typhlitis and typhoid-like disease in mice (serovar *Typhimurium*), enteric fever in humans (serovars *Typhi, Paratyphi*, and *Sendai*), intestinal inflammation and bacteremia in cows (serovar *Dublin*), septicemia in pigs (serovar *Choleraesuis*). *E. coli* cause intestinal inflammation and bloody diarrhea (EPEC/EHEC), possibility of renal failure and septic shock (EHEC). *Shigella* species cause bacillary dysentery (shigellosis), sporadic dysentery pandemics (*S. dysenteriae*). *Bordetella* species cause whooping cough (*B. pertussis* and *B. parapertussis* [milder with *B. parapertussis*]), kennel cough in dogs, atrophic rhinitis in swine, possible respiratory illness in humans (*B. bronchiseptica*). *Pseudomonas aeruginosa* cause pneumonia (common cause of hospital-acquired pneumonia and occasionally of community-acquired pneumonia), chronic airway infection in cystic fibrosis, urinary tract infections in long-term care facilities, and various other clinical infections (e.g., endocarditis) in immuno-compromised patients. *Burkholderia pseudomallei* cause melioidosis, community-acquired bacteremias and pneumonias. *Vibrio* species cause noninflammatory secretory diarrhea (*V. cholerae*), inflammatory diarrhea with potential systemic spread (*V. parahaemolyticus*). *Chlamydia* species cause sexually transmitted infection (*C. trachomatis*), pneumonia (*C. pneumoniae*), psittacosis in birds (*C. psittaci*). The methods described herein are useful for treating and/or preventing diseases/ailments caused by bacteria (pathogens) using type III secretion as a virulence mechanism including, but not limited to, all of the aforementioned diseases/ailments.

Antibiotics as Anti-Biowarfare Agents:

In one embodiment, the present invention is useful in combating biological warfare agents (weapons). The CDC has three categories for biological warfare agents with category A, biological warfare agents, the most serious. These high-priority Category A agents include organisms that comprise a Type III secretion system (e.g., *Yersinia pestis*). Such agents can be easily disseminated (e.g., via infected fleas) or transmitted person-to-person, and can cause high mortality with the potential for major public health impact.

In general, the antibiotics of the present invention (e.g., compositions comprising one or more of the compounds in Table 1-8, 11 or 12) can be administered to a subject (individual) prior to or after suspected exposure to a biowarfare associated pathogen (a biowarfare agent) to prevent infection, or to decrease an already existing infection, caused by the pathogen. For example, the composition may be used as a treatment to heighten the ability to resist infection (prevent infection) for individuals working in situations with a higher than usual risk of exposure to harmful bacteria (e.g., biowarfare agents such as *Yersinia pestis*), such as health workers or military personnel (e.g., soldiers) operating in an active biological warfare environment.

Pharmaceutical/Veterinary Compositions, Formulations, and Administration

One aspect of the invention is treatment of a subject having or at risk of being infected with a gram-negative pathogen comprising a Type III secretion system with one or more of the antibiotic molecules disclosed herein, e.g. in Tables 1-8, 11 and 12, or with a pharmaceuticals composition comprising one or more of the antibiotic molecules disclosed herein. As used herein, a subject (patient) is a mammal, including but not limited to a dog, cat, horse, cow, pig, sheep, goat, chicken, rodent, or primate. Subjects can be house pets (e.g., dogs, cats), agricultural stock animals (e.g., cows, horses, pigs, chickens, etc.), laboratory animals (e.g., mice, rats, rabbits, etc.), zoo animals (e.g., lions, giraffes, etc.), but are not so limited. In some embodiments, preferred subjects are human subjects. The human subject may be a pediatric, adult or a geriatric subject.

As used herein treatment, or treating, includes amelioration, cure or maintenance (i.e., the prevention of relapse/recurrence) of a disease and/or infection. In one embodiment, a treatment decreases the virulence of a pathogenic organism in a subject. In one embodiment, a treatment inhibits a type III secretion system in a pathogenic organism. Treatment after a disease (infection) has started aims to reduce, ameliorate or altogether eliminate the disease (infection), and/or its associated symptoms, to prevent it from becoming worse, or to prevent the disease (infection) from re-occurring once it has been initially eliminated (i.e., to prevent a relapse/recurrence). Treatment before a disease (infection) has started aims to reduce the likelihood that the disease (infection), and/or its associated symptoms, will develop in the subject (to have a prophylactic effect).

Virulence, as used herein, refers to the degree of pathogenicity of an organism (e.g., a bacterium) to a host organism. Virulence functions (mechanisms) refer to properties (e.g., Type III secretion systems) of a pathogenic organism that cause a pathogenic effect in a host organism. "Decreasing the virulence" as used herein is defined as the ability of a compound (or composition) to attenuate, diminish, reduce, suppress, or arrest the development of, or the progression of disease and/or infection, in a host organism mediated by a pathogen.

In the preparation of pharmaceutical compositions, antibiotic molecules of the invention may be admixed with a pharmaceutically acceptable carrier suitable for administration to a subject (patient). Such a pharmaceutical composition may be administered to a subject (patient) to treat infection of a gram-negative pathogen comprising a Type III secretion system. The composition ultimately kills the pathogen(s) and/or blocks one or more virulence properties (e.g., a Type III Secretion System) and retards its pathogenic activity in the treatment of the infection.

A method of treating a mammalian bacterial infection involves administering to an infected mammal (e.g., a human) an effective amount (e.g., effective at blocking infection of a pathogen) of a compound, also referred to as an antibiotic compound, disclosed herein and/or identified by the methods disclosed herein. The method is useful in the treatment of infection, e.g., such as infection caused by a gram negative bacterium comprising a Type III secretion system, among the pathogenic organisms recited herein.

According to this invention, a pharmaceutical or veterinary composition as described herein is administered by any appropriate route. Preferably the route transmits the identified or designed compound directly into the blood, e.g., intravenous injection. Other routes of administration include, without limitation, oral, topical, intradermal, transdermal, intraperitoneal, intramuscular, intrathecal, subcutaneous, mucosal (e.g., intranasal), and by inhalation. One of skill in the art may also readily select a route of administration that is suitable to the infection site. Some specific examples include, without limitation, a topical solution, creme or ointment for application to a local bacterial infection on the skin, a solution or ointment suitable for application to a local bacterial infection of the eye, a solution or spray suitable for application to a bacterial infection of the throat or lung, and a solution suitable for application to a bacterial infection of the mucosa.

The amount of the antibiotic compound, selected using the methods herein, or disclosed herein, present in each effective dose (effective amount) is selected with regard to a variety of considerations. Among such considerations are the type of compound, the type and identity of bacteria (pathogen) causing the infection, the severity of infection, the location of the infection (e.g., systemic or localized), the type of subject (e.g., a human), the subject's age, weight, sex, general physical condition and the like. The amount of active component required to induce an effective effect (e.g., inhibit virulence of the bacteria) without significant adverse side effects varies depending upon the compound and pharmaceutical or veterinary composition employed and the optional presence of other components. Dosages of the compounds disclosed herein are readily determined by one skilled in the pharmaceutical arts.

Initial doses of the compounds of this invention are optionally followed by repeated administration for a duration selected by the attending physician (veterinarian). Dosage frequency depends upon the factors identified above. As one example, dosage ranges from 1 to 6 doses per day for a duration of about 3 days to a maximum of more than about 1 week. Other appropriate dosage protocols art known by the skilled artisan.

The amount of a treatment may be varied for example by increasing or decreasing the amount of T3S inhibitor or pharmacological agent or a therapeutic composition, by changing the therapeutic composition administered, by changing the route of administration, by changing the dosage timing and so on. The effective amount will vary with the particular infection or condition being treated, the age and physical condition of the subject being treated, the severity of the infection or condition, the duration of the treatment, the nature of the concurrent therapy (if any), the specific route of administration, and like factors are within the knowledge and expertise of the health practitioner. For example, an effective amount can depend upon the degree to which an individual has been exposed to or affected by exposure to the infection.

An effective amount is a dosage of the therapeutic agent (e.g., antibiotic compound) sufficient to provide a medically desirable result. It should be understood that the therapeutic agents of the invention are used to treat or prevent infections, that is, they may be used prophylactically in subjects at risk of developing an infection. Thus, an effective amount is that amount which can lower the risk of, slow or perhaps prevent altogether the development of an infection. It will be recognized when the therapeutic agent is used in acute circumstances, it is used to prevent one or more medically undesirable results that typically flow from such adverse events.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to treat the disorder, such as an infection. In the case of infections the desired response is inhibiting the progression of the infection. This may involve only slowing the progression of the infection temporarily, although more preferably, it involves halting the progression of the infection permanently. This can be monitored by routine diagnostic methods known to those of ordinary skill in the art. The desired response to treatment of the infection also can be delaying the onset or even preventing the onset of the infection.

The pharmacological agents used in the methods of the invention are preferably sterile and contain an effective amount of T3S inhibitor for producing the desired response in a unit of weight or volume suitable for administration to a subject. The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent may be adjusted by the individual physician or veterinarian, particularly in the event of any complication. A therapeutically effective amount typically varies from 0.01 mg/kg to about 1000 mg/kg subject body weight, in one or more dose administrations daily, for one or more days. In one embodiment a therapeutically effective amount varies from about 0.1 mg/kg to about 200 mg/kg subject body weight, in one or more dose administrations daily, for one or more days. In one embodiment a therapeutically effective amount varies from about 0.2 mg/kg to about 20 mg/kg subject body weight, in one or more dose administrations daily, for one or more days.

The pharmaceutical or veterinary compositions are formulated to suit a selected route of administration, and may contain ingredients specific to the route of administration. Various modes of administration are known to those of ordinary skill in the art which effectively deliver the pharmacological agents of the invention to a desired tissue, cell, or bodily fluid. The administration methods are discussed elsewhere in the application. The invention is not limited by the particular modes of administration disclosed herein. Standard references in the art (e.g., Remington's Pharmaceutical Sciences, 20th Edition, Lippincott, Williams and Wilkins, Baltimore Md., 2001) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical or veterinary compositions of the present invention may contain a pharmaceutically acceptable carrier or excipient suitable for rendering the compound or mixture administrable orally as a tablet, capsule or pill, or parenterally, intravenously, intradermally, intramuscularly or subcutaneously, or transdermally. The active ingredients may be admixed or compounded with any conventional, pharmaceutically acceptable carrier or excipient.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride; chlorobutanol; parabens and thimerosal.

The preparation of pharmaceutically acceptable compositions, from the components disclosed herein, having appropriate pH isotonicity, stability and other conventional characteristics is within the skill of the art.

Pharmaceutical or veterinary compositions of this invention contain effective amounts of antibiotic compounds in conventional pharmaceutically acceptable (e.g., physiologically acceptable carriers). Exemplary pharmaceutically acceptable carriers that are suitable for use in a composition of the invention are well known to those of skill in the art and are disclosed herein. Such carriers include, for example, saline, phosphate buffered saline, oil-in-water emulsions and others. The present invention is not limited by the selection of the carrier. Similarly other active agents, such as other anti-pathogenic molecules, antiviral compounds or conventional antibiotics, such as vancomycin [see, e.g., International Patent Publication No. WO98/40401, published Mar. 10, 1998, incorporated by reference herein] can be combined with antibiotic components of the pharmaceutical or veterinary compositions of this invention. Other exemplary anti-pathogenic molecules, conventional antibiotics or antiviral compounds are known in the art and disclosed in US 2006-0009386 A1, the contents of which are incorporated herein by reference in its entirety.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, pills, lozenges, each containing a predetermined amount of the active compound (e.g., T3S inhibitor). Other compositions include suspensions in aqueous liquids or non-aqueous liquids such as a syrup, elixir, an emulsion, or a gel.

Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers, i.e. EDTA for neutralizing internal acid conditions or may be administered without any carriers.

Also specifically contemplated are oral dosage forms of the above component or components. The component or components may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline. Abuchowski and Davis, 1981, "Soluble Polymer-Enzyme Adducts" In: Enzymes as Drugs, Hocenberg and Roberts, eds., Wiley-Interscience, New York, N.Y., pp. 367-383; Newmark, et al., 1982, J. Appl. Biochem. 4:185-189. Other polymers that could be used are poly-1,3-dioxolane and poly-1,3,6-tioxocane. Preferred for pharmaceutical usage, as indicated above, are polyethylene glycol moieties.

For the component (or derivative) the location of release may be the stomach, the small intestine (the duodenum, the jejunum, or the ileum), or the large intestine. One skilled in the art has available formulations which will not dissolve in the stomach, yet will release the material in the duodenum or elsewhere in the intestine. Preferably, the release will avoid the deleterious effects of the stomach environment, either by protection of T3S inhibitor or by release of the biologically active material beyond the stomach environment, such as in the intestine.

To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D, Aquateric, cellulose acetate phthalate (CAP), Eudragit L, Eudragit S, and Shellac. These coatings may be used as mixed films.

A coating or mixture of coatings can also be used on tablets, which are not intended for protection against the stomach. This can include sugar coatings, or coatings which make the tablet easier to swallow. Capsules may consist of a hard shell (such as gelatin) for delivery of dry therapeutic i.e. powder; for liquid forms, a soft gelatin shell may be used. The shell material of cachets could be thick starch or other edible paper. For pills, lozenges, molded tablets or tablet triturates, moist massing techniques can be used.

The therapeutic can be included in the formulation as fine multi particulates in the form of granules or pellets of particle size about 1 mm. The formulation of the material for capsule administration could also be as a powder, lightly compressed plugs or even as tablets. The therapeutic could be prepared by compression.

Colorants and flavoring agents may all be included. For example, T3S inhibitor may be formulated (such as by liposome or microsphere encapsulation) and then further contained within an edible product, such as a refrigerated beverage containing colorants and flavoring agents.

One may dilute or increase the volume of the therapeutic with an inert material. These diluents could include carbohydrates, especially mannitol, a lactose, anhydrous lactose, cellulose, sucrose, modified dextrans and starch. Certain inorganic salts may be also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the therapeutic into a solid dosage form. Materials used as disintegrants include but are not limited to starch, including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants are the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the therapeutic agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the therapeutic.

An anti frictional agent may be included in the formulation of the therapeutic to prevent sticking during the formulation process. Lubricants may be used as a layer between the therapeutic and the die wall, and these can include but are not limited to; stearic acid including its magnesium and calcium salts, polytetrafluoroethylene (PTFE), liquid paraffin, vegetable oils and waxes. Soluble lubricants may also be used such as sodium lauryl sulfate, magnesium lauryl sulfate, polyethylene glycol of various molecular weights, Carbowax 4000 and 6000.

Glidants that might improve the flow properties of the drug during formulation and to aid rearrangement during compression might be added. The glidants may include starch, talc, pyrogenic silica and hydrated silicoaluminate.

To aid dissolution of the therapeutic into the aqueous environment a surfactant might be added as a wetting agent. Surfactants may include anionic detergents such as sodium lauryl sulfate, dioctyl sodium sulfosuccinate and dioctyl sodium sulfonate. Cationic detergents might be used and could include benzalkonium chloride or benzethomium chloride. The list of potential non ionic detergents that could be included in the formulation as surfactants are lauromacrogol 400, polyoxyl 40 stearate, polyoxyethylene hydrogenated castor oil 10, 50 and 60, glycerol monostearate, polysorbate 40, 60, 65 and 80, sucrose fatty acid ester, methyl cellulose and carboxymethyl cellulose. These surfactants could be present in the formulation of T3S inhibitor either alone or as a mixture in different ratios.

Pharmaceutical preparations which can be used orally include push fit capsules made of gelatin, as well as soft, sealed capsules made of gelatin and a plasticizer, such as glycerol or sorbitol. The push fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

Also contemplated herein is pulmonary delivery of T3S inhibitor. T3S inhibitor is delivered to the lungs of a mammal while inhaling and traverses across the lung epithelial lining to the blood stream. Other reports of inhaled molecules include Adjei et al., 1990, Pharmaceutical Research, 7:565 569; Adjei et al., 1990, International Journal of Pharmaceutics, 63:135 144 (leuprolide acetate); Braquet et al., 1989, Journal of Cardiovascular Pharmacology, 13(suppl. 5):143 146 (endothelin-1); Hubbard et al., 1989, Annals of Internal Medicine, Vol. III, pp. 206 212 (a1 antitrypsin); Smith et al., 1989, J. Clin. Invest. 84:1145-1146 (a 1-proteinase); Oswein et al., 1990, "Aerosolization of Proteins", Proceedings of Symposium on Respiratory Drug Delivery II, Keystone, Colo., March, (recombinant human growth hormone); Debs et al., 1988, J. Immunol. 140:3482 3488 (interferon γ and tumor necrosis factor alpha) and Platz et al., U.S. Pat. No. 5,284,656 (granulocyte colony stimulating factor). A method and composition for pulmonary delivery of drugs for systemic effect is described in U.S. Pat. No. 5,451,569, issued Sep. 19, 1995 to Wong et al.

Contemplated for use in the practice of this invention are a wide range of mechanical devices designed for pulmonary delivery of therapeutic products, including but not limited to nebulizers, metered dose inhalers, and powder inhalers, all of which are familiar to those skilled in the art.

Some specific examples of commercially available devices suitable for the practice of this invention are the Ultravent nebulizer, manufactured by Mallinckrodt, Inc., St. Louis, Mo.; the Acorn II nebulizer, manufactured by Marquest Medical Products, Englewood, Colo.; the Ventolin metered dose inhaler, manufactured by Glaxo Inc., Research Triangle Park, North Carolina; and the Spinhaler powder inhaler, manufactured by Fisons Corp., Bedford, Mass.

All such devices require the use of formulations suitable for the dispensing of T3S inhibitor. Typically, each formulation is specific to the type of device employed and may involve the use of an appropriate propellant material, in addition to the usual diluents, adjuvants and/or carriers useful in therapy. Also, the use of liposomes, microcapsules or microspheres, inclusion complexes, or other types of carriers is contemplated. Chemically modified T3S inhibitor may also be prepared in different formulations depending on the type of chemical modification or the type of device employed.

Formulations suitable for use with a nebulizer, either jet or ultrasonic, will typically comprise T3S inhibitor dissolved in water at a concentration of about 0.1 to 25 mg of biologically active T3S inhibitor per mL of solution. The formulation may also include a buffer and a simple sugar (e.g., for T3S inhibitor stabilization and regulation of osmotic pressure). The nebulizer formulation may also contain a surfactant, to reduce or prevent surface induced aggregation of the T3S inhibitor caused by atomization of the solution in forming the aerosol.

Formulations for use with a metered dose inhaler device will generally comprise a finely divided powder containing the T3S inhibitor suspended in a propellant with the aid of a surfactant. The propellant may be any conventional material employed for this purpose, such as a chlorofluorocarbon, a hydrochlorofluorocarbon, a hydrofluorocarbon, or a hydrocarbon, including trichlorofluoromethane, dichlorodifluoromethane, dichlorotetrafluoroethanol, and 1,1,1,2 tetrafluoroethane, or combinations thereof. Suitable surfactants include sorbitan trioleate and soya lecithin. Oleic acid may also be useful as a surfactant.

Formulations for dispensing from a powder inhaler device will comprise a finely divided dry powder containing T3S inhibitor and may also include a bulking agent, such as lactose, sorbitol, sucrose, or mannitol in amounts which facilitate dispersal of the powder from the device, e.g., 50 to 90% by weight of the formulation. The T3S inhibitor should most advantageously be prepared in particulate form with an average particle size of less than 10 mm (or microns), most preferably 0.5 to 5 mm, for most effective delivery to the distal lung.

Nasal (or intranasal) delivery of a pharmaceutical composition of the present invention is also contemplated. Nasal delivery allows the passage of a pharmaceutical composition of the present invention to the blood stream directly after administering the therapeutic product to the nose, without the necessity for deposition of the product in the lung. Formulations for nasal delivery include those with dextran or cyclodextran.

For nasal administration, a useful device is a small, hard bottle to which a metered dose sprayer is attached. In one embodiment, the metered dose is delivered by drawing the pharmaceutical composition of the present invention solution into a chamber of defined volume, which chamber has an aperture dimensioned to aerosolize and aerosol formulation by forming a spray when a liquid in the chamber is compressed. The chamber is compressed to administer the pharmaceutical composition of the present invention. In a specific embodiment, the chamber is a piston arrangement. Such devices are commercially available.

Alternatively, a plastic squeeze bottle with an aperture or opening dimensioned to aerosolize an aerosol formulation by forming a spray when squeezed is used. The opening is usually found in the top of the bottle, and the top is generally tapered to partially fit in the nasal passages for efficient administration of the aerosol formulation. Preferably, the nasal inhaler will provide a metered amount of the aerosol formulation, for administration of a measured dose of the drug.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active compounds may be in powder form for constitution with a suitable vehicle, e.g., sterile pyrogen-free water, before use.

The compounds may also be formulated in rectal or vaginal compositions such as suppositories or retention enemas, e.g., containing conventional suppository bases such as cocoa butter or other glycerides.

In addition to the formulations described previously, the compounds may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, Science 249:1527-1533, 1990, which is incorporated herein by reference.

T3S inhibitor and optionally other therapeutics may be administered per se or in the form of a pharmaceutically acceptable salt.

The therapeutic agent(s), including specifically but not limited to T3S inhibitor, may be provided in particles. Particles as used herein means nano or microparticles (or in some instances larger) which can consist in whole or in part of T3S inhibitor or the other therapeutic agent(s) as described herein.

The particles may contain the therapeutic agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the T3S inhibitor in a solution or in a semi-solid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in Macromolecules, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in controlled release systems. The term "controlled release" is intended to refer to any drug-containing formulation in which the manner and profile of drug release from the formulation are controlled. This refers to immediate as well as non-immediate release formulations, with non-immediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release."

Use of a long-term sustained release implant may be particularly suitable for treatment of chronic conditions. "Long-term" release, as used herein, means that the implant is constructed and arranged to deliver therapeutic levels of the active ingredient for at least 7 days, and preferably 30-60 days. Long-term sustained release implants are well-known to those of ordinary skill in the art and include some of the release systems described above.

The invention also contemplates the use of kits. In some aspects of the invention, the kit can include a pharmaceutical preparation vial, a pharmaceutical preparation diluent vial, and T3S inhibitor. The vial containing the diluent for the pharmaceutical preparation is optional. The diluent vial contains a diluent such as physiological saline for diluting what could be a concentrated solution or lyophilized powder of T3S inhibitor. The instructions can include instructions for mixing a particular amount of the diluent with a particular amount of the concentrated pharmaceutical preparation, whereby a final formulation for injection or infusion is prepared. The instructions may include instructions for treating a subject with an effective amount of T3S inhibitor. It also will be understood that the containers containing the preparations, whether the container is a bottle, a vial with a septum, an ampoule with a septum, an infusion bag, and the like, can contain indicia such as conventional markings which change color when the preparation has been autoclaved or otherwise sterilized.

The invention in some embodiments provides a pharmaceutical pack or kit comprising one or more containers filled with one or more of the ingredients of the pharmaceutical compositions of the invention. Associated with such container(s) can be various written materials (written information) such as instructions (indicia) for use, or a notice in the form prescribed by a governmental agency regulating the manufacture, use or sale of pharmaceuticals or biological products, which notice reflects approval by the agency of manufacture, use or sale for human administration (or administration to any of the subjects disclosed herein).

EXAMPLES

Example 1

Identification and Uses of Type III Secretion Inhibitors Materials and Methods

Bacterial Strains, Plasmids, and Growth Conditions

*Y. pestis* strains used in this study are driven from D122. The strains and the plasmids used are listed in Table 9. Plasmid pMM85 (YopE-Bla) was a gift from Dr. Olaf Schneewind in University of Chicago. *Y. pestis* and *Y. pseudotuberculosis* were cultured in TB broth [1% (w/v) Bacto tryptose (BD Bioscience), 0.5% (w/v) NaCl, 0.3% (w/v) beef extract (Fisher)] and brain-heart infusion (BHI, BD Bioscience) broth as indicated. For high throughput screening, *Y. pestis* was grown in TB for 20 hr at 26° C., diluted to $1 \times 10^4$ bacteria/ml, the screening compounds were applied, bacterial culture were then shifted to 37° C. and incubated for 18 hours. To monitor the secretion of Yops, *Yersinia* strains were grow in BHI at 30° C. overnight then subcultured to an optical density at 600 nm (OD600) of 0.04 in fresh BHI and incubated at 30° C. to OD600 of 0.2 then subjected to 2-hour 37° C. incubation. EPEC strains normally were cultured in LB media at 37° C., unless otherwise indicated.

Small Molecules and Antibodies

Compounds and extracts used in the HTS and cherry picks were provided by the US National Screening Laboratory at Harvard Medical School. Larger quantities of the testing compounds were obtained from commercial venders. Compounds 1, 2 and 3 were purchased from TimTec, Inc; compound 3 dipropionate was from Sigma-Aldrich; compound 4 and INP0007 were from ChemBridge Corporation. Mouse monoclonal anti-YopM Ab (1A1), rabbit polyclonal anti-YopD Ab (5331), and rabbit polyclonal anti-YopH Ab (G5788) were gifts from Dr. Sue Straley in University of Kentucky and were used in Western Blot (Western) experiments to detect the presence of specific Yops. A rabbit polyclonal anti-YopE Ab was a gift from Dr. Olaf Schneewind in University of Chicago. A mouse anti-HA (HA.11) was purchased from Covance, and rabbit anti-OmpA was kindly provided by Carol Kumamoto.

Producing Luminescence in *Y. pestis*

Plasmid pML001 carrying lux operon from *Photorhabdus luminescence* was introduced into *Y. pestis* to produce luminescence. A kanamycin resistant gene was introduced to the pCD1 plasmid by transposon mutagenesis to produce pCD1K. The plasmid(s) were transformed into D122 (pCD1−) to generate strain JG401 [D122 (pCD1K pML001)]. Plasmid pML001 above was transferred into D122 to generate strain JG406 [D122 (pML001)]. The luminescence of the bacterial culture was measured by a Packard Picolit™ luminometer (United Technologies) and an EnVision plate reader (PerkinElmer).

The High-Throughput Screening

The high-throughput screening (HTS) was conducted by using the luminescent *Y. pestis* JG401 strain. 30 µl of JG401 culture ($1 \times 10^4$ bacteria/ml) were added into each well of 384-well cell culture plates by using a liquid handling robot Bio-Tek µFill plate dispenser with Bio-Tek Bio-Stack (Bio-Tek Instruments). 100 nl of screening compound (5 mg/ml in DMSO) were applied to each well of the assay plates by using an Epson compound transfer robot with Epson standard volume pin arrays. The plates were incubated overnight at 37° C. The relative luminescence unit (RLU) was measured by using high throughput 40-plate stacker EnVision plate readers (PerkinElmer). Statistical analysis of the primary screening results was carried out as described previously.

Analysis of Effector Proteins from *Y. pestis* Cells and Cultural Supernatant

*Y. pestis* D122 and D122 (pCD1−) strains were used in this assay. Bacterial overnight culture in TB broth was subcultured into BHI broth to $OD_{600}$=0.04. The culture was then grown at 30° C. in flasks with shaking till $OD_{600}$=0.2. Different concentrations of the testing compounds were added to the bacterial cultures. The cultures were then shifted to 37° C. for T3S induction for 2 hours. The culture supernatants were collected after centrifugation. TCA precipitates of the culture supernatants were subjected to SDS-PAGE followed by Western blot for YopM, YopH, and YopD. The Western blots were stopped developing before positive Yop controls reach saturation, the intensity and area of each band were quantified by desitometry. Each secretion experiment was performed for at least 3 times. $IC_{50}$s were taken from the concentration dependent mean value curves.

Effect of Compounds on Bacterial Growth

Bacterial mid-log phase cultures were sub-cultured to OD600=0.05 in TB broth containing 2.5 mM calcium. 200 µl/well of the culture was added to FALCON® MICROTEST™ 96 well tissue culture plates (Becton Dickinson, catalog #353072). Final concentration of 0, 10, 20, 40, 60, and 80 µM testing compounds were added to the wells. The cultures were incubated in Spectra Max 250 (Molecular Devices, CA) at 37° C. with auto-mix, $OD_{600\ (200\mu l)}$ were measured at intervals. The raw data was recorded by SOFTmax® PRO and exported to Microsoft Excel. $OD_{600\ (200\mu l)}$ was converted to standard $OD_{600}$ ($cm^{-1}$) by using with equation 1, which was generated by measuring 10 different density cultural samples in both standard cuvettes and the 96-well plate.

Measuring Cytotoxicity of the Testing Compounds

HeLa cells were maintained in Dulbecco's modified Eagle's medium (DMEM, Invitrogen) supplemented with 10% heat inactivated fetal bovine serum (FBS), 100 units $ml^{-1}$ penicillin and 100 µg $ml^{-1}$ streptomycin at 37° C. with 5% $CO_2$. $1 \times 10^5$ HeLa cells well$^{-1}$ were seeded in 24-well tissue culture plate in DMEM with 3% heat inactivated FBS one day prior to the assay. Compounds were applied, and incubated at 37° C. for 3 hours. The disruption of the cell monolayer was recorded by measuring the percentage of cell detachment from the tissue culture plate. HeLa cell cultures were centrifuged. Lactate dehydrogenase (LDH) activity in the culture supernatant was measured by using Cytotoxicity Detection Kit (LDH) (Roche) as described in the manufacture protocol.

T3S Mediated Cytotoxic Response

HeLa cell monolayer were infected by *Y. pestis* in DMEM medium with 3% heat inactivated FBS and 24 µM HEPES pH 7.4 then incubated at 37° C. with 5% $CO_2$. Testing compounds were added to the cell cultures prior to the incubation. pCD1+ strain infected HeLa cells were cytotoxically affected, with a rounded-up morphology. The inhibition (%) of the cytotoxic response was calculated by comparing percentage of the Hela cells that showed the rounded-up morphology due to the effector translocations to the controls. A pCD1-strain, JG154, was used as a negative control.

Translocation of YopE-Bla Fusion Protein into HeLa Cells

HeLa cells were maintained as described above. One day prior to infection, $3.5\times10^4$ cells were seeded in 24-well plates. 2 hours before infection, cells were washed with phosphate buffered saline (PBS) and 350 μl of DMEM with 24 μM HEPES were added to each well. HeLa cells were infected with mid-log phase YopE-Bla (pMM85) contain *Y. pestis* strain at an MOI of 10 for 3 hours. 1× final concentration of CCF2-AM (Invitrogen) was added to live cells. The cells were incubated at room temperature for 1~2 hours then analyzed by fluorescence microscopy using a Nikon Eclipse E800 microscope with a beta-lactamase filter set (Chroma).

Tir Secretion in EPEC Culture

EPEC Type III Secretion assays were performed as described previously [Deng, 2005]. Briefly, bacterial cultures were grown in LB at 37° C. for approximately 8 hours, diluted 1:500 into pre-warmed DMEM/HEPES and grown in 5% $CO_2$ atmosphere overnight. Overnight cultures were further diluted 1:50 into 5 mL of pre-warmed DMEM/HEPES and grown in 5% $CO_2$ atmosphere at 37° C. for 2 hours. Test compounds or DMSO were added to cultures and incubated for an additional 8 hours. To separate bacteria from secreted proteins, cultures were centrifuged at 3000 rpm for 10 minutes and the supernatant was passed through a 0.45 um filter. The bacterial pellet was re-suspended in 50 uL of loading buffer and boiled for 10 minutes for immunoblotting. Secreted proteins were precipitated with 10% cold TCA overnight at 4° C. for analysis by immunoblotting.

Example 2

The HTS Resulted 431 Primary Hits

As described previously, the HTS is based on the hypothesis that some T3S inhibitors would be able to convert *Y. pestis* from a no-growth/T3S state to a growth/no-T3S at 37° C. in $Ca^{2+}$ depleted medium as illustrated in FIG. 1. The screening was carried out by auto-dispensing the culture of luminescent *Y. pestis* strain JG401 in $Ca^{2+}$ depleted TB broth to 384-well plates, then pin transfer screening compounds to each well. After overnight incubation at 37° C., the relative luminescence unit (RLU) was measured.

For the HTS, Applicants selected 10 commercially available small molecule libraries and 3 plant extract libraries. The libraries consist of 69,093 single compounds and 1,873 plant extracts respectively, with total of 70,966 compounds and extracts, as shown in Table 10. The screening method, which is economical and robust, was used in the HTS. The initial screening was accomplished at the National Screening Laboratory within 2 weeks, and resulted 70,966 readouts in duplicates. After statistical analysis, as described previously, the inhibition (%) cutoff value was set as 10. Compounds whose tested activities were greater than this threshold (in duplicate) were selected as the primary HTS hits. The inhibition distribution of the screening compounds is shown in FIG. 2.

Based upon the intensity of the inhibition, the chemical characteristics of the compounds, and knowledge of other screens, 223 compounds were selected from 431 primary HTS hits for secondary confirmation screening. Eight strong and moderate primary hits were selected for further detailed study. The selection was based upon the activities in the primary screening, the chemical structures, and the commercial availabilities of the compounds. In this study, initial characterization of these compounds is reported, especially four of the eight compounds, that showed specific T3S inhibitory activity compound 1-4 (FIG. 3). The chemical names of the lead compounds are as follow: compounds 1: 2-Pyridinecarboxylic acid, 5-cyano-6-[[(4-methylphenyl)methyl]thio]-, compound 2: Phenol, 4,4'-thiobis[3-methyl-2, compound 3: Urea, N,N'-bis[3-(4,5-dihydro-1H-imidazol-2-yl)phenyl]-, compound 4: [4,5'-Bi-1H-pyrazole]-1'-pentanoic acid, 4',5'-dihydro-3-(4-methylphenyl)-δ-oxo-1-phenyl-3'-(2-thienyl)-; Imidocarb dipropionate (propanoic acid, compd. with N,N'-bis[3-(4,5-dihydro-1H-imidazol-2-yl)phenyl]urea (2:1)) was used as a hydrophilic compound 3.

Example 3

Selected Compounds Differentially Inhibited the Secretion of T3S Effectors

From the primary screening it was learned that the selected compounds are able to promote *Y. pestis* growth at 37° C. in the absence of $Ca^{2+}$. Whether or not they would also inhibit the T3S is the next logical question to be addressed. In order to answer this question, three proteins, YopH, YopM, and YopD, which are secreted by the T3SS, were used as secretion indicators to evaluate the activity of compounds. These three Yops represent a translocator protein (YopD), a well studied essential effector (YopH), and an important effector without well defined functions and mechanisms (YopM). The selected eight compounds were tested in YopM, YopH, and YopD secretion assays (for details see Materials and Methods). The bacterial culture supernatants were subjected to SDS-PAGE followed by western blots. From the eight primary hits, compound 1-4 (FIG. 3) showed concentration dependent inhibition on secretions of the Yops (FIG. 4). Interestingly, differential inhibition on secretions among Yop proteins was observed with compounds 1 and 3. Compound 1 inhibits YopH and YopD secretion with $IC_{50}$ around 10 μM; but for YopM secretion it is clear that the inhibition values are low and have no correlation to the concentrations (FIG. 4A). Compound 3 inhibits YopH secretion with $IC_{50}$ of 15 μM. At around 15 μM, inhibition of YopD by compound 3 reaches close to 50%, then decreases as the concentration of the compound increases. Inhibition activity of compound 3 towards YopM is barely observed (FIG. 4C). The $IC_{50}$s of compound 2 are around 10 μM for all three Yops. Compound 4 inhibits YopH YopD, and YopM secretion at around 20 μM, 30 μM, and 60 μM respectively.

Example 4

Compounds 1-4 Did not Inhibit *Y. pestis* Normal Growth

To further examine the specificity of the compounds that showed concentration dependent inhibition on Yop secretion, compounds 1-4 (FIG. 3) were tested in a *Y. pestis* growth assay. Since compounds 5-8 did not inhibit the secretion of Yops, their effects on *Y. pestis* growth were not tested in this assay. The HTS hits were considered based on increase of luminescence, which is presumably due to the promotion of bacterial growth. In order to confirm that the selected compounds do not negatively affect *Y. pestis* growth, the $OD_{600}$ of the bacterial culture was monitored in the presence of the compounds. All four compounds at concentrations tested showed no inhibitory effect on the growth of *Y. pestis* in TB supplemented with $Ca^{2+}$ (FIG. 5). In normal growth conditions (without T3S induction), compounds 1, 3, and 4 did not affect *Y. pestis* growth rate; the growth curves are parallel to the no compound controls (FIG. 5A). Compound 2 decreased the bacterial growth rate by about 5-10% (FIG. 5B). Surprisingly, the control T3S inhibitor INP0007 (Kauppi et al 2003, Nordfelth et al, 2005), completely inhibited the *Y. pestis* growth at 60 μM (FIG. 5C).

Example 5

Compounds 1, 3, and 4 Inhibited T3S Mediated Cytotoxic Response

Prior the T3S mediated cytotoxicity test, compounds were examined for cytotoxicity themselves. Compounds 1-4 (FIG. 3) were applied to HeLa cells in Dulbecco's Modified Eagle Medium (DMEM, Invitrogen) with 3% heat inactivated FBS as described in Materials and Methods. Compound 2 disrupted the cell monolayer in a concentration dependent manner; other test compounds did not change the morphology of the HeLa cells within the test concentrations (data not shown). Quantitative cytotoxicity of the compounds were obtained from the Lactate Dehydrogenase (LDH) cytotoxicity assay. Compounds 1, 3, and 4 did not cause the release of LDH from HeLa cells; compound 2 showed concentration dependent cytotoxicity to Hela cells (FIG. 6).

HeLa cells infected with the pCD1+ *Yersinia* strain exhibited a cytotoxic response to the infection, with a rounded-up morphology (FIG. 7A). In contrast, HeLa cells infected with the control pCD1− *Yersinia* strain did not exhibit a cytotoxic response to the control bacteria. Next, Compounds 1, 3, and 4 were examined for their ability to inhibit the T3S mediated cytotoxic response caused in HeLa cells by the pCD1+ *Yersinia* strain. In this assay, compounds 1, 3, and 4 prevented infected HeLa cells from exhibiting a morphological change, i.e., inhibited the cytotoxic response to infection by the pCD1+ *Yersinia* strain. Moreover, the inhibitions are concentration dependent for compounds 1, 3 and 4 (FIG. 7B).

Example 6

Compound 3 Dipropionate Inhibited Translocation of YopE to HeLa Cells

The T3S dependent morphological change in the assay of Example 4 is caused by the effector protein YopE. Translocated YopE mediates depolymerization of the actin microfilament network of the target cell. HeLa cells were infected by pMM85 (YopE-Bla) contain D122 in serum free DMEM medium with 24 μM HEPES pH 7.4. Compound 3 dipropionate was added, cultures were then incubated at 37° C. for 2-3 hours. CCF2-AM (Invitogen) was applied and visualized by fluorescence microscopy. Compound 3 dipropionate completely inhibited YopE-Bla translocation at 80 μM, and exhibited 50% inhibition of the translocation at 40 μM (FIG. 8).

Example 7

Compound 1 and 3 Showed Initial Broad Spectrum T3S Inhibitory Activity

Applicants have tested activity of Compounds 1-4 (FIG. 3) in enteropathogenic *Escherichia coli* (EPEC). EPEC utilizes T3SS to secrete several effectors. The translocated intimin receptor (Tir) is one of the effector molecules. Compound 1-4 were subjected to a Tir-secretion assay. In the presence of compounds 1 or 3, Tir secretion in EPEC culture was significantly reduced (FIG. 9), while compounds 2 and 4 did not inhibit the secretion of Tir up to 60 μM (data not shown).

Example 8

Applicants have re-tested large number of primary hits of the HTS through the cherry-picks. Due to time and other constraints, Applicants only selected eight of the primary hits for this study, from which 4 compounds showed promising inhibitory activity against Yop secretion in *Y. pestis* culture. The structures of these 4 compounds are distinct from each other, which show the great potentials for structure activity relationship (SAR) studies. For compound 2, it will also be valuable to test some analogs to get structural insight on activity and cytotoxicity, in order to improve or retain the activity while attempt to dispose of the toxic effect. On one hand, the compound may not be the best candidate for drug development because of its dose dependent cytotoxicity, on the other hand, understanding the SAR will provide us with powerful tools to study the mechanisms of its inhibitory effect and *Yersinia* T3S and may reveal promising analogs.

Compound 1-4 (FIG. 3) also demonstrated a surprising inhibition of secretion of Yops in *Y. pseudotuberculosis* within the same concentration ranges as in *Y. pestis* (data not shown). Since the expression and regulation of T3SS among *Yersinia* spp. are similar, the results are consistent with our understanding of the T3 SS mechanism in *Yersinia*. In contrast, when type III is induced in *E. coli* culture, the bacteria does not have the growth defect as *Y. pestis* does. It is remarkable that compounds 1 and 3 specifically inhibited the secretion of Tir in EPEC. This success of using compounds 1 or 3 to inhibit Tir secretion in *E. coli* provide evidence that these inhibitors have a broad spectrum of T3S inhibitory activity across bacterial genera.

In order to evaluate our compounds, Applicants have also applied a salicylaldehyde compound INP0007, reported by Elofsson group, to our Yop secretion assay. The compound was reported as the most potent T3S inhibitor in *Y. pseudotuberculosis*, has an $IC_{50}$ of 50 μM. As expected, the compound inhibited secretion of Yops in *Y. pestis*, and not to our surprise, it did not promote the growth of the bacteria as our compound 1-4 did (data not shown). These results indicated that the inhibition mechanism of compounds 1-4 are different from the INP0007. To make sure that compounds 1-4 would not inhibit the growth of *Y. pestis* even in the present of $Ca^{2+}$, Applicants monitored the bacterial growth in the present of test compounds in TB medium with $Ca^{2+}$ supplement (for details, see Materials and Methods). Among the lead compounds, only compound 2 slightly slowed the growth rate of JG153, compounds 1, 3, and 4 did not affect the bacterial growth rate. Compound 3 promoted the bacterial growth by shortening its lag time (not shown). The mechanism of the promotion is unknown, and obviously requires further study. The growth of *Y. pestis* was inhibited by INP0007 (ChemBridge Corporation, 5113023) (FIG. 5C). With limited information of the relation between its inhibitory effects on growth and T3S, Applicants discontinued using INP0007 as a specific T3S-inhibitor control.

Applicants have identified and confirmed 4 T3S inhibitors in this study. While evaluating the lead compounds, Applicants found that compounds 1 and 3 differentially inhibited the secretion of YopD, YopM, and YopH unexpectedly. These results indicate the target(s) of the compounds might be individual Yops and/or their secretion processes, but not the T3S machinery. All three Yops Applicants selected for the secretion tests are necessary for Yersinia virulence. YopD is a translocator, which is believed to be expressed and secreted prior the secretion of other Yops, and it is essential for the translocation of effectors into host cells with LcrH as the cognate charperone. YopD also plays a role in negative regulation of Yop and LcrV expression through LcrQ. YopH is one of the effectors that contribute to the strong resistance of pathogenic Yersinia to phagocytosis. It is a powerful phosphotyrosine phosphatase (PTPases), and the PTPase activity is probably relevant to its antiphagocytic action. SycH is a specific chaperone that is required for YopH secretion. YopM is translocated to cell's nucleus, but its pathogenic function is unknown. It interferes with innate immunity by causing depletion of NK cells. To date, there is no specific chaperone of YopM reported, and YopM does not need a chaperone in secretion process.

In summary, 4 lead compounds are chemically diverse, each having chemical scaffold distinct from one another, and also distinct from previously described candidate type III inhibitors. They show good promise as leads for structure-activity relationship (SAR) studies. Both compounds 1 and 3 show broad inhibitory spectrums. Compounds 1, 3 and 4 have good potential to inhibit Y. pestis infection in vivo.

Example 9

Identification and Uses of Type III Secretion Inhibitors

High Throughput Screening for Inhibitors of T3S in Y. pestis

Figure 1:
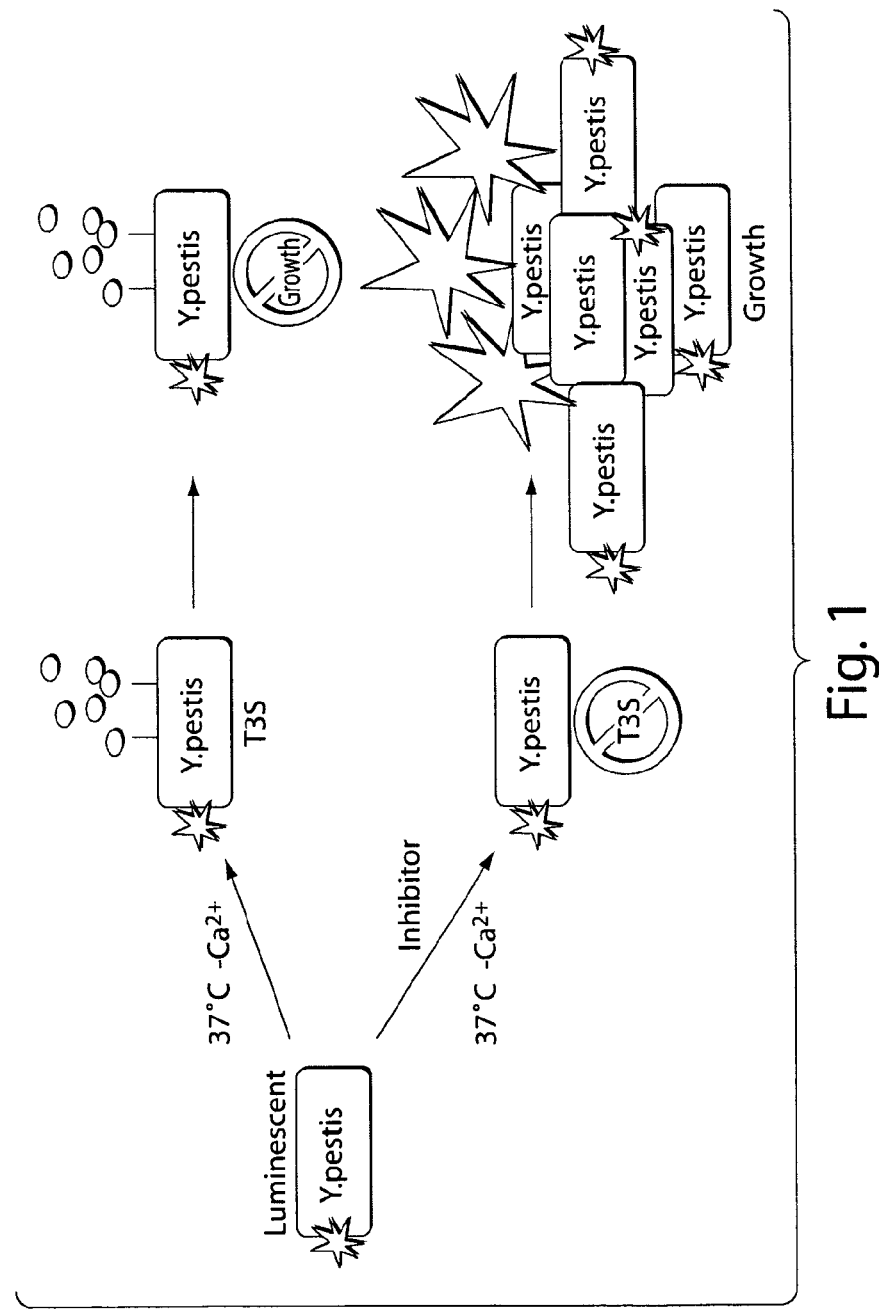
FIG. 1. The high throughput screening strategy. At 37° C. with low or no $Ca^{2+}$ in bacterial culture, Y. pestis will perform T3S with no growth. Presumably some classes of small molecules will convert the phenotype to growth with no or reduced T3S. Using luminescent Y. pestis provides a sensitive method of measuring the bacterial growth.
Figure 2:
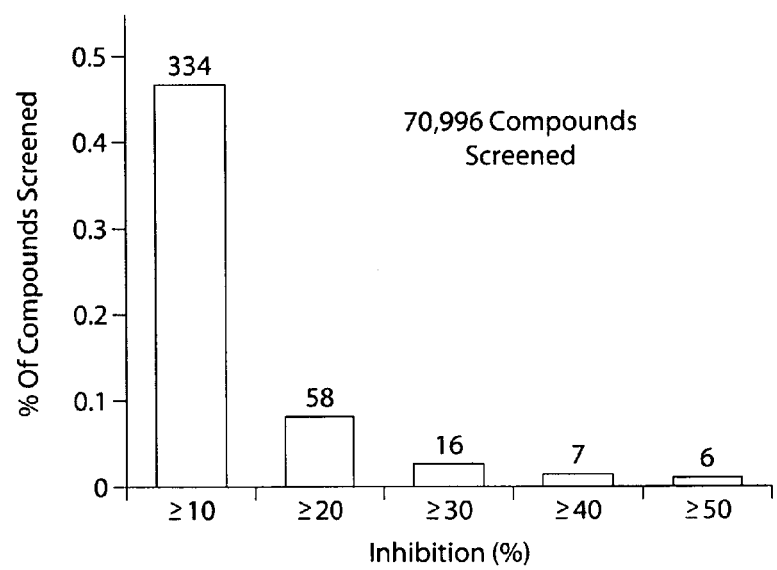
FIG. 2. Distribution of the primary hits from the high throughput screening. Data was FIG. 6. Cytotoxicity of compounds 1-4 determined by Lactate Dehydrogenase (LDH) assay. HeLa cells were treated with up to 60 µM of compounds 1-4 (including compound 3 dipropionate salt) at 37° C. for 2-3 hours. Aliquots of the cell culture supernatants were sampled. The amount of LDH released by 0.1% Triton X-100 treated cells and untreated normal cells were taken as $LDH_{high}$ and $LDH_{low}$ respectively. Cytotoxicity (%)=(exp. $LDH-LDH_{low}$)/($LDH_{high}-LDH_{low}$)×100. Error bars represent standard deviations of the means from three assays.
Figure 13:
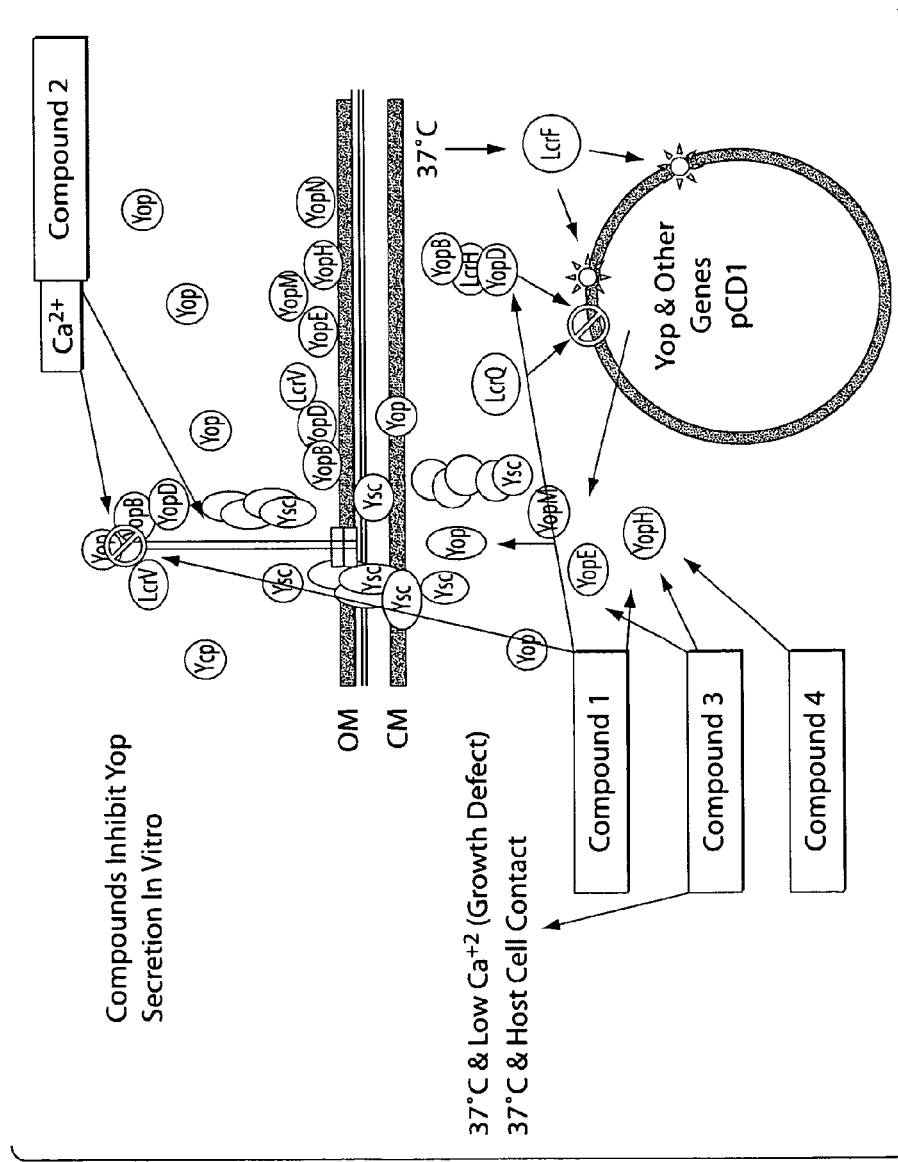
FIG. 13. Schematic of the effects of compounds on Type III Secretion system proteins.
Figure 14:
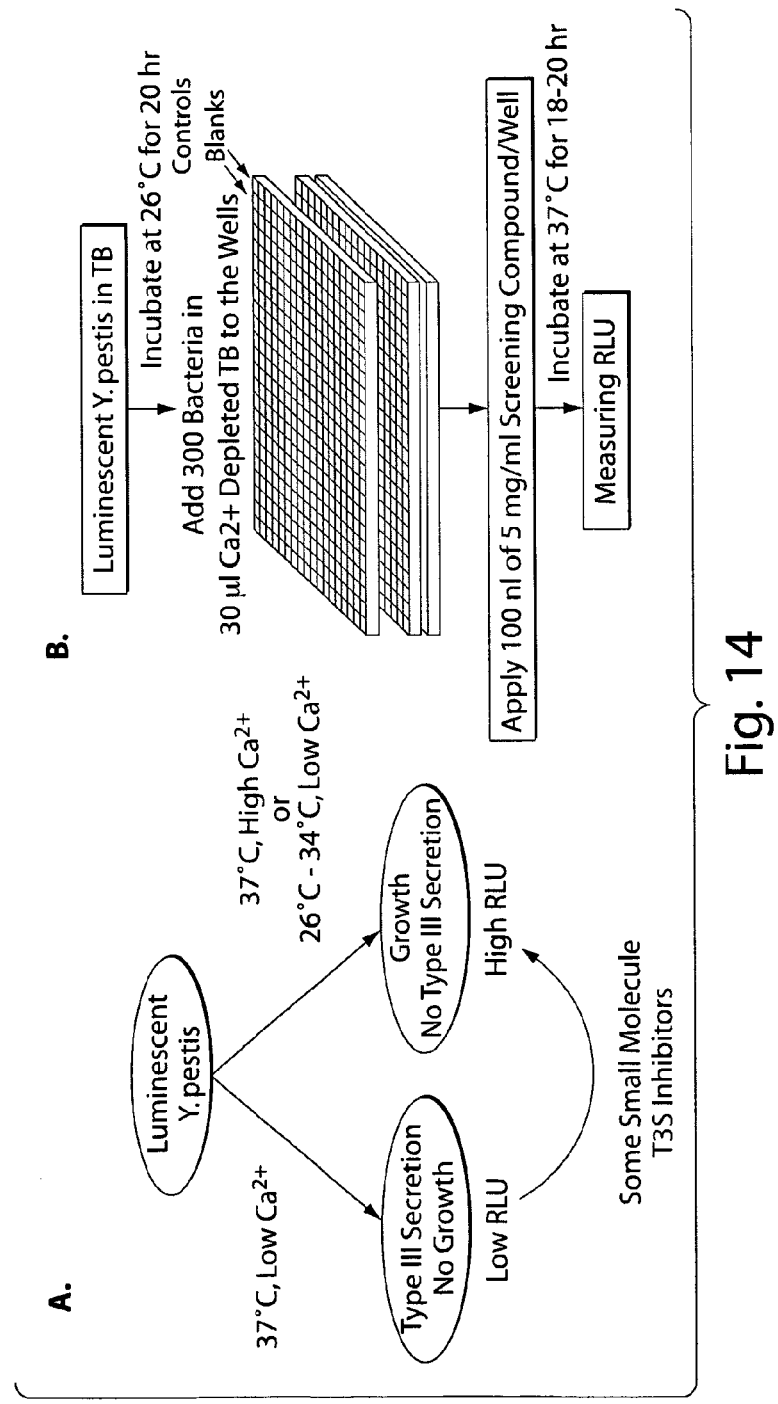
FIG. 14. The high throughput screening for inhibitors of T3S in *Yersinia*. A. Illustration of the screening strategy. At 37° C. with low or no Ca2+ in bacterial culture, *Y. pestis* will perform T3S with no growth. Presumably some classes of small molecules will convert the phenotype to growth with no or reduced T3S. B. Flowchart of the HTS method to screen libraries of small molecules for their ability to promote growth of *Y. pestis* under the conditions, with which the T3S would be induced otherwise.
Figure 15:
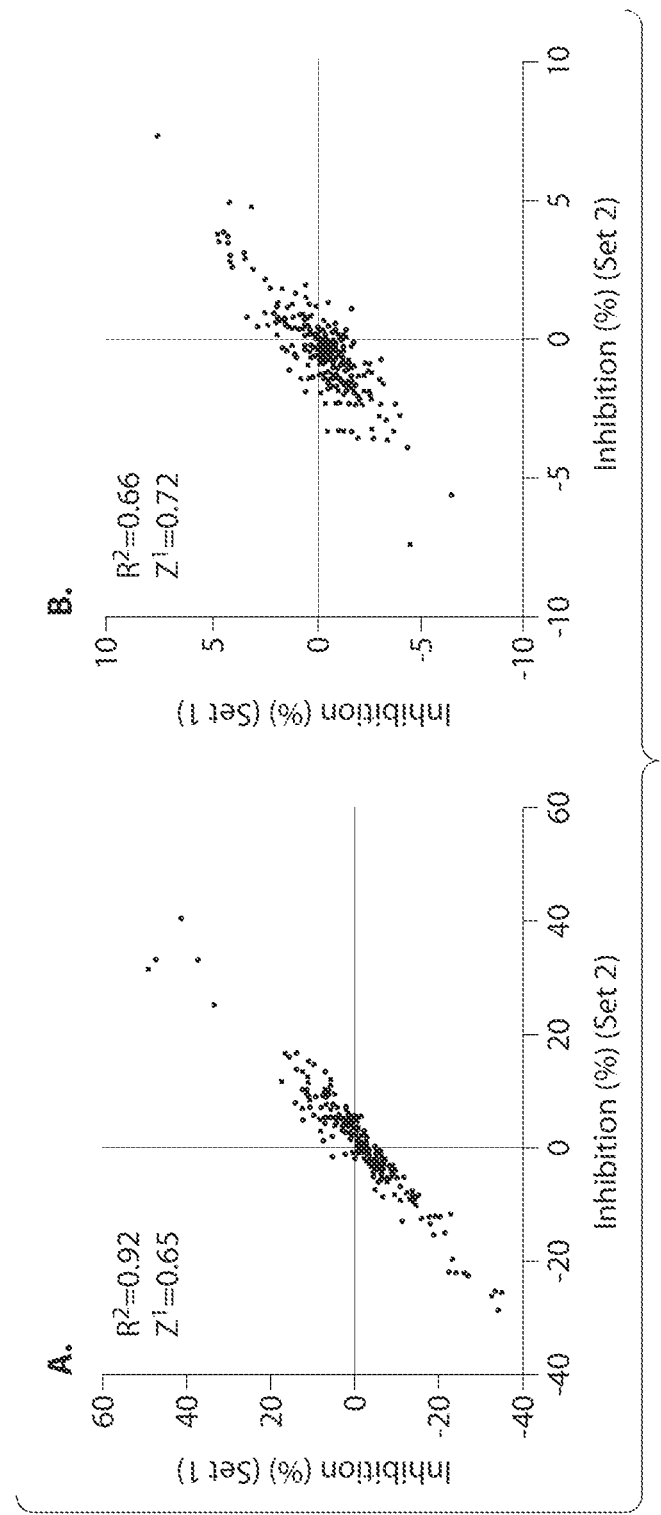
FIG. 15. Assay variability and Z' value. Data from four sets of 384-well duplicate plate pairs (A-D), were selected at random for analysis. The variability of the duplicate data, was evaluated by plotting the inhibition (%) values obtained in Plate 1 versus that of Plate 2 of each set. The correlations between the two plates for each of the four pairs are plotted. Correlation coefficients (R2) were 0.92, 0.66, 0.89, and 0.88 for plate A, B, C, and D respectively. The Z' statistic, which evaluates signal-to-noise ratio and dynamic range, was also calculated for these four data sets, yielding values of 0.65, 0.72, 0.70, and 0.66 respectively. Z' values between 0.5 and 1 are generally regarded as excellent for HTS methods.
Figure 15:
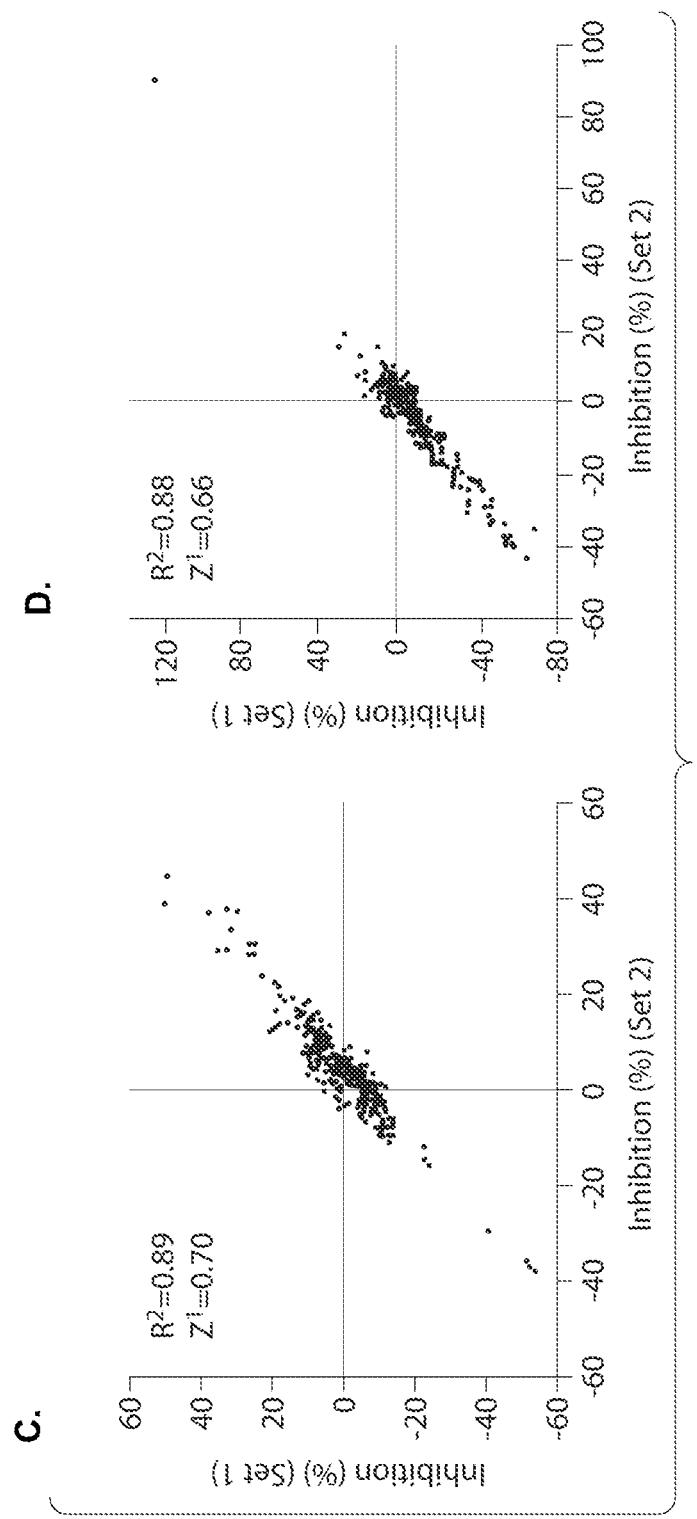

A very rapid, convenient, and inexpensive method for high-throughput screen for T3S inhibitors in Y. pestis is disclosed. In comparison with previously reported techniques, this method is faster, simpler to execute, and requires minimal reagents other than bacteriological media and the compounds to be tested. This method is based on the expectation that at least some classes of T3S inhibitors will suppress the LCR, permitting growth at 37° C. in the absence of calcium (See, for example, FIGS. 1, 13 and 14). A specially constructed avirulent Y. pestis strain that meets the requirements for exemption for Select Agent status—and thus can be used outside of BSL-3 laboratories and secure facilities—but retains the intact T3S system is used. Relevant to the assay, this specially constructed avirulent Y. pestis strain has strong luminescence, and a selectable marker to the Yersinia virulon, pCD1. The selectable marker facilitates retention of the pCD1 plasmid in cultures, and stabilization of pCD1 against spontaneous deletion. Together, these features permit detection of growth via increased luminescence as a screening read-out for potential T3S inhibitors. This method avoids the background of false positives caused by spontaneous genetic lesions that result in loss of T3S function and that can be an issue with other screening methods. For example, such false positives can emerge in T3S screening approaches that depend, as a screening read-out, on the expression of a reporter gene transcribed by a T3SS protein encoding gene promoter.

Materials and Methods

Y. pestis Strains, Growth Conditions, and Mammalian Cell Culture

A luminescent Y. pestis JG401 strain was constructed by introducing the lux operon from Photorhabdus luminescence contained in plasmid pML001 (AmpR), and a pCD1 derivative, pCD1K22, marked with a Mariner transposon derivative conferring kanamycin resistance, but lacking the Mariner transposase. The location of this insertion was selected to reduce the rate of spontaneous internal deletions in pCD1. This selection was made, because such deletions could otherwise occur at a rate almost as high as spontaneous pCD1 segregation ($10^{-4}$-$10^{-5}$ in overnight cultures). When grown as indicated, the rate of colony formation for JG401 on calcium-free medium at 37° C. was less than $5 \times 10^{-7}$. To ensure avirulence, JG401 also lacks the Pla-encoding plasmid pPCP1 and carries the 100 kb chromosomal pgm deletion, which includes genes required for iron acquisition during infection. A T3S deficient luminescent Y. pestis strain JG406 (JG401 pCD1−) was also constructed. Y. pestis strains were cultured in TB broth (1% bacto tryptose, 0.3% bacto beef extract, 0.5% NaCl) at 26° C. unless otherwise indicated. HeLa cells were maintained in Dulbecco's modified Eagle's medium (DMEM) supplemented with 10% heat inactivated fetal bovine serum (FBS), 100 units/ml penicillin and 100 µg/ml streptomycin at 37° C. with 5% CO2.

Primary High Throughput Screening Assay

The high-throughput screening (HTS) was conducted at the National Screening Laboratory (NSRB) located at Harvard Medical School, Boston, Mass. For high-throughput screening, a JG401 overnight culture was diluted into TB broth supplemented with 20 mM MgCl2, 100 µg/ml ampicillin, and 50 µg/ml kanamycin. 30 µl of JG401 diluted with the same medium to a density of $10^4$/ml was added into each well of 384-well cell culture plates (Nalge Nunc International, USA, catalog number 164610) to give 300 bacteria/well. A Bio-Tek µFill plate dispenser with Bio-Tek Bio-Stack (Bio-Tek Instruments) was used in this operation. The compounds in the screening libraries, at a concentration of 5 mg/ml (in DMSO), were arrayed in the 384 well plates. 100 nl of each compound to be screened was applied to each well of the assay plates using an Epson compound transfer robot with standard volume pin arrays. 2.5 mM CaCl2 was added to the bacterial culture in two wells on each plate as the assay positive control and as an intra-plate control. The plates were incubated overnight at 37° C. The relative luminescence unit (RLU) was measured by using Perkin Elmer EnVision plate readers equipped with a 40-plate stack loader. The screening was performed in duplicate sets of plates, identified as set 1 and set 2.

The Secondary Screening Assay

In secondary confirmation screening, selected primary hits in DMSO were added to the bacterial culture, with the same dilution factors as above, in the 384-well plates at different concentrations. The plates were then incubated overnight at 37° C. The RLU was measured in an EnVision microplate reader. In addition to JG401, JG406 was also used in the secondary screening to ensure the tested compounds did not act substantially as bacterial growth inhibitors. The experiments were performed in triplicate with both strains. JG406 was cultured in TB broth supplemented with 100 µg/ml ampicillin.

Statistical Analysis of Screening Results

The activity of small molecules and extracts in set 1 and set 2 of each screening run were calculated separately by using Eq. 1. The same analysis was applied to secondary screening data. The relative noise and dynamic range of the screening data were evaluated using the Z' statistic (Zhang et al., 1999). Data from cultures grown in calcium supplemented media provides positive control measurement.

$$\text{Inhibition (\%)} = (RLU - RLU_{bkg}) \times 100 / (RLUCT - RLU_{bkg}) \quad \text{Equation 1}$$

RLU: relative luminescence unit (luminescence unit/sec)
$RLU_{bkg}$: background RLU
RLUCT: positive control RLU Assay for Inhibition of T3S in *Y. pestis* Culture

*Y. pestis* overnight culture in TB was subcultured into brain-heart infusion (BHI) broth, then incubated at 30° C. with aeration till mid-log phase. Test compounds at the desired concentrations were then added to the bacterial cultures. The cultures were shifted to 37° C. for two to four hours to induce T3S, centrifuged, and the resulting supernatant assayed for secreted Yops via antibody-based enzyme-linked immunosorbent assay (ELISA) and immunoblot. Specific anti-Yop antibodies were used in the assays.

High Throughput Screening (HTS) Results

Using the assay described above, 70,966 compounds were screened in a period of two weeks with two people traveling daily between University of Massachusetts Medical School (UMMS) and NSRB. Use of the luminescent JG401 allowed very low-noise and sensitive detection of growth, at least 10-fold less noisy than possible by measurement of optical density in the 384 well format. The sensitivity is many orders of magnitude greater than OD measurements, allowing detection of even the low initial inoculums. In practice, a dwell time of 0.1 second/well was sufficient for luminescence readings, allowing rapid processing of plates after overnight incubation. In a two-day processing cycle, as many as 19,200 compounds were tested in duplicate. To evaluate the quality of the screening assay, four randomly selected duplicate plate pairs were analyzed (FIG. 15). Results of these analyses indicated good assay performance. Based on this evaluation, we set the cutoff value for selecting positives at 10% of the luminance produced by positive controls. Compounds whose tested activities were greater than this threshold (in duplicates) were considered as our primary HTS hits. Strong positive indications of inhibition were observed at a rate of 0.01%, while moderate and weak but potentially meaningful signals were observed at rates of 0.056% and 0.54% respectively. Based upon the intensity of the inhibition, chemical characteristics of the potential inhibitors, and correlation with results from other unrelated screens run by NRSB investigators (to exclude compounds positive in several unrelated assays), we selected 223 cherry-picks from 431 primary HTS hits for secondary confirmation (data not shown).

REFERENCES

Abe, A. (2002). Development of the screening system for the bacterial type III secretion apparatus inhibitor. The Japanese Journal Of Antibiotics 55, 331-336.

Ben-Gurion, R., and Shafferman, A. (1981). Essential virulence determinants of different *Yersinia* species are carried on a common plasmid. Plasmid 5, 183-187.

Boland, A., Sory, M. P., Iriarte, M., Kerbourch, C., Wattiau, P., and Cornelis, G. R. (1996). Status of YopM and YopN in the *Yersinia* Yop virulon: YopM of *Y. enterocolitica* is internalized inside the cytosol of PU5-1.8 macrophages by the YopB, D, N delivery apparatus. The EMBO Journal 15, 5191-5201.

Cornelis, G. R. (2002). The *Yersinia* Ysc-Yop 'type III' weaponry. Nat Rev Mol Cell Biol 3, 742-752.

Ferber, D. M., and Brubaker, R. R. (1981). Plasmids in *Yersinia pestis*. Infection And Immunity 31, 839-841.

Gauthier, A., Robertson, M. L., Lowden, M., Ibarra, J. A., Puente, J. L., and Finlay, B. B. (2005). Transcriptional inhibitor of virulence factors in enteropathogenic *Escherichia coli*. Antimicrobial Agents And Chemotherapy 49, 4101-4109.

Hakansson, S., Schesser, K., Persson, C., Galyov, E. E., Rosqvist, R., Homble, F., and Wolf-Watz, H. (1996). The YopB protein of *Yersinia pseudotuberculosis* is essential for the translocation of Yop effector proteins across the target cell plasma membrane and displays a contact-dependent membrane disrupting activity. The EMBO Journal 15, 5812-5823.

Higuchi, K., Kupferberg, L. L., and Smith, J. L. (1959). Studies on the nutrition and physiology of *Pasteurella pestis*. III. Effects of calcium ions on the growth of virulent and avirulent strains of *Pasteurella pestis*. J Bacteriol 77, 317-321.

Kauppi, A. M., Nordfelth, R., Uvell, H., Wolf-Watz, H., and Elofsson, M. (2003). Targeting bacterial virulence: inhibitors of type III secretion in *Yersinia*. Chemistry & Biology 10, 241-249.

Linington, R. G., Robertson, M., Gauthier, A., Finlay, B. B., van Soest, R., and Andersen, R. J. (2002).

Caminoside A, an antimicrobial glycolipid isolated from the marine sponge *Caminus sphaeroconia*. Organic Letters 4, 4089-4092.

Mueller, C. A., Broz, P., Muller, S. A., Ringler, P., Erne-Brand, F., Sorg, I., Kuhn, M., Engel, A., and Cornelis, G. R. (2005). The V-antigen of *Yersinia* forms a distinct structure at the tip of injectisome needles. Science 310, 674-676.

Muschiol, S., Bailey, L., Gylfe, A., Sundin, C., Hultenby, K., Bergstrom, S., Elofsson, M., Wolf-Watz, H., Normark, S., and Henriques-Normark, B. (2006). A small-molecule inhibitor of type III secretion inhibits different stages of the infectious cycle of *Chlamydia trachomatis*. Proc Natl Acad Sci USA 103, 14566-14571.

Nordfelth, R., Kauppi, A. M., Norberg, H. A., Wolf-Watz, H., and Elofsson, M. (2005). Small-molecule inhibitors specifically targeting type III secretion. Infection And Immunity 73, 3104-3114.

Rosqvist, R., Forsberg, A., and Wolf-Watz, H. (1991). Intracellular targeting of the *Yersinia* YopE cytotoxin in mammalian cells induces actin microfilament disruption. Infection And Immunity 59, 4562-4569.

Rosqvist, R., Magnusson, K. E., and Wolf-Watz, H. (1994). Target cell contact triggers expression and polarized transfer of *Yersinia* YopE cytotoxin into mammalian cells. Embo J 13, 964-972.

Wolf, K., Betts, H. J., Chellas-Gery, B., Hower, S., Linton, C. N., and Fields, K. A. (2006). Treatment of *Chlamydia trachomatis* with a small molecule inhibitor of the *Yersinia* type III secretion system disrupts progression of the chlamydial developmental cycle. Mol Microbiol 61, 1543-1555.

Zhang, J. H., Chung, T. D., and Oldenburg, K. R. (1999). A Simple Statistical Parameter for Use in Evaluation and Validation of High Throughput Screening Assays. J Biomol Screen 4, 67-73.

TABLE 9

Bacterial strains and plasmid used

| Strain or plasmid | Construction and properties | Source or reference |
|---|---|---|
| *Y. pestis* strains | | |
| JG401 | KIM pCD1K pPCP1- Δpgm pML001 | This TABLE 12-continued Type III Secretion Inhibitor Compound Analogs

| The analogs | CID (Pubchem ID) | CAS number | Molecular Formula | SMILES | Molecular Weight |
|---|---|---|---|---|---|
| 6 Compound 4_1 | 4374073 | 381727-89-5 | $C_{27}H_{24}N_4O_3S$ | C1C(N(N=C1C2=CC=CS2)C(=O)CCCC(=O)O)C3=CN(N=C3C4=CC=CC=C4)C5=CC=CC=C5 | 484.571 |
| 7 Compound 4_2 | 3486379 | 384355-59-3 | $C_{28}H_{25}N_4O_4$ | COC1=CC=C(C=C1)C2=NN(C=C2C3CC(=NN3C(=O)CCCC(=O)O)C4=CC=CS4)C5=CC=CC=C5 | 514.597 |

Example 10

First Round Compound 1 Analogs

T3S Inhibitor compound 1 analogs were tested to evaluate inhibition of Type-III secretion, cytotoxicity, and *Y. pestis* growth inhibition. Compound 1 and its analogs are shown in tables 1, 3 and 4.

T3S Inhibition (YopE::Bla Secretion).

Figure 16A:
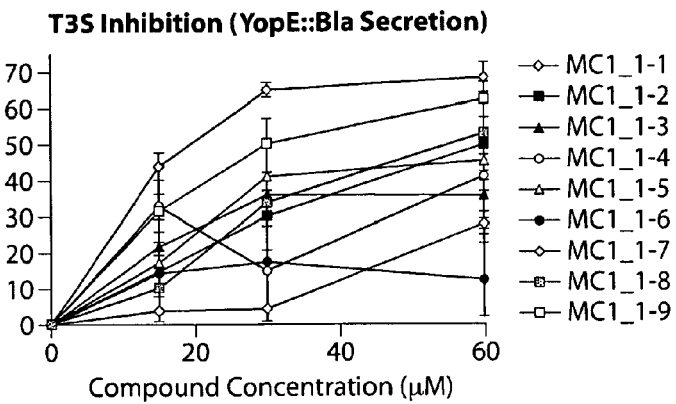
FIG. 16 depicts functional assessments of compound 1 (lead 1) analogs. T3S inhibition by compound 1 analogs was evaluated in a YopE::Bla secretion assay (FIG. 16A). Cytotoxicity of compound 1 analogs was evaluated in an LDH assay (FIG. 16B). *Y. pestis* growth inhibition of compound 1 analogs was evaluated as disclosed herein (FIG. 16C).

T3S inhibition by compound 1 analogs (See Table 3) was evaluated in a YopE::Bla secretion assay (FIG. 16A). From at least 3 experiments, four out of nine analogs showed greater than 50% inhibition on YopE-Bla secretion at 60 μM. Secretion was monitored by measuring beta-lactamase activity in the bacterial culture. The 1050 of YopE secretion are estimated as below.

TABLE 13

IC50 of YopE secretion

| Sample ID | MC1_1-1 | MC1_1-2 | MC1_1-3 | MC1_1-4 | MC1_1-5 | MC1_1-6 | MC1_1-7 | MC1_1-8 | MC1_1-9 |
|---|---|---|---|---|---|---|---|---|---|
| IC50 (μM) | 20 | 60 | >60 | >60 | ≥60 | no estimate | >60 | 55 | 30 |

Figure 16B:
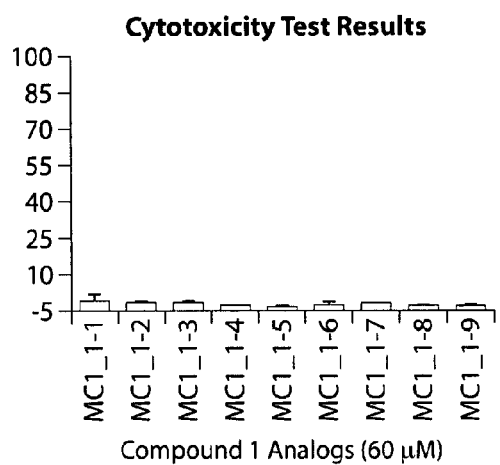

Cytotoxicity of compound 1 analogs was evaluated (FIG. 16B). None of the analogs showed any cytotoxicity to HeLa cells when using 1% TritonX-100 as positive control.

Figure 16C:
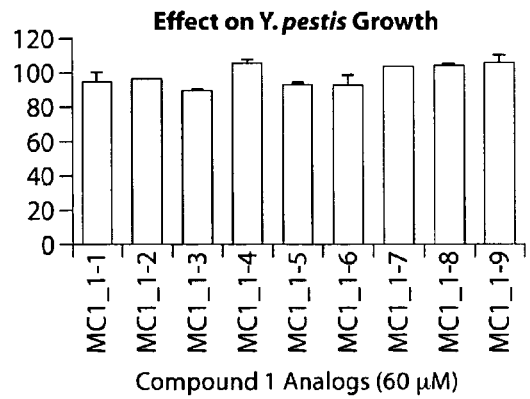

*Y. pestis* growth inhibition of compound 1 analogs was evaluated (FIG. 16C). None of the analogs inhibited *Y. pestis* growth at 37° C. 15 μM, 30 μM (not shown), and 60 μM of each test compound were added to the bacterial culture.

Example 11

Compound 3 Analogs

T3S Inhibitor compound 3 analogs were tested to evaluate inhibition of Type-III secretion, cytotoxicity, and *Y. Pestis* growth inhibition. Compound 3 and its analogs are shown in tables 1, 2, 6, 7 and 8.

Figure 17A:
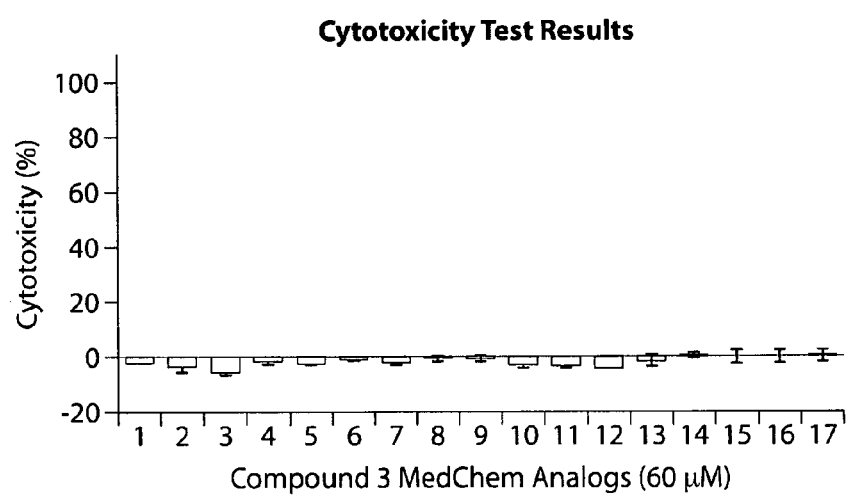
FIG. 17 depicts functional assessments of first round compound 3 (lead 3) analogs. Cytotoxicity of compound 3 analogs was evaluated using an LDH assay (FIG. 17A). T3S inhibition by compound 3 analogs was evaluated in a YopH secretion assay (FIG. 17B). Evaluation of concentration dependent *Y. pestis* growth inhibition by 5 analogs of compound 3 (FIG. 17C).

First Round Compound 3 (Lead 3) Analogs:

Cytotoxicity of analogs of compound 3 (See Table 6) was evaluated using an LDH assay (FIG. 17A). None of the test analogs were cytotoxic at 60 μM in this assay. The experimental conditions are as described herein.

Figure 17B:
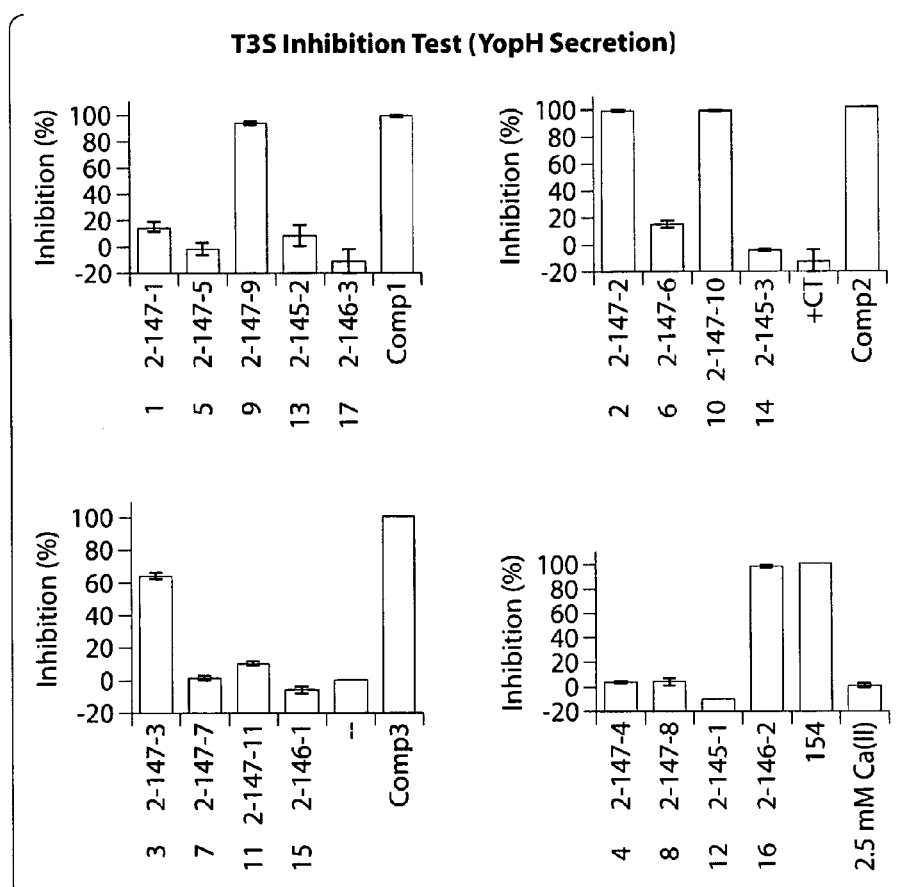

T3S inhibition by compound 3 analogs was evaluated in a YopH secretion assay (FIG. 17B). T3S Inhibition Figure. Inhibition of YopH secretion by MedChem analogs of compound 3. 60 μM of test compounds were added to the bacterial culture prior T3S induction. YopH secretion was measured by using ELISA as described herein. Compound 1, 2, and 3 were used as inhibitor controls. 17 analogs of compound 3 were tested in this assay.

Figure 17C:
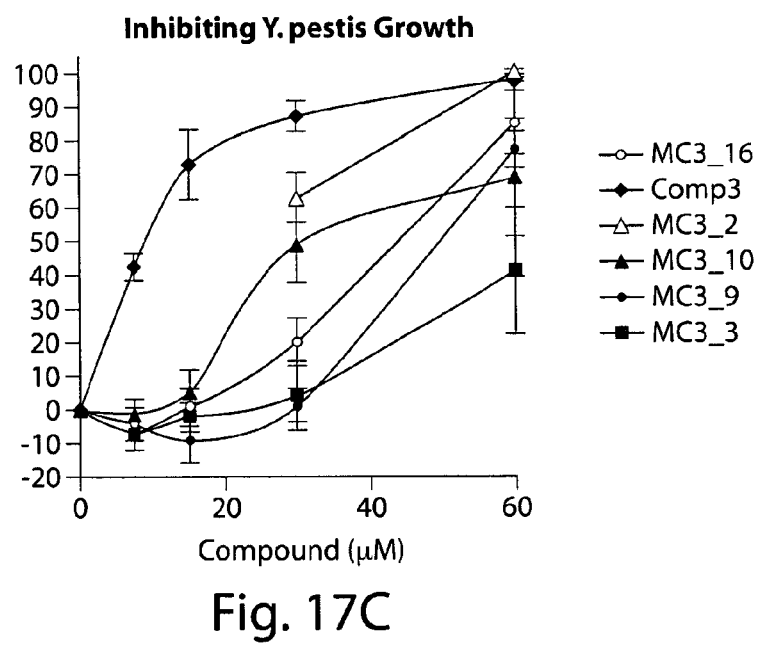

Concentration dependent T3S inhibition of 5 analogs of compound 3 was evaluated (FIG. 17C). Bacterial culture and T3S induction conditions are described herein. Different concentrations of the testing compounds were added to the bacterial cultures as indicated. Compounds MC3_2, MC3_3, MC3_9, MC3_10, and MC3_16 showed concentration dependent inhibitory activities. MC3_2, MC3_3, MC3_9, MC3_10, and MC3_16 of FIG. 17C respectively correspond to compounds MC3_1-2, MC3_1-3, MC3_1-9, MC3_1-10, and MC3_1-16 of Table 6.

Figure 18A:
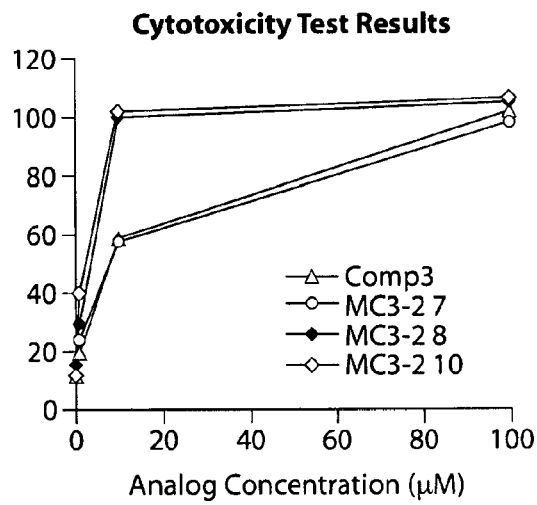
FIG. 18 depicts functional assessments of second round compound 3 (lead 3) analogs. T3S inhibition by compound 3 analogs was evaluated in a YopE::Bla secretion assay (FIG. 18A). Cytotoxicity of compound 3 analogs was evaluated using an LDH assay (FIG. 18B).

Second Round Compound 3 (Lead 3) Analogs:

T3S inhibition by compound 3 analogs was evaluated in a YopE::Bla secretion assay (FIG. 18A). From at least 5 independent experiments, three analogs (MC3_2-7, MC3_2-8, and MC3_2-10, See Table 7) consistently showed inhibitory effect on YopE-Bla secretion. Secretion was monitored by measuring beta-lactamase activity in the bacterial culture. The IC50 of YopE secretion are 10 μM, 2 μM, and 1 μM for MC3_2-7, MC3_2-8, and MC3_2-10 respectively.

Cytotoxicity Test Results

Figure 18B:
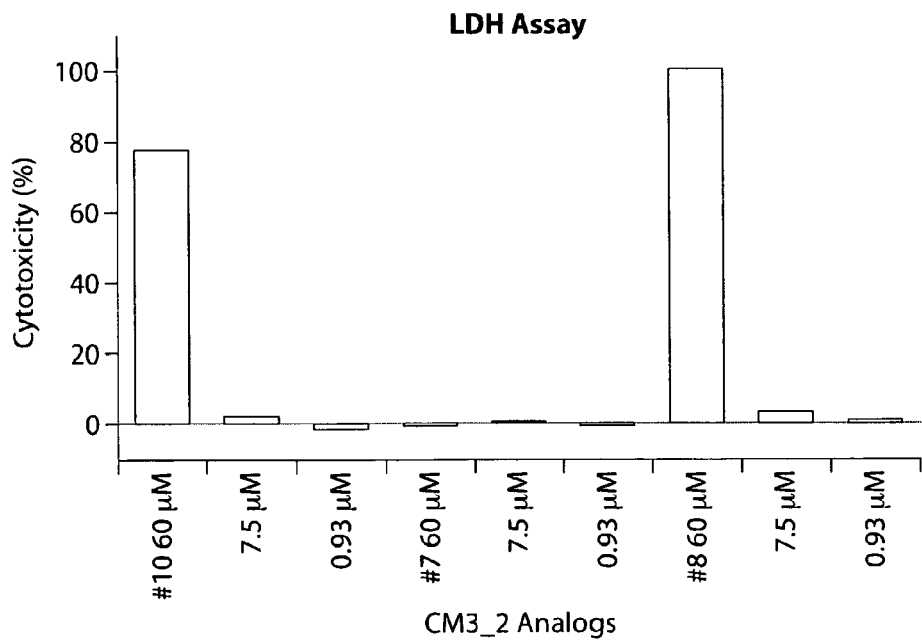

Cytotoxicity of compound 3 analogs was evaluated using an LDH assay (FIG. 18B). MC3_2-7 did not exhibit cytotoxicity. MC3_2-8 and MC3_2-10 were cytotoxic (i.e., ~100% and ~80%, respectively) to HeLa cells. TritonX-100 (1%) was used as a positive control.

*Y. pestis* growth inhibition of compound 3 analogs was evaluated. From a duplicate bacterial growth experiment (data not shown), all three analogs, MC3_2-7, MC3_2-8, and MC3_2-10 inhibited *Y. pestis* growth at 37° C. The IC50s are 30 μM, 10 μM and 8 μM.

Summary:

Three particularly active compounds were identified. Both MC3_2-8 and MC3_2-10 showed about a 10-fold increase in inhibitory activity against T3S. MC3_2-7 returned similar activity compare to the parent compound. At higher concentrations, all three compounds showed inhibitory effect of *Y. pestis* growth; cytotoxicity was also observed from two of the three compounds.

Example 12

Commercial Analogs of Compounds 2, 3 and 4

Commercial analogs of compounds were obtained from the following sources: TimTec Corporation, Newark, Del., USA.; Scientific Exchange, Inc. Center Ossipee, N.H., USA; Enamine Ltd., Kiev, Ukraine; Analogix, Inc., USA; Sigma-Aldrich, St. Louis, Mo., USA.; and ChemBridge Corporation, San Diego, Calif., USA (See Table 2).

Figure 19A:
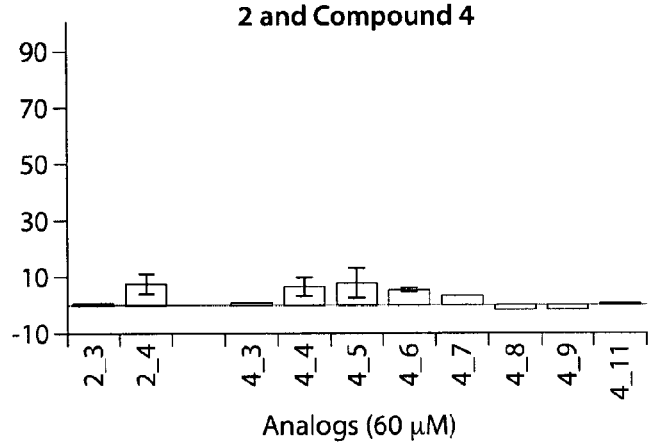
FIG. 19 depicts functional assessments of commercial analogs of compounds 2, 3 and 4. Cytotoxicity of analogs was evaluated (FIG. 19A). Test analogs of compound 2 (lead 2), compound 3 (lead 3), and compound 4 (lead 4) were added to HeLa cell cultures at final concentration of 60 µM and the Cytotoxicity (%) was measured and calculated as disclosed herein. Data shown are the mean values of two experiments with standard deviation as errors. T3S inhibition of commercially available analogs was evaluated in a YopH assay (FIG. 19B). Inhibition (%) was calculated as described herein. Concentration dependent T3S inhibition was evaluated for selected analogs (FIG. 19C).

Cytotoxicity of analogs was evaluated (FIG. 19A). Test analogs of compound 2 (lead 2), compound 3 (lead 3), and compound 4 (lead 4) were added to HeLa cell cultures at final concentration of 60 μM and the Cytotoxicity (%) was measured and calculated as disclosed herein. Data shown are the mean values of two experiments with standard deviation as errors. None of the test analogs showed cytotoxicity to HeLa cells. Both analogs, 2-3 and 2-4 (See Table 2), showed significant decrease in cytotoxicity compared to their parent compound 2.

Figure 19B:
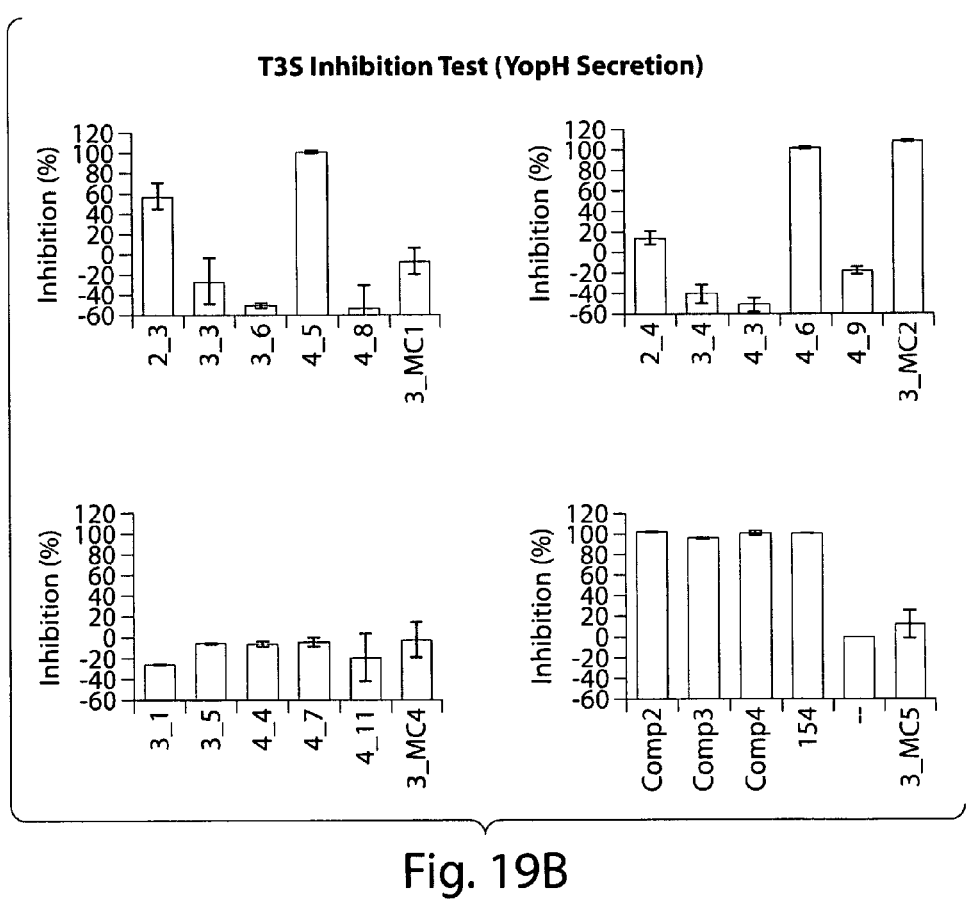
Figure 19C:
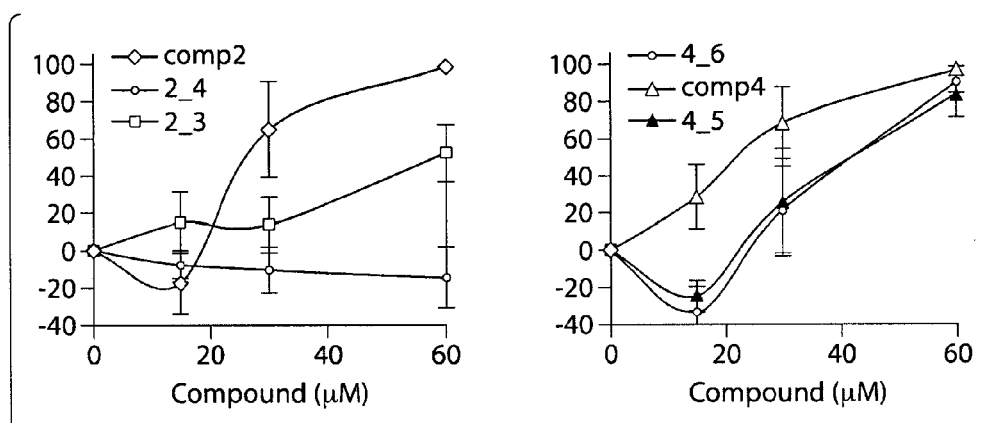

T3S inhibition by commercially available analogs was evaluated in a YopH assay (FIG. 19B). *Y. pestis* JG153 and JG154 strains were used in this assay. Bacterial overnight culture in TB broth was sub-cultured into BHI broth to OD600=0.04. The culture was then grown at 30° C. in flasks with shaking until an OD600 of 0.2 is reached. Different concentrations of the testing compounds were added to the bacterial cultures. The cultures were then shifted to 37° C. for Type III secretion (T3S) induction for 2 hours. The culture supernatants were collected after centrifugation and subjected to ELISA for relative concentration of YopH. A polyclonal rabbit anti-YopH antibody, a gift from Dr. Susan Straley, was used in this assay. The inhibition (%) was calculated by using the following equation.

$$\text{Inhibition}(\%) = 100\times\left(1-\frac{YopH - YopH_{-CT}}{YopH_{+CT} - YopH_{-CT}}\right)$$

$+CT$: $T3S$ positive control $-CT$: $T3S$ negative control

Analogs 2-3, 4-5, and 4-6 (See Table 2) showed activity against YopH secretion. Four custom synthesized compound 3 analogs were also tested. 3_MC1, 3_MC2, 3_MC4, and 3_MC5 respectively correspond to MC3__1-1, MC3__1-2, MC3__1-4, and MC3__1-5 (See Table 6), from which, 3_MC2 showed inhibition of YopH secretion.

Concentration dependent T3S inhibition was evaluated for selected analogs (FIG. 19C). Bacterial culture and T3S induction conditions are disclosed herein. Different concentrations of the testing compounds were added to the bacterial cultures as indicated (2-3 & 2-4 (left) and 4-5 & 4-6 (right)). Analog 2-3 retained inhibitory activity and overcame the cytotoxicity of parent compound 2 (lead 2).

Example 13

YopE::Bla Secretion Assay

Assay of YopE-Bla fusion protein secretion. Overnight cultures of YopE::Bla-expressing *Y. pestis* strains either JG153 (pMM85[1]) or JG154 (pMM85) were grown in TB broth at 30° C. and used to inoculate BHI broth to OD600=0.04. The cultures were then grown at 30° C. until an OD600 of 0.2 is reached. Compounds under test were then added at the indicated concentrations. The cultures were then shifted to 37° C. to induce T3S and incubated for an additional 2 to 3 h. The culture supernatants were collected following centrifugation (3000×g, 10 m). Final concentration of 50 μg/ml CENTA[2], a beta-lactamase susceptible chromogenic cephalosporin reagent, was added to 100 μl of the bacterial culture supernatant. The color change of CENTA, from light yellow (340 nm) to chrome yellow (405 nm), was monitored by a micro-titer plate reader at 405 nm. We use JG153 (pMM85) culture with DMSO as type III secretion (T3S) positive control, and JG154 (pMM85) as T3S negative control. The inhibition of YopE-Bla secretion (%) was calculated by using the following equation.

[1] Marketon, M. M.; DePaolo, R. W.; DeBord, K. L.; Jabri, B.; Schneewind, O., Plague bacteria target immune cells during infection. Science 2005, 309, (5741), 1739-1741.

[2] Jones, R. N.; Wilson, H. W.; Novick, W. J., Jr.; Barry, A. L.; Thornsberry, C., In vitro evaluation of CENTA, a new beta-lactamase-susceptible chromogenic cephalosporin reagent. J Clin Microbiol 1982, 15, (5), 954-8.

$$\text{Inhibition}(\%) = 100\times\left(1-\frac{OD - OD_{-CT}}{OD_{+CT} - OD_{-CT}}\right)$$

Example 14

YopE::Bla Secretion Assay

We performed T3S inhibition (YopE-Bla secretion) assays on the 2nd round of MedChem analogs of compound 1 (lead 1). Results are shown in Table 14. Out of 19 analogs, 2 showed≥50% inhibition on YopE-Bla secretion at 60 μM. MC 1__2-3 and MC1__2-19 inhibit the secretion around 95% and 50% respectively. Secretion was monitored by measuring beta-lactamase activity in the bacterial culture. Data of each analog was collected from at least 3 samples.

TABLE 14

T3S inhibition assay results on the 2nd round of MedChem analogs of compound 1 (lead 1)

| ID | Structure | Sample ID | Mean Inhibition (%) | Std. Dev. |
|---|---|---|---|---|
| 3-78-1 | iPr-S- | MC1_2-1 | 29.5 | 17.0 |
| 3-78-2 | cyclohexyl-S- | MC1_2-2 | 19.4 | 1.7 |
| 3-78-3 | 4-Cl-C6H4-S- | MC1_2-3 | 95.9 | 2.2 |
| 3-83-1 | HO(CH2)3-NH- | MC_12-4 | 17.4 | 7.1 |
| 3-83-2 | Et2N- | MC1_2-5 | 24.5 | 8.0 |
| 3-83-3 | 4-(EtO2C)-piperidin-1-yl | MC1_2-6 | 26.0 | 2.9 |
| 3-83-4 | 2-(CO2Et)-piperidin-1-yl | MC1_2-7 | 16.8 | 8.6 |
| 3-83-5 | isoamyl-NH- | MC1_2-8 | 17.9 | 8.4 |
| 3-83-6 | isobutyl-NH- | MC1_2-9 | 32.1 | 5.2 |
| 3-83-7 | iPr-NH- | MC1_2-10 | 17.9 | 6.0 |

TABLE 14-continued

T3S inhibition assay results on the 2nd round of MedChem analogs of compound 1 (lead 1)

| ID | Structure | Sample ID | Mean Inhibition (%) | Std. Dev. |
|---|---|---|---|---|
| 3-83-8 | N-methylpiperazine | MC1_2-11 | 22.8 | 3.0 |
| 3-83-9 | 2-methoxyethylamine | MC1_2-12 | 37.6 | 2.4 |
| 3-83-10 | 3-hydroxypropylamine | MC1_2-13 | 23.4 | 8.2 |
| 3-83-11 | morpholine | MC1_2-14 | 4.8 | 10.6 |
| 3-83-12 | piperidine | MC1_2-15 | 8.1 | 7.8 |
| 3-83-13 | pyrrolidine | MC1_2-16 | 25.2 | 3.1 |
| 3-83-14 | benzylamine | MC1_2-17 | 26.0 | 2.8 |
| 3-83-15 | N-methylbenzylamine | MC1_2-18 | 29.3 | 1.2 |
| 3-83-16 | 4-chlorophenethylamine | MC1_2-19 | 50.3 | 6.6 |

We also estimated the IC50 of YopE secretion are estimated as below from a duplicate dose dependent experiment. Among the 19 analogs, the compound with 4-chlorophenylthio group (MC1_2-3) gives the best inhibition activity.

|  | IC50 (μM) |
| --- | --- |
| MC1_2-1 | 30 ± 5 |
| MC1_2-3 | <15 |
| MC1_2-6 | 50 ± 5 |
| MC1_2-9 | 50 ± 10 |
| MC1_2-12 | 50 ± 10 |
| MC1_2-18 | 50 ± 10 |
| MC1_2-19 | 40 ± 5 |

Example 15

Testing Lead 1 Analogs (Round 3) in YopE-Bla Secretion Assay

Figure 20:
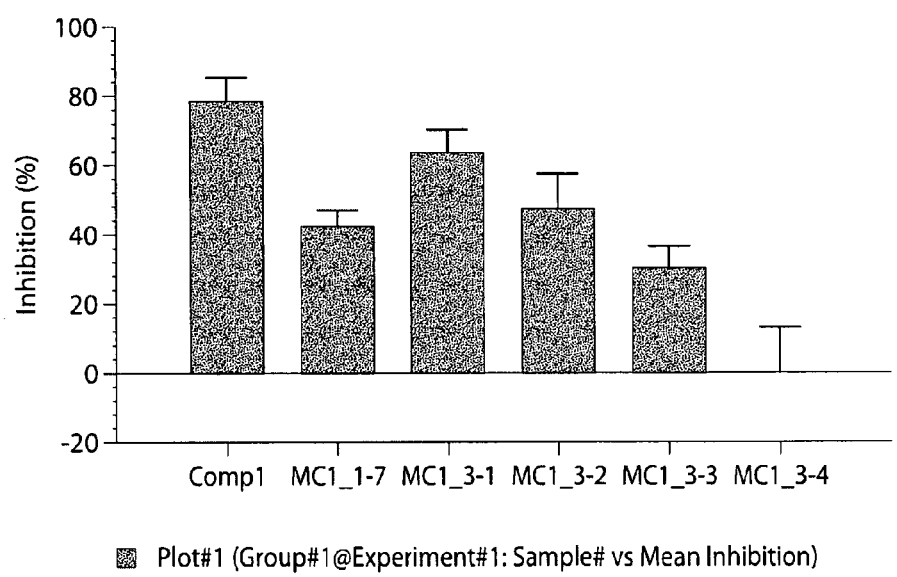
FIG. 20 depicts testing of lead 1 analogs (round 3) in YopE-Bla secretion assay. 60 µM of test compounds were applied to test inhibition (%) of YopE-Bla secretion. The data was collected from a triplicate experiment. The error bars are represented by standard deviations. MC1_3-1, MC1_3-2, and MC1_3-3 showed inhibitory activity, all of which contain a 4-chlorophenylthio moiety. Compound MC3_3-4 is a compound 3 analog.

We tested lead 1 analogs (round 3) in a YopE-Bla secretion assay. 60 μM of each test compound was applied to evaluate inhibition (%) of YopE-Bla secretion. Data was collected from a triplicate experiments as shown in FIG. 20. We also estimated the IC50s of YopE secretion (shown below) from duplicate dose dependent experiments.

|  | IC50 (μM) |
| --- | --- |
| Comp1 | <15 |
| MC1_3-1 | <15 |
| MC1_3-2 | 20 ± 5 |
| MC1_3-3 | 50 ± 5 |

Example 16

Testing Lead 1 Analogs (Round 3) in YopE-Bla Secretion Assay

We tested the 3rd round of MedChem analogs of compound 3 (lead 3) (See, Table 8). We used a concentration of the analogs of 60 μM. The mean inhibition (%) was calculated from an experiment with triplicate samples. Results are show below.

| ID | Mean Inhibition (%) | Std. Dev. |
| --- | --- | --- |
| MC3_3-1 | 69.8 | 47.6 |
| MC3_3-2 | 49.0 | 66.2 |
| MC3_3-3 | 103.4 | 21.7 |
| MC3_3-4 | 0.0 | 26.2 |

Examples 17-25

General Synthetic Methods for Preparing Compounds

Example 17

Compounds 1-31 were synthesized using the following general synthetic procedure in Scheme 1.

Scheme 1

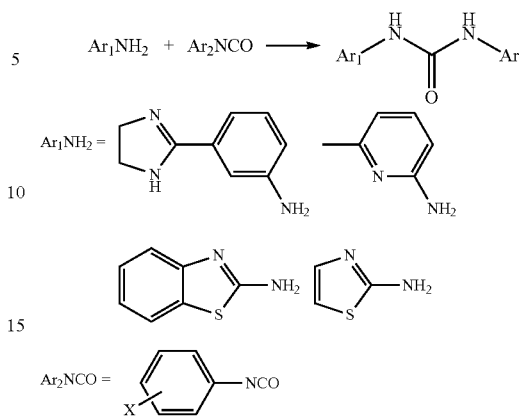

X = 3-CN, 4-COCH$_3$, 3-Cl, 4-Cl, 3-NO$_2$, 3-CF$_3$, 3-Br, 3-CO$_2$CH$_3$, 3-Me, 3,4-OCH$_2$O-3-Cl-4-Me, 3,4-OCH$_2$CH$_2$—, 4-OEt, 3-CF$_3$-4-Cl, 3,5-di-CF$_3$, 4-NO$_2$, 4-CO$_2$Et, 4-Br, 2,5-di-Cl, 2,4-di-Cl, 2-Cl, 2-NO$_2$, 2-Cl-5-CF$_3$, 4-CN, 2-OMe, 2,4-di-F, 2-Me 1-(3-(4,5-dihydro-1H-imidazol-2-yl)phenyl)-3-(4-ethoxyphenyl)urea hydrochloride (18)

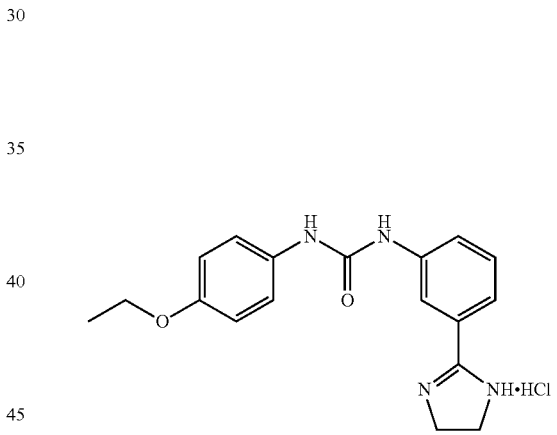

A mixture of 3-(4,5-dihydro-1H-imidazol-2-yl)aniline dihydrochloride monohydrate (stored with 4 A molecular sieves, 48 mg, 0.19 mmol) and 4-ethoxyphenyl isocyanate (33 mg, 0.20 mmol) in dimethylformamide (2 ml) was stirred at room temperature overnight. After removal of the solvent, water (2 ml) was added and the resulting precipitate was collected (18 mg, 64% yield) by filtration. $^1$H NMR (600 MHz, DMSO-d$_6$) δ 10.5 (br s, 1H), 9.12 (br s, 1H), 8.11 (s, 1H), 7.68 (d, 1H, J=8.4 Hz), 7.52 (t, 1H, 8.4 Hz), 7.47 (d, 1H, J=7.2 Hz), 7.35 (d, 2H, J=7.2 Hz), 6.86 (d, 2H, J=7.2 Hz), 3.98 (s, 4H). MS: m/z Calcd 324.4 Found MH$^+$ 325.5

Compounds 1-31 were prepared by a similar procedure of Example 17.

| cpd | name | structure | analytical data |
|---|---|---|---|
| 1 | 1-(3-chlorophenyl)-3-(3-(4,5-dihydro-1H-imidazol-2-yl)phenyl)urea hydrochloride | 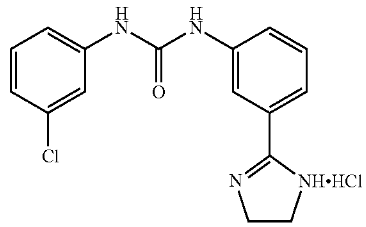 | MS: m/z Calcd 314.7 Found MH⁺ 315.4 |
| 2 | 1-(3-(4,5-dihydro-1H-imidazol-2-yl)phenyl)-3-phenylurea hydrochloride | 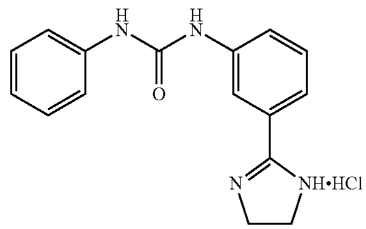 | MS: m/z Calcd 280.3 Found MH⁺ 281.5 |
| 3 | 1-(3-cyanophenyl)-3-(4,5-dihydro-1H-imidazol-2-yl)phenyl)urea hydrochloride | 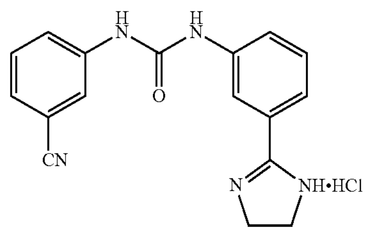 | MS: m/z Calcd 305.3 Found MH⁺ 306.4 |
| 4 | 1-(4-acetylphenyl)-3-(3-(4,5-dihydro-1H-imidazol-2-yl)phenyl)urea hydrochloride | 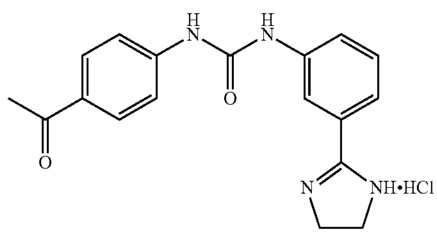 | MS: m/z Calcd 322.4 Found MH⁺ 323.3 |
| 5 | 1-(6-methylpyridin-2-yl)-3-phenylurea | 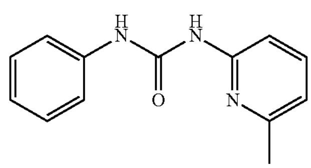 [SMILES: Cc1cccc(NC(=O)Nc2ccccc2)n1] | MS: m/z Calcd 227.3 Found MH⁺ 228.3 |
| 6 | 1-(3-(4,5-dihydro-1H-imidazol-2-yl)phenyl)-3-(3-nitrophenyl)urea hydrochloride | 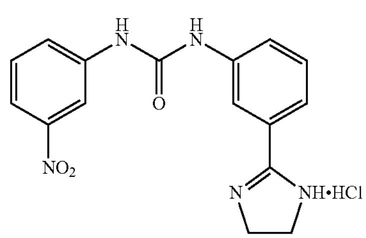 | ¹H NMR (600 MHz, DMSO-d₆) δ 10.5 (br s, 1H), 8.63 (s, 1H), 8.17 (s, 1H), 7.86-7.84 (m, 1H), 7.77-7.76 (m, 1H), 7.69 (d, 1H, J = 8.4 Hz), 7.60-7.56 (m, 2H), 7.53 (d, 1H, J = 8.4 Hz), 3.99 (s,4H). MS: m/z Calcd 325.3 Found MH⁺ 326.3 |
| 7 | 1-(3-(4,5-dihydro-1H-imidazol-2-yl)-3-(3-trifluorophenyl)urea hydrochloride | 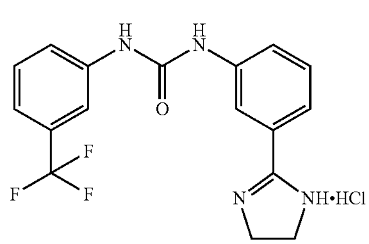 | MS: m/z Calcd 348.3 Found MH⁺ 349.3 |

-continued

| cpd | name | structure | analytical data |
|---|---|---|---|
| 8 | 1-(3-bromophenyl)-3-(3-(4,5-dihydro-1H-imidazol-2-yl)phenyl)urea hydrochloride | 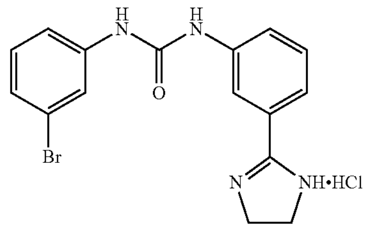 | MS: m/z Calcd 359.2 Found MH⁺ 359.2/360.3 |
| 9 | 1-(benzo[d]thiazo-2-yl)-3-phenylurea | 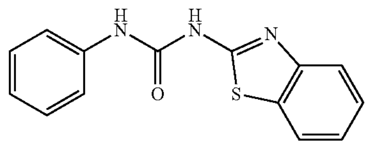 [SMILES: O=C(Nc1ccccc1)Nc1nc2ccccc2s1] | MS: m/z Calcd 269.3 Found MH⁺ 270.3 |
| 10 | 1-phenyl-3-(thiazol-2-yl)-3-phenylurea | 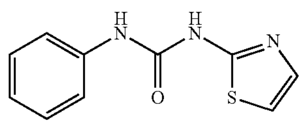 [SMILES: O=C(Nc1ccccc1)Nc1nccs1] | $^1$H NMR (600 MHz, DMSO-d$_6$) δ 10.5 (brs, 1H), 8.94 (s, 1H), 7.46 (d, 2H, J = 7.8 Hz), 7.37 (d, 1H, J = 3.6 Hz), 7.31 (t, 2H, J = 7.8 Hz), 7.11 (s, 1H), 7.03 (t, 1H, J = 7.2 Hz). MS: m/z Calcd 219.3 Found MH⁺ 220.2 |
| 11 | methyl 3-(3-(3-(4,5-dihydro-1H-imidazol-2-yl)phenyl)ureido)benzoate hydrochloride | 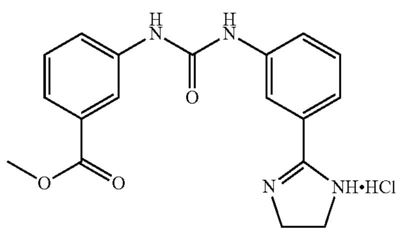 | $^1$H NMR (600 MHz, DMSO-d$_6$) δ 10.5 (br s, 1H), 9.50 (br s, 1H), 8.26 (s, 1H), 8.17 (s, 1H), 7.67-7.55 (m, 4H), 7.49 (d, 1H, J = 7.2 Hz), 7.46 (t, 1H, J = 7.8 Hz), 4.0 (s, 4H), 3.85 (s, 3H). MS: m/z Calcd 338.4 Found MH⁺ 339.4 |
| 12 | 1-(benzo[d][1,3]dioxol-5-yl)-3-(3-4,5-dihydro-1H-imidazol-2-yl)phenyl)urea hydrochloride | 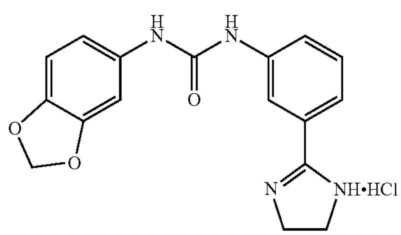 | MS: m/z Calcd 324.3 Found MH⁺ 325.3 |
| 13 | 1-(3-chloro-4-methylphenyl)-3-(3-(4,5-dihydro-1H-imidazol-2-yl)phenyl)urea hydrochloride | 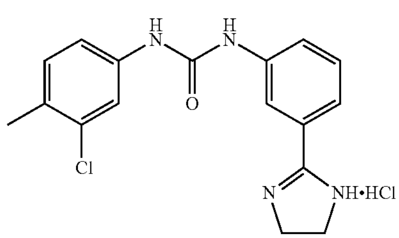 | $^1$H NMR (600 MHz, DMSO-d$_6$) δ 10.5 (br s, 1H), 9.4 (br s, 1H), 8.14 (s, 1H), 7.73 (s, 1H), 7.66 (d, 1H, J = 8.4 Hz), 7.56 (t, 1H, J = 8.4 Hz), 7.49 (d, 1H, J = 7.8 Hz), 7.25 (d, 1H, J = 8.4 Hz), 7.20 (dd, 1H, J = 8.4, 1.8 Hz), 3.99 (s, 4H), 2.27 (s, 3H). MS: m/z Calcd 328.8 Found MH⁺ 329.3 |

-continued

| cpd | name | structure | analytical data |
|---|---|---|---|
| 14 | 1-(3-(4,5-dihydro-1H-imidazol-2-yl)phenyl)-3-(2,3-dihydrobenzofuran-5-yl)urea hydrochloride | 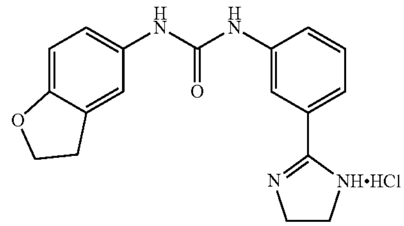 | $^1$H NMR (600 MHz, DMSO-d$_6$) δ 10.5 (br s, 1H), 9.41 (br s, 1H), 9.07 (br s, 1H), 8.11 (s, 1H), 7.67 (d, 1H, J = 8,4 Hz), 7.53 (t, 1H, J = 8.4 Hz), 7.46 (d, 1H, J = 8.4 Hz), 7.37 (s, 1H), 7.11 (dd, 1H, J = 9, 2.4 Hz), 6.67 (d, 1H, J = 8.4 Hz), 4.47 (t, 2H, J = 9 Hz), 3.99 (s, 4H), 3.15 (t, 2H, J = 9 Hz). MS: m/z Calcd 322.4 Found MH$^+$ 323.3 |
| 15 | 1-93-(4,5-dihydro-1H-imidazol-2-yl)phenyl)-3-m-tolylurea hydrochloride | 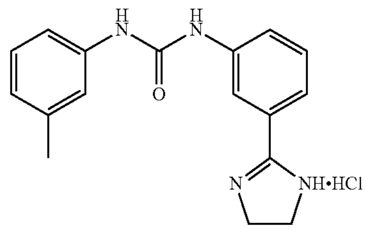 | MS: m/z Calcd 294.4 Found MH$^+$ 295.3 |
| 16 | 1-(3-(4,5-dihydro-1H-imidazol-2-yl)phenyl)-3-phenylthiourea hydrochloride | 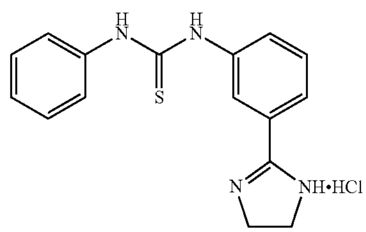 | MS: m/z Calcd 296.4 Found MH$^+$ 297.4 |
| 17 | 1-(4-chloro-3-(trifluoromethyl)phenyl)-3-(3-(4,5-dihydro-1H-imidazol-2-yl)phenyl)urea hydrochloride | 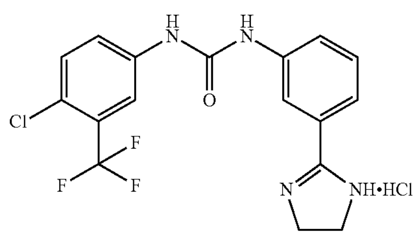 | $^1$H NMR (600 MHz, DMSO-d$_6$) δ 10.4 (br s, 1H), 9.58 (br s, 1H), 8.17-8.09 (m, 2H), 7.68-7.62 (m, 3H), 7.57 (t, 1H, J = 7.8 Hz), 7.51(d, 1H, J = 7.8 Hz), 3.99 (s, 4H). MS: m/z Calcd 382.8 Found MH$^+$ 383.9 |
| 19 | 1-(3,5-bis(trifluoromethyl)phenyl)-3-(3-(4,5-dihydro-1H-imidazol-2-yl)phenyl)urea hydrochloride | 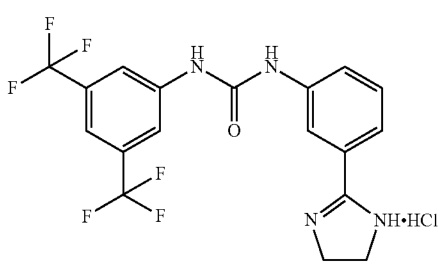 | $^1$H NMR (600 MHz, DMSO-d$_6$) δ 10.2 (br s, 1H), 10.0 (s, 1H), 9.61 (s, 1H), 8.17-8.14 (m, 3H), 7.70-7.67 (m, 2H), 7.56-7.51 (m, 1H), 3.98 (s, 4H). MS: m/z Calcd 416.3 Found MH$^+$ 417.0 |
| 20 | 1-(3-(4,5-dihydro-1H-imidazol-2-yl)phenyl)-3-(4-nitrophenyl)urea hydrochloride | 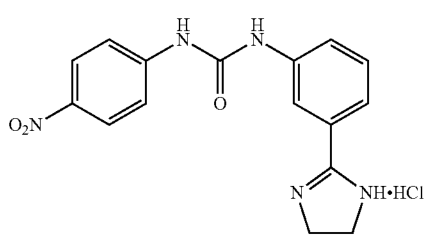 | 10.4 (br s, 1H), 9.60 (br s, 1H), 8.21 (d, 2H, J = 9 Hz), 8.13 (s, 1H), 7.72 (d, 2H, J = 9 Hz), 7.72-7.70 (m, 1H), 7.58 (t, 1H, J = 7.8 Hz), 7.52 (d. 1H, J = 7.8 Hz), 3.99 (s, 4H). MS: m/z Calcd 325.3 Found MH$^+$ 326.0 |

| cpd | name | structure | analytical data |
|---|---|---|---|
| 21 | ethyl 4-(3-(3-(4,5-dihydro-1H-imidazol-2-yl)phenyl)ureido)benzoate hydrochloride | 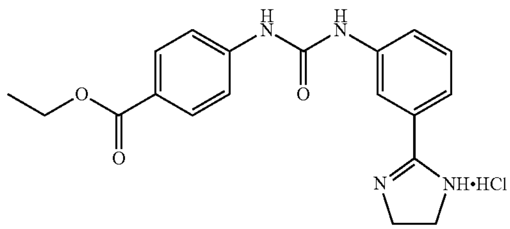 | $^1$H NMR (600 MHz, DMSO-$d_6$) δ 10.5 (br s, 1H), 9.36 (br s, 1H), 8.15 (s, 1H), 7.92-7.89 (m, 2H), 7.65 (d, 1H, J = 8.4 Hz), 7.60-7.56 (m, 3H), 7.50 (d, 1H, 7.8 Hz), 4.28 (q, 2H, J = 6 Hz), 3.99 (s, 4H), 1.31 (t, 3H, J = 6.6 Hz). MS: m/z Calcd 352.4 Found MH$^+$ 353.0 |
| 22 | 1-(4-bromophenyl)-3-(3-(4,5-dihydro-1H-imidazol-2-yl)phenyl)urea hydrochloride | 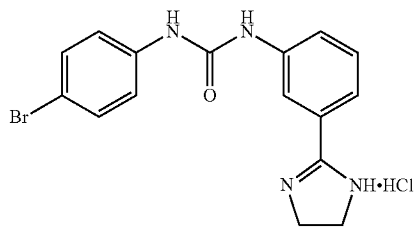 | $^1$HNMR (600 MHz, DMSO-$d_6$) δ 10.5 (br s, 1H), 8.80 (d, 2H, J = 9 Hz), 7.91 (s, 1H), 7.55 (d, 1H, J = 7.8Hz), 7.45 (d, 2H, J = 8.4 Hz), 7.39 (d, 1H, J = 7.8 Hz), 7.32 (t, 1H, J = 7.8 Hz), 3.99 (s, 4H). MS: m/z Calcd 359.2 Found MH$^+$ 360.9/361.9 |
| 23 | 1-(2,5-dichlorophenyl)-3-(3-(4,5-dihydro-1H-imidazol-2-yl)phenyl)urea hydrochloride | 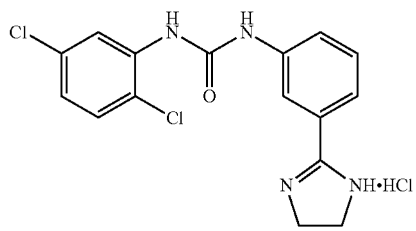 | $^1$H NMR (600 MHz, DMSO-$d_6$) δ 9.94 (br s, 1H), 9.3 (s, 1H), 8.32 (d, 1H, J = 2.4 Hz), 8.22 (d, 1H, J = 2.4 Hz), 7.60 (d, 1H, J = 7.2 Hz), 7.53-7.49 (m, 2H), 7.15 (dd, 2H, J = 8.4, 2.4 Hz), 3.92 (s, 4H). MS: m/z Calcd 349.2 Found MH$^+$ 350.9 |
| 24 | 1-(2,4-dichlorophenyl)-3-(3-(4,5-dihydro-1H-imidazol-2-yl)phenyl)urea hydrochloride | 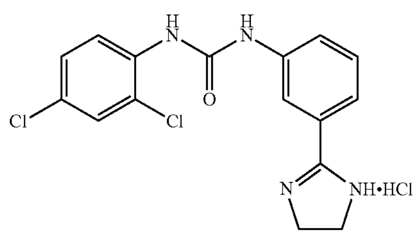 | $^1$H NMR (600 MHz, DMSO-$d_6$) δ 10.5 (br s, 1H), 10.2 (s, 1H), 9.18 (s, 1H), 8.16-8.14 (m, 1H), 7.71 (d, 1H, J = 7.8 Hz), 7.64 (d, 1H, J = 2.4 Hz), 7.56-7.53 (m, 2H), 7.41-7.40 (m, 1H), 4.0 (s, 4H). MS: m/z Calcd 349.2 Found MH$^+$ 350.9 |
| 25 | 1-(2-chlorophenyl)-3-(3-(4,5-dihydro-1H-imidazol-2-yl)phenyl)urea hydrochloride | 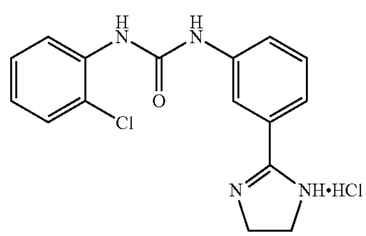 | MS: m/z Calcd 314.8 Found MH$^+$ 315.0 |
| 26 | 1-(3-(4,5-dihydro-1H-imidazol-2-yl)phenyl)-3-(2-nitrophenyl)urea hydrochloride | 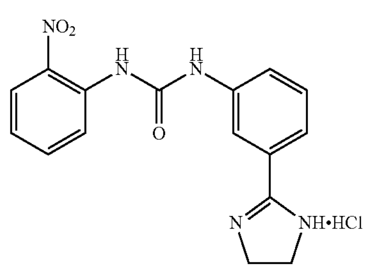 | $^1$H NMR (600MHz, DMSO-$d_6$) δ 10.2 (br s, 1H), 10.0 (s, 1H), 9.69 (br s, 1H), 8.12-8.10 (m, 1H), 8.03 (dd, 1H, J = 8.4, 1.2 Hz), 7.95 (d, 1H, 9 Hz), 7.72-7.67 (m, 2H), 7.30-7.28 (m, 2H), 3.97 (s, 4H). MS: m/z Calcd 325.3 Found MH$^+$ 326.0 |

-continued

| cpd | name | structure | analytical data |
|---|---|---|---|
| 27 | 1-(2-chloro-5-(trifluoromethyl)phenyl)-3-(3-(4,5-dihydro-1H-imidazol-2-yl)phenyl)urea hydrochloride | 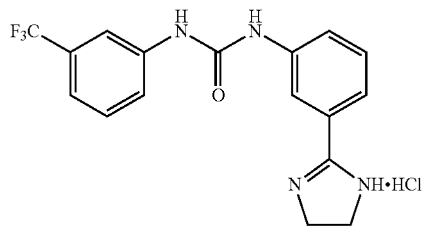 | ¹H NMR (600 MHz, DMSO-d₆) δ 10.4 (br s, 1H), 8.89-8.83 (m, 1H), 8.63 (s, 1H), 8.20 (s, 1H), 7.76-773 (m, 1H), 7.68-7.55 (m, 1H), 7.58 (t, 1H, J = 7.8 Hz), 7.54 (d, 1H, J = 7.8 Hz), 7.44 (dd, 1H, J = 7.8, 2.4 Hz), 3.99 (s, 4H). MS: m/z Calcd 382.8 Found MH⁺ 383.0 |
| 28 | 1-(4-cyanophenyl)-3-(3-(4,5-dihydro-1H-imidazol-2-yl)phenyl)urea hydrochloride | 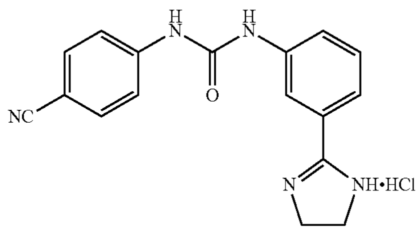 | ¹H nMR (600 MHz, DMSO-d₆) δ 10.4 (s, 1H), 9.61 (s, 1H), 8.11 (s, 1H), 7.74 (d, 2H, J = 9 Hz), 7.72-7.70 (m, 1H), 7.66 (d, 2H, J = 9 Hz), 7.58 (t, 1H, J = 7.2 Hz), 7.51 (d, 1H, J = 7.2 Hz), 4.0 (s, 4H). MS: m/z Calcd 305.3 Found MH⁺ 306.0 |
| 29 | 1-(3-(4,5-dihydro-1H-imidazol-2-yl)phenyl)-3-(2-methozyphenyl)urea hydrochloride | 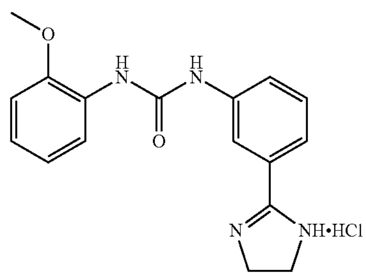 | ¹H NMR (600 MHz, DMSO-d₆) δ (s, 1H), 9.85 (d, 1H, J = 7.2 Hz), 8.44 (s, 1H), 8.16 (s, 1H), 8.13-8.09 (m, 1H), 7.65 (d, 1H, J = 7.8 Hz), 7.54 (t, 1H, J = 7.2 Hz), 7.49 (d, 1H, J = 6.6 Hz), 7.03-6.89 (m, 3H), 3.99 (s,4H), 3.83 (s, 3H). MS: m/z Calcd 310.4 Found MH⁺ 311.0 |
| 30 | 1-(2,4-difluorophenyl)-3-(3-(4,5-dihydro-1H-imidazol-2-yl)phenyl)urea hydrochloride | 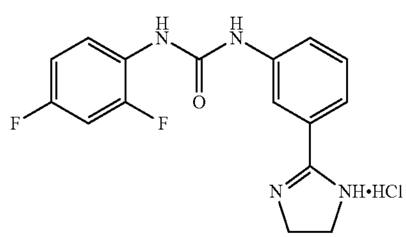 | ¹HNMR (600 MHz, DMSO-d₆) δ 10.5 (s, 1H), 9.74 (s, 1H), 8.88 (s, 1H), 8.10 (s, 1H), 8.08-8.02 (m, 1H), 7.70 (d, 1H, J = 7.8 Hz), 7.56 (t, 1H, J = 8.4 Hz), 7.51 (d, 1H, J = 7.8 Hz), 7.34-7.29 (m, 1H), 7.08-7.04 (m, 1H), 3.99 (s, 4H). MS: m/z Calcd 316.3 Found MH⁺ 317.0 |
| 31 | 1-(3-4,5-dihydro-1H-imidazol-2-yl)phenyl)-3-o-tolylurea hydrochloride | 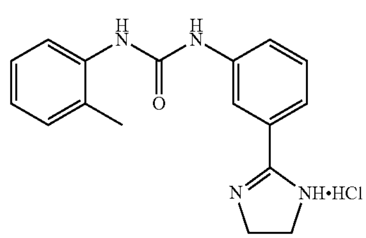 | ¹H NMR (600 MHz, DMSO-d₆) δ 10.4 (s, 1H), 9.42 (s, 1H), 8.26 (s, 1H), 8.06 (s, 1H), 7.83-7.79 (m, 2H), 7.47-7.42 (m, 1H), 7.19-7.12 (m, 2H), 6.98-6.93 (m, 1H), 3.82 (s, 4H), 2.22 (s, 3H). MS: m/z Calcd 294.4 Found MH⁺ 295.0 |

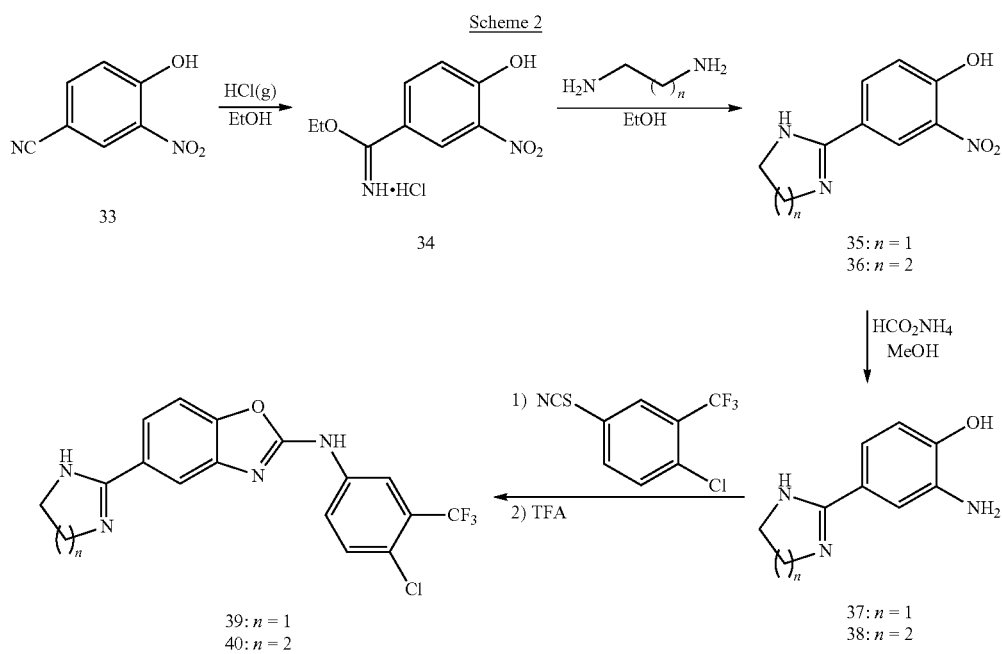

Example 18

N-(4-chloro-3-(trifluoromethyl)phenyl)-5-(4,5-dihydro-1H-imidazol-2-yl)benzo[d]oxazol-2-amine (39)

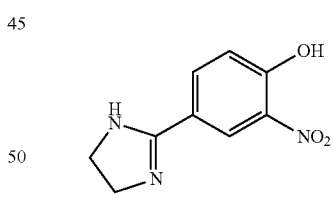

Step 1

Synthesis of ethyl 4-hydroxy-3-nitrobenzimidate hydrochloride (34)

A stirred mixture of 4-hydroxy-3-nitrobenzonitrile 33 (5.2 g, 32 mmol) in a solution of abs. ethanol (250 ml) and dioxane (40 ml) was cooled in an ice bath as dry HCl gas was bubbled through it for 1 hr. The mixture was stirred overnight at room temperature and the resulting precipitate was collected, washed with ether and dried to give 6.2 g (79%) of the imidate ester HCl 34. $^1$H NMR (600 MHz, DMSO-$d_6$) δ 11.8 (br s, 1H), 8.64 (s, 1H), 8.21 (d, 1H, J=9 Hz), 7.38 (d, 1H, J=9 Hz), 4.57 (q, 2H, J=7.2 Hz), 1.47 (t, 3H, J=7.2 Hz).

Step 2

Synthesis of 4-(4,5-dihydro-1H-imiazol-2-yl)-2-nitrophenol (35)

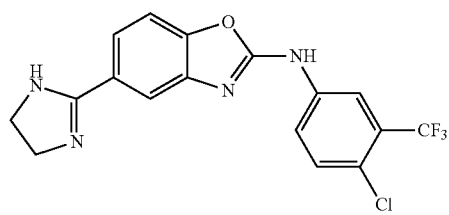 [SMILES: FC(F)(F)c1cc(Nc2nc3cc(C4=NCCN4)ccc3o2)ccc1Cl]

To a solution of the imidate ester HCl 34 (650 mg, 2.63 mmol) in abs. ethanol was added ethylenediamine (0.53 ml, 7.89 mmol) at 0° C. and the mixture was stirred for 16 hrs at room temperature. Ether was added and the resulting precipitates were collected by filtration and dried in vacuo to give 490 mg (90% yield) of the desired cyclic amidine 35. $^1$H NMR (600 MHz, DMSO-$d_6$) δ 8.38 (d, 1H, J=3 Hz), 7.45 (dd, 1H, J=9, 2.4 Hz), 3.79 (s, 4H).

Step 3

Synthesis of 2-amino-4-(4,5-dihydro-1H-imidazol-2-yl)phenol (37)

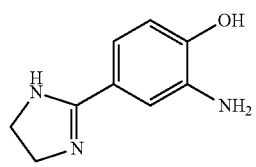 [SMILES: Nc1cc(C2=NCCN2)ccc1O]

A mixture of the cyclic amidine 35 (490 mg, 2.36 mmol), ammonium formate (1.5 g, 23.6 mmol) and 10% Pd on carbon (50 mg) in methanol was heated at reflux for 4 hrs. After cooling to room temperature, the catalyst was removed by filtration through celite and the filtrate was concentrated in vacuo. The residue was triturated with hexane and the resulting solid was collected to yield 309 mg (74%) of the desired product 37. $^1$H NMR (600 MHz, DMSO-$d_6$) δ 7.07 (d, 1H, J=1.8 Hz), 6.94 (dd, 1H, J=7.8, 1.8 Hz), 6.64 (d, 1H, J=7.8 Hz), 5.46 (br s, 2H), 4.69 (br s, 1H), 2.64 (s, 4H). MS: m/z Calcd 177.2 Found MH$^+$ 173.3

Step 4

Synthesis of N-(4-chloro-3-(trifluoromethyl)phenyl)-5-(4,5-dihydro-1H-imidazol-2-yl)benzo[d]oxazol-2-amine (39)

To a solution of 37 (178 mg, 1.0 mmol) in methanol was added 4-chloro-3-trifluoromethyl isothiocyanate (0.21 ml, 1.3 mmol) at room temperature and the mixture was stirred for 6 hrs, concentrated in vacuo, and purified by flash chromatography eluting with 10% methanol in dichloromethane to afford 250 mg of the desired thiourea (MS: m/z Calcd 414.8 Found 415.1) which was dissolved in dichloromethane (5 ml) and treated with trifluoroacetic acid (2 ml). After heating at reflux overnight, the mixture was cooled, concentrated in vacuo, and purified by flash chromatography eluting with 10% methanol in dichloromethane to afford 30 mg (8% yield for 2 steps) of the desired product 39. MS: m/z Calcd 380.8 Found MH$^+$ 381.1

N-(4-chloro-3-(trifluoromethyl)phenyl)-5-(1,4,5,6-tetrahydropyrimidin-2-yl)benzo[d]oxazol-2-amine (40)

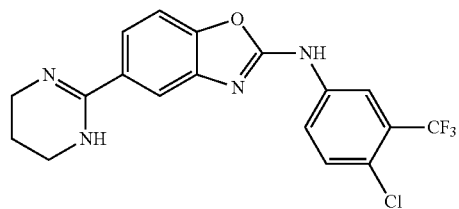 [SMILES: FC(F)(F)c1cc(Nc2nc3cc(C4=NCCCN4)ccc3o2)ccc1Cl]

This compound was similarly prepared according to the procedure for Example 18 (39). MS: m/z Calcd 394.8 Found MH$^+$ 395.1

Scheme 3

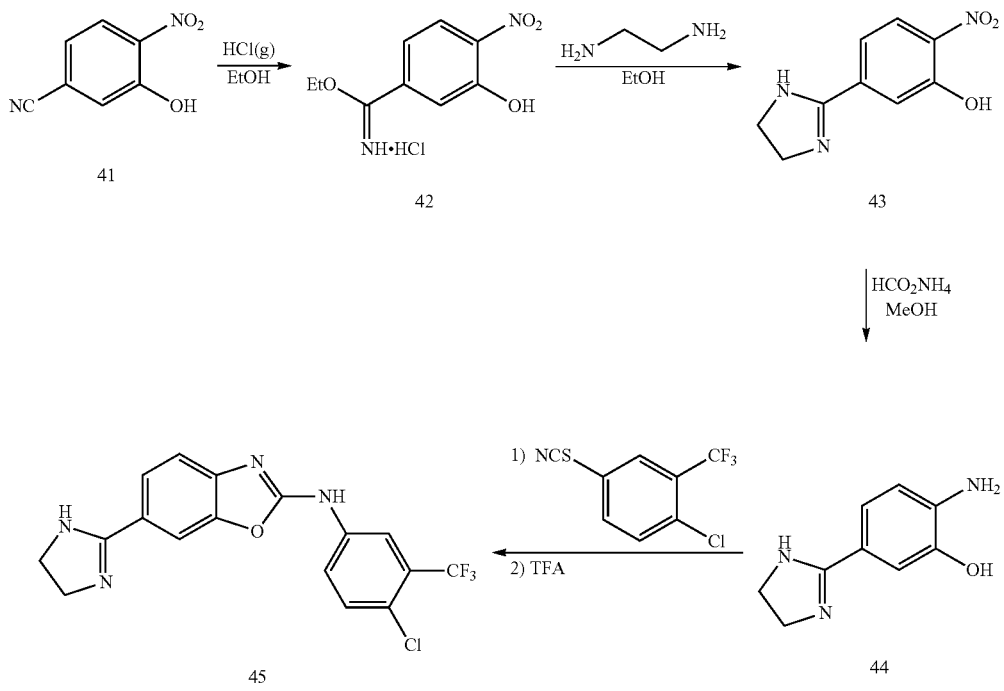

Example 19

N-(4-chloro-3-(trifluoromethyl)phenyl)-6-(4,5-dihydro-1H-imidazol-2-yl)benzo[d]oxazol-2-amine (45)

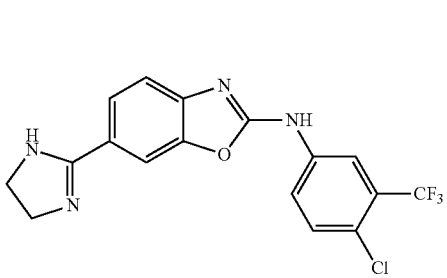 [SMILES: FC(F)(F)c1cc(Nc2nc3ccc(C4=NCCN4)cc3o2)ccc1Cl]

This compound was similarly prepared, starting from 3-hydroxy-4-nitrobenzonitrile 41, according to the procedure for Example 18 (39). MS: m/z Calcd 394.8 Found MH+ 395.0

Example 20

N-(4-chloro-3-(trifluoromethyl)phenyl)-6-(4,5-dihydro-1H-imidazol-2-yl)-1H-benzo[d]imidazol-2-amine (49)

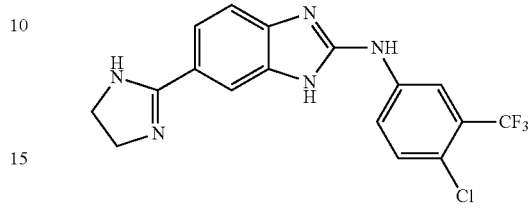

To a stirred solution of 1,1'-thiocarbonyldiimidazole (155 mg, 0.87 mmol), imidazole (12 mg, 0.17 mmol) in acetonitrile (5 ml) at 0° C. was added a solution of 4-chloro-3-trifluoromethylaniline (113 mg, 0.58 mmol) in acetonitrile (2 ml) dropwise. To this was added 4-(4,5-dihydro-1H-imidazol-2-yl)benzene-1,2-diamine 48 (102 mg, 0.58 mmol), which was prepared from 46 in a manner similar to that Scheme 4

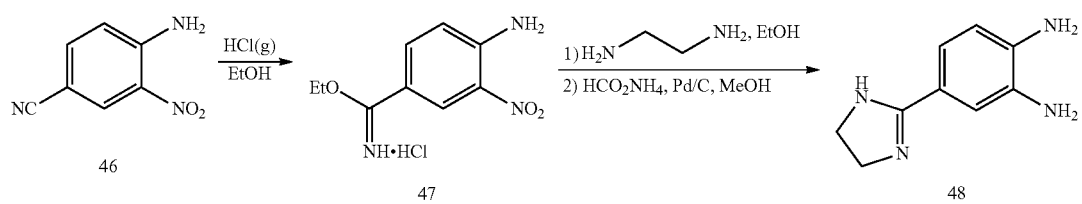

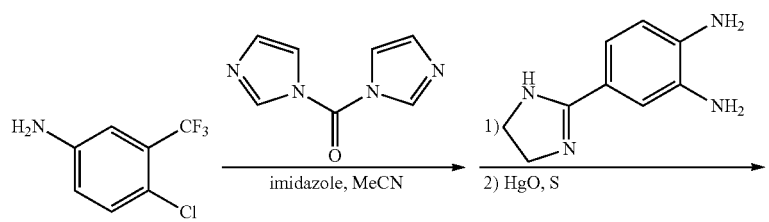

described in Example 18 similarly according to the procedure described in Example 18). The mixture was heated for 3 hrs at 50° C. and concentrated in vacuo. The residue was purified by flash chromatography eluting with 10% methanol in dichloromethane to afford the thiourea (220 mg, 92%). MS: m/z Calcd 413.9 Found MH+ 414.3

A mixture of the thiourea (220 mg, 0.53 mmol), HgO (230 mg, 1.1 mmol), sulfur (3 mg, 0.11 mmol) in ethanol was refluxed for 3 hrs. After cooling to room temperature, the reaction mixture was filtered through celite, concentrated in vacuo, and the residue was purified by flash chromatography eluted with 15% methanol in dichloromethane to afford 26 mg (13%) of the desired product 49. MS: m/z Calcd 379.8 Found MH+ 380.1

Step 1

Synthesis of 6-chloro-5-cyanopicolinic acid (51)

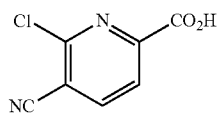

Scheme 5

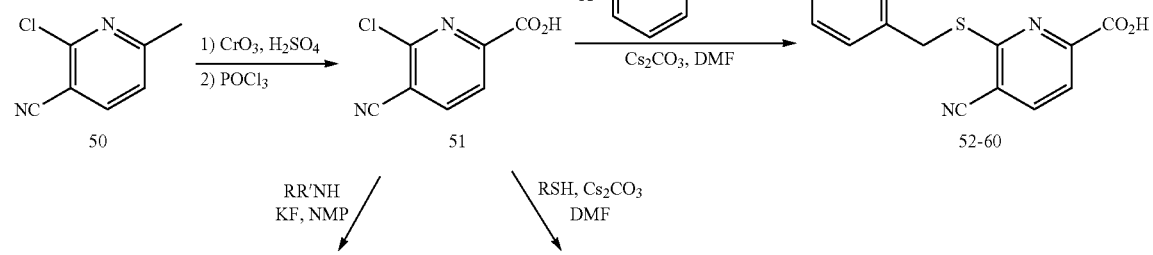

X = 2-Cl, 3-Me, 3-NO2, 4-OMe, 4-Me, 4-CF3, 4-Cl, 4-OCF3, 4-H
R = i-Pr, cyclohexyl, 4-Cl-phenyl Example 21

6-(4-chlorobenzylthio)-5-cyanopicolinic acid (52)

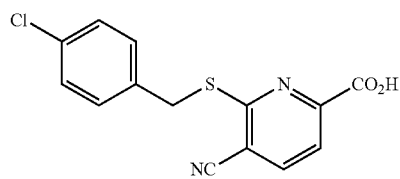 [SMILES: N#Cc1ccc(C(=O)O)nc1SCc1ccc(Cl)cc1]

To a solution of 6-chloro-5-cyano-2-picoline 50 (3.0 g, 20 mmol) in conc-H2SO4 (20 ml) was added CrO3 (4.9 g, 49 mmol) portionwise over 2 hr period while the reaction mixture was kept below 20° C. After stirring overnight at room temperature, the mixture was poured into ice-water and the resulting solid was collected by filtration to give the crude 6-chloro-5-(aminocarbonyl)-2-picolinic acid which was dissolved in POCl3 (15 ml). After heating at reflux for 30 min, the reaction mixture was concentrated in vacuo and the residue was treated with ice water. The precipitate was collected by filtration to afford 2.5 g (71% for 2 steps) of the desired product 51. 1H NMR (600 MHz, DMSO-d6) δ 8.65 (δ, 1H, θ=7.8 Hζ), 8.17 (δ, 1H, θ=7.8 Hζ)

Step 2

Synthesis of 6-(4-chlorobenzylthio)-5-cyanopicolinic acid (52)

A mixture of 6-chloro-5-cyanopicolinic acid (30 mg, 0.16 mmol), 4-chlorophenyl methanethiol (24 ul, 0.18 mmol), and $CsCO_3$ (156 mg, 0.48 mmol) in dimethylformamide (2 ml) was heated for 16 hrs at 45° C. After removal of the solvent, the residue was treated with water (2 ml) and acidified with 1N—HCl to pH2. The precipitate was collected by filtration and dried under vacuum to afford 40 mg (82%) of the desired product 52. $^1$H NMR (600 MHz, DMSO-$d_6$) δ 13.6 (br s, 1H), 8.46 (d, 1H, J=7.8 Hz), 8.15 (d, 1H, J=7.8 Hz), 7.55 (d, 2H, J=9 Hz), 7.47 (d, 2H, J=9 Hz). MS: m/z Calcd 304.8 Found MH$^+$ 305.0

Compounds 53-63 were prepared by a similar procedure of Example 21.

| cpd | name | structure | analytical data |
|---|---|---|---|
| 53 | 6-(benzylthio)-5-cyanopicolinic acid | 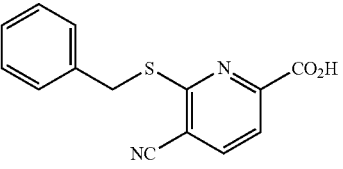 [SMILES: N#Cc1ccc(C(=O)O)nc1SCc1ccccc1] | $^1$H NMR (600 MHz, DMSO-$d_6$) δ 13.9 (br s, 1H), 8.37 (d, 1H, J = 7.8 Hz), 7.86 (d, 1H, J = 7.8 Hz), 7.55 (d, 1H, J = 7.2 Hz), 7.34-7.24 (m, 3H), 4.60 (s, 2H). MS: m/z Calcd 270.3 Found MH$^+$ 271.0 |
| 54 | 6-(2-chlorobenzylthio)-5-cyanopicolinic acid | 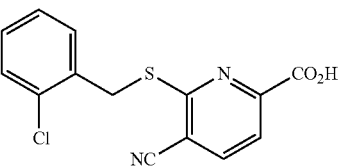 [SMILES: N#Cc1ccc(C(=O)O)nc1SCc1ccccc1Cl] | $^1$H NMR (600 MHz, DMSO-$d_6$) δ 8.26 (d, 1H, J = 7.8 Hz), 8.00 (d, 1H, J = 7.2 Hz), 7.74 (d, 1H, J = 8.4 Hz), 7.47 (d, 1H, 7.2 Hz), 7.39-7.33 (m, 1H), 7.29 (t, 1H, J = 7.2 Hz), 7.23 (t, 1H, J = 7.2 Hz).4.63 (s, 2H). MS: m/z Calcd 304.8 Found MH$^+$ 305.0 |
| 55 | 5-cyano-6-(3-methylbenzylthio) picolinic acid | 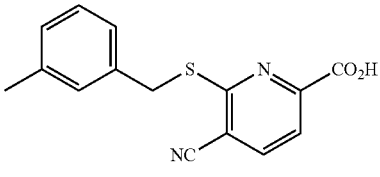 [SMILES: Cc1cccc(CSc2nc(C(=O)O)ccc2C#N)c1] | $^1$H NMR (600 MHz, DMSO-$d_6$) δ 13.9 (br s, 1H), 8.37 (d, 1H, J = 7.8 Hz), 7.85 (d, 1H, J = 7.8 Hz), 7.42 (s, 1H), 7.31 (d, 1H, J = 7.8 Hz), 7.17 (t, 1H, J = 7.8 Hz), 7.04 (d, 1H, J = 7.8 Hz), 4.54 (s, 2H), 2.30 (s, 3H). MS: m/z Calcd 284.3 Found MH$^+$ 285.0 |
| 56 | 5-cyano-6-(3-nitrobenzylthio) picolinic acid | 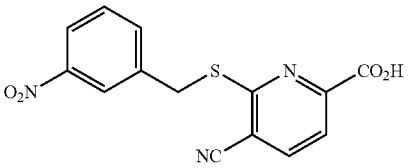 [SMILES: N#Cc1ccc(C(=O)O)nc1SCc1cccc([N+](=O)[O-])c1] | $^1$H NMR (600 MHz, DMSO-$d_6$) δ 13.9 (br s, 1H), 8.37 (d, 1H, J = 7.8 Hz), 7.85 (d, 1H, J = 7.8 Hz), 7.46 (s, 1H), 7.20 (d, 1H, J = 8.4 Hz), 6.90-6.83 (m, 2H), 4.62 (s, 2H). MS: m/z Calcd 315.3 Found MH$^+$ 316.0 |
| 57 | 5-cyano-6-(4-methoxybenzylthio) picolinic acid | 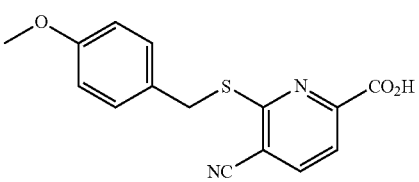 [SMILES: COc1ccc(CSc2nc(C(=O)O)ccc2C#N)cc1] | 1H NMR (600 MHz, DMSO-d6) δ 13.9 (brs, 1H), 8.36 (d, 1H, J = 7.8 Hz), 7.85 (d, 1H, J = 7.8 Hz), 7.46 (d, 2H, J = 8.4 Hz), 6.84 (d, 2H, J = 8.4 Hz), 4.54 (s, 2H), 3.71 (s, 3H). MS: m/z Calcd 300.3 Found MH$^+$ 323.0 (Na+) |
| 58 | 5-cyano-6-(4-methylbenzylthio) picolinic acid | 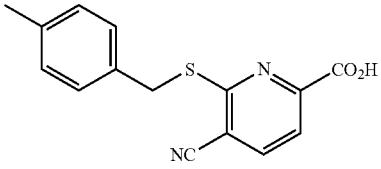 [SMILES: Cc1ccc(CSc2nc(C(=O)O)ccc2C#N)cc1] | MS: m/z Calcd 284.3 Found MH$^+$ 285.0 |

-continued

| cpd | name | structure | analytical data |
|---|---|---|---|
| 59 | 5-cyano-6-(4-trifluoromethyl)benzylthio)picolinic acid | 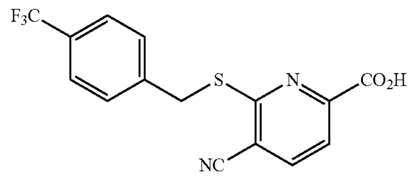 [SMILES: N#Cc1ccc(C(=O)O)nc1SCc1ccc(C(F)(F)F)cc1] | ¹H NMR (600 MHz, DMSO-d₆) δ 13.0 (br s, 1H), 8.36 (d, 1H, J = 8.4 Hz), 7.84 (d, 1H, J = 7.8 Hz), 7.42 (d, 2H, J = 7.8 Hz), 7.10 (d, 2H, J = 7.8), 4.54 (s, 2H). MS: m/z Calcd 338.3 Found MH⁺ 339.0 |
| 60 | 5-cyano-6-(4-(trifluoromethoxy)benzylthio)picolinic acid | 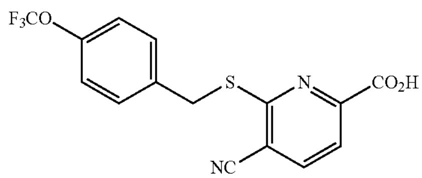 [SMILES: N#Cc1ccc(C(=O)O)nc1SCc1ccc(OC(F)(F)F)cc1] | ¹H NMR (600 MHz, DMSO-d₆) δ 9.57 (d, 1H, J = 7.8 Hz), 9.23 (d, 1H, J = 7.8 Hz), 9.02 (d, 2H, J = 7.2 Hz), 8.51 (d, 2H, J = 7.8 Hz), 5.94 (s, 2H). MS: m/z Calcd 354.3 Found MH⁺ 355.0 |
| 61 | 5-cyano-6-(isopropylthio)picolinic acid | 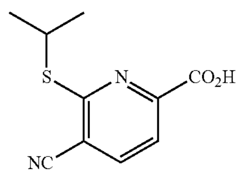 | ¹H NMR (600 MHz, DMSO-d₆) δ 13.8 (br s, 1H), 8.36 (d, 1H, J = 7.8 Hz), 7.82 (d, 1H, J = 8.4 Hz), 4.15 (septet, 1H, J = 7.2 Hz), 1.42 (d, 6H, J = 7.2 Hz). MS: m/z Calcd 222.3 Found MH⁺ 223.3 |
| 62 | 5-cyano-6-(cyclohexylthio)picolinic acid | 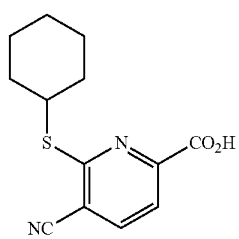 [SMILES: N#Cc1ccc(C(=O)O)nc1SC1CCCCC1] | ¹H NMR (600 MHz, DMSO-d₆) δ 13.7 (br s, 1H), 8.35 (d, 1H, J = 7.8 Hz), 7.80 (d, 1H, J = 7.8 Hz), 4.07-4.04 (m, 1H), 2.08-2.02 (m, 2H), 1.74-1.69 (m, 2H), 1.57-1.26 (m, 6H). MS: m/z Calcd 262.3 Found MH⁺ 263.2 |
| 63 | 6-(4-chlorophenylthio)-5-cyanopicolinic acid | 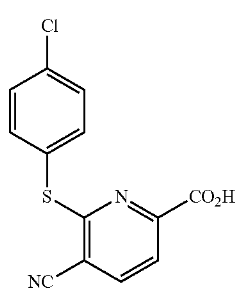 [SMILES: N#Cc1ccc(C(=O)O)nc1Sc1ccc(Cl)cc1] | MS: m/z Calcd 290.7 Found MH⁺ 291.0 |

Example 22

5-cyano-6-(isobutylamino)picolinic acid (70)

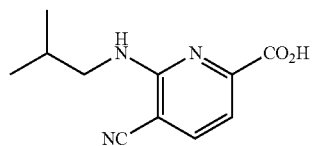 [SMILES: CC(C)CNc1nc(C(=O)O)ccc1C#N]

A mixture of 6-chloro-5-cyanopicolinic acid (30 mg, 0.16 mmol), isopropylamine (20 ul, 0.23 mmol), and KF (28 mg, 0.48 mmol) in N-methylpyrrolidinone (1 ml) was heated for 18 hrs at 95° C. The mixture was diluted with water (4 ml) and stranded overnight. The resulting precipitate was collected by filtration and dried under vacuum to afford 25 mg (75%) of the desired product 70. ¹H NMR (600 MHz, DMSO-d₆) δ 13.2 (s, 1H), 8.03 (d, 1H, J=7.8 Hz), 7.25-7.21 (m, 1H), 7.17 (d, 1H, J=7.8 Hz), 3.26-3.24 (m, 2H), 1.99-1.95 (m, 1H), 0.89 (d, 6H, 6.6 Hz). MS: m/z Calcd 219.2 Found MH⁺ 220.1

Compounds 64-80 were prepared by a similar procedure of Example 22.

| cpd | name | structure | analytical data |
|---|---|---|---|
| 64 | 5-cyano-6-(isopropylamino)picolinic acid | 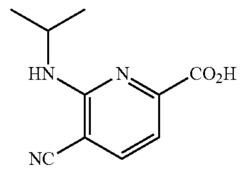 | MS: m/z Calcd 205.2 Found MH+ 206.0 |
| 65 | 5-cyano-6-(3-methoxypropylamino)picolinic acid | 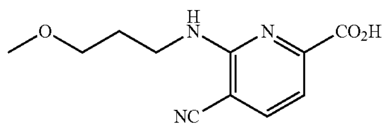 [SMILES: COCCCNc1nc(C(=O)O)ccc1C#N] | MS: m/z Calcd 235.2 Found MH+ 236.1 |
| 66 | 5-cyano-6-(diethylamino)picolinic acid | 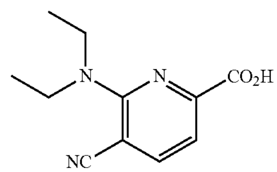 [SMILES: CCN(CC)c1nc(C(=O)O)ccc1C#N] | MS: m/z Calcd 219.2 Found MH+ 220.1 |
| 67 | 5-cyano-6-(4-(ethoxycarbonyl)piperidin-1-yl)picolinic acid | 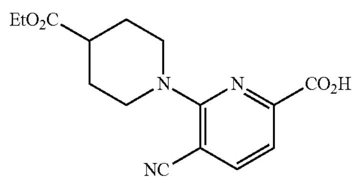 [SMILES: CCOC(=O)C1CCN(c2nc(C(=O)O)ccc2C#N)CC1] | MS: m/z Calcd 303.3 Found MH+ 304.1 |
| 68 | 5-cyano-6-(2-(ethoxycarbonyl)piperidin-1-yl)picolinic acid | 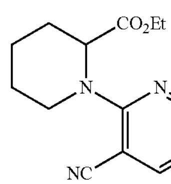 | MS: m/z Calcd 335.3 Found MH+ 304.1 |
| 69 | 5-cyano-6-(isopentylamino)picolinic acid | 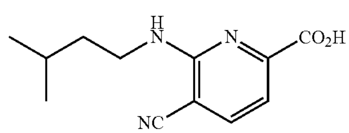 [SMILES: CC(C)CCNc1nc(C(=O)O)ccc1C#N] | MS: m/z Calcd 233.3 Found MH+ 234.1 |
| 71 | 5-cyano-6-(isopropylamino)picolinic acid | 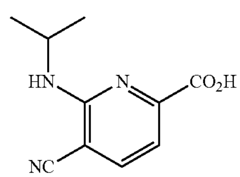 | MS: m/z Calcd 205.2 Found MH+ 206.1 |
| 72 | 5-cyano-6-(4-methylpiperazin-1-yl)picolinic acid | 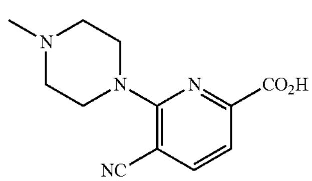 [SMILES: CN1CCN(c2nc(C(=O)O)ccc2C#N)CC1] | MS: m/z Calcd 246.3 Found MH+ 247.1 |
| 73 | 5-cyano-6-(2-methoxyethylamino)picolinic acid | 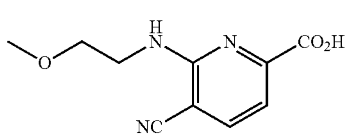 [SMILES: COCCNc1nc(C(=O)O)ccc1C#N] | MS: m/z Calcd 221.2 Found MH+ 222.1 |

-continued

| cpd | name | structure | analytical data |
|---|---|---|---|
| 74 | 5-cyano-6-(3-hydroxypropyl amino) picolinic acid | 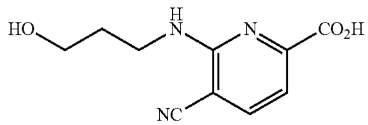 [SMILES: N#Cc1ccc(C(=O)O)nc1NCCCO] | $^1$H NMR (600MHz, DMSO-$d_6$) δ 13.3 (br s, 1H), 8.07 (d, 1H, J = 7.8 Hz), 7.34 (t, 1H, J = 6 Hz), 7.20 (d, 1H, J = 8.4 Hz), 4.60 (br s, 1H), 3.51-3.45 (m, 4H), 1.71 (quintet, 2H, J = 6.6 Hz). MS: m/z Calcd 221.2 Found MH$^+$ 222.10 |
| 75 | 5-cyano-6-morpholinopicolinic acid | 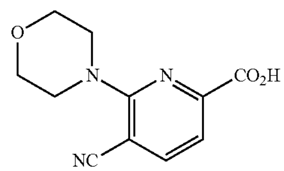 [SMILES: N#Cc1ccc(C(=O)O)nc1N1CCOCC1] | $^1$H NMR (600 MHz, DMSO-$d_6$) δ 13.4 (s, 1H), 8.24 (d, 1H, J = 7.8 Hz), 7.45 (d, 1H, J = 7.8 Hz), 3.74-3.67 (m, 4H). MS: m/z Calcd 233.2 Found MH$^+$ 234.1 |
| 76 | 5-cyano-6-(piperidin-1-yl)picolinic acid | 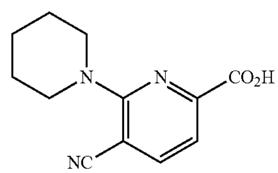 [SMILES: N#Cc1ccc(C(=O)O)nc1N1CCCCC1] | $^1$H NMR (600 MHz, DMSO-$d_6$) δ 13.4 (s, 1H), 8.17 (d, 1H, J = 7.8 Hz), 7.36 (d, 1H, J = 7.8 Hz), 3.69-3.66 (m, 4H), 2.51-2.48 (m, 6H). MS: m/z Calcd 231.3 Found MH$^+$ 232.1 |
| 77 | 5-cyano-6-(pyrrolidin-1-yl)picolinic acid | 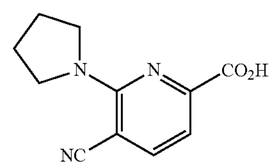 [SMILES: N#Cc1ccc(C(=O)O)nc1N1CCCC1] | $^1$H NMR (600 MHz, DMSO-$d_6$) δ 13.2 (s, 1H), 8.11-8.08 (m, 1H), 7.24-7.21 (m, 1H), 3.73-3.70 (m, 4H), 2.0-1.94 (m, 4H). MS: m/z Calcd 217.2 Found MH$^+$ 218.1 |
| 78 | 6-(benzylamino)-5-cyanopicolinic acid | 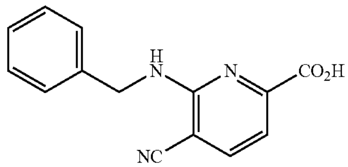 [SMILES: N#Cc1ccc(C(=O)O)nc1NCc1ccccc1] | $^1$H NMR (600 MHz, DMSO-$d_6$) δ 13.2 (s, 1H), 8.09 (d, 1H, 7.2 Hz), 7.96 (t, 1H, J = 5.4 Hz), 7.41 (d, 2H, J = 7.2 Hz), 7.31-7.21 (m, 4H), 4.64 (d, 2H, J = 6 Hz). MS: m/z Calcd 253.3 Found MH$^+$ 254.1 |
| 79 | 6-(benzyl(methyl)amino)-5-cyanopicolinic acid | 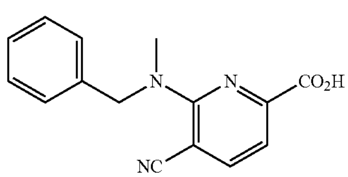 [SMILES: CN(Cc1ccccc1)c1nc(C(=O)O)ccc1C#N] | $^1$H NMR (600 MHz, DMSO-$d_6$) δ 13.4 (s, 1H), 8.16 (d, 1H, J = 7.8 Hz), 7.36-7.27 (m, 5H), 7.27-7.26 (m, 1H), 4.98 (s, 2H), 3.31 (s, 3H). MS: m/z Calcd 267.3 Found MH$^+$ 268.1 |

| cpd | name | structure | analytical data |
|---|---|---|---|
| 80 | 6-(4-chlorophenylamino)-5-cyanopicolinic acid | 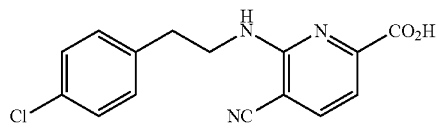 [SMILES: N#Cc1ccc(C(=O)O)nc1NCCc1ccc(Cl)cc1] | $^1$H NMR (600 MHz, DMSO-$d_6$) δ 13.3 (br s, 1H), 8.02 (d, 1H, J = 7.8 Hz), 7.43-7.40 (m, 1H), 7.38-7.20 (m, 5H), 3.61-3.59 (m, 2H), 2.84-2.82 (m, 2H). MS: m/z Calcd 301.7 Found MH$^+$ 302.0 |

Scheme 6

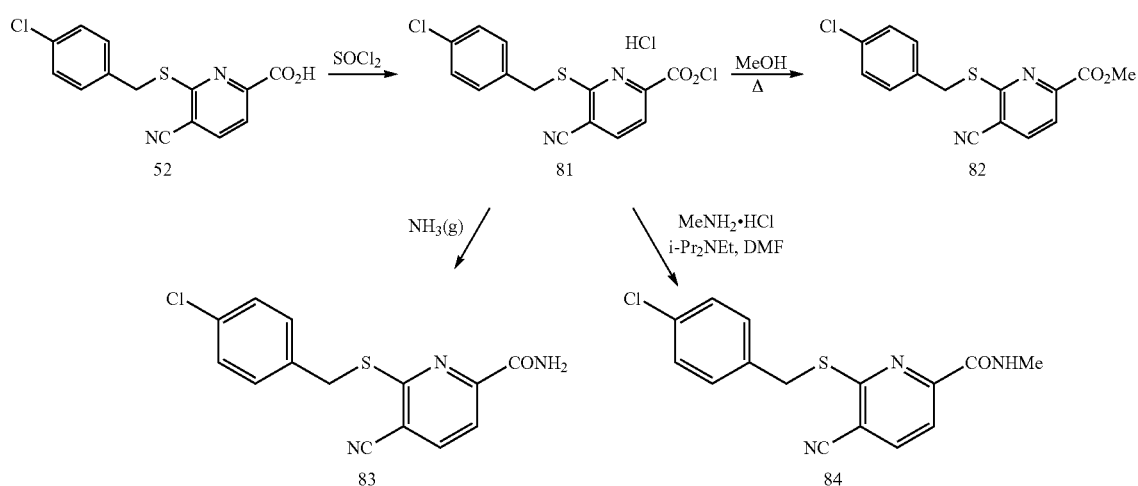

Example 23

Methyl 6-(4-chlorobenzylthio)-5-cyanopicolinate (82)

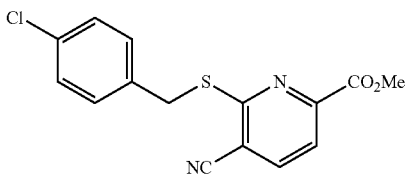 [SMILES: COC(=O)c1ccc(C#N)c(SCc2ccc(Cl)cc2)n1]

A mixture of 6-(4-chlorobenzylthio)-5-cyanopicolinic acid (100 mg, 0.33 mmol) and thionyl chloride (5 ml) was refluxed for 2 hrs. Thionyl chloride was evaporated under reduced pressure and the residue was dissolved in methanol (5 ml). After heating for 6 hrs at 40° C., the reaction mixture was concentrated in vacuo and purified by flash chromatography eluting with 25% ethyl acetate in hexane to afford 65 mg (62%) of the desired product 82. $^1$H NMR (600 MHz, DMSO-$d_6$) δ 8.42 (d, 1H, J=7.8 Hz), 7.89 (d, 1H, J=7.8 Hz), 7.59 (d, 2H, J=9 Hz), 7.35 (d, 2H, J=8.4 Hz), 4.55 (s, 2H), 3.98 (s, 3H). MS: m/z Calcd 318.8 Found MH$^+$ 319.0

Example 24

6-(4-chlorobenzylthio)-5-cyanopicolinamide (83)

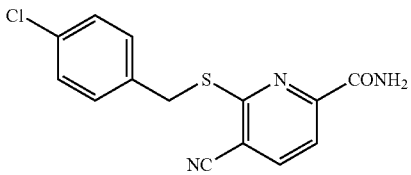 [SMILES: N#Cc1ccc(C(N)=O)nc1SCc1ccc(Cl)cc1]

Dry ammonia gas was bubbled through a solution of 6-(4-chlorobenzylthio)-5-cyanopicolinoyl chloride hydrochloride 81 (60 mg, 0.17 mmol) in dichloromethane (10 ml) for 5 min at 0° C. The mixture was stirred for 1 hr at ambient temperature and concentrated in vacuo. The crude product was purified by recrystallization in ether to afford 25 mg (48%) of the desired product 83. $^1$H NMR (600 MHz, DMSO-$d_6$) δ 8.37 (d, 1H, J=7.8 Hz), 7.84 (d, 1H, J=8.4 Hz), 7.49-7.47 (m, 2H), 7.38-7.37 (m, 2H), 4.74 (s, 2H). MS: m/z Calcd 303.8 Found MH$^+$ 304.0

Example 25

6-(4-chlorobenzylthio)-5-cyano-N-methylpicolinamide (84)

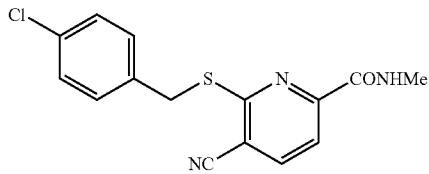

A mixture of 6-(4-chlorobenzylthio)-5-cyanopicolinoyl chloride hydrochloride 81 (60 mg, 0.17 mmol) and N,N-diisopropylethylamine (89 ul, 0.51 mmol) in dimethylformamide (2 ml) was stirred for 6 hrs at room temperature. After removal of the solvent, the residue was triturated with ether and the resulting solid was collected by filtration to afford 40 mg (74%) of the desired product 84. $^1$H NMR (600 MHz, DMSO-$d_5$) δ 8.79 (d, 1H, J=4.8 Hz), 8.37 (d, 1H, J=7.8 Hz), 7.84 (d, 1H, J=8.4 Hz), 7.49 (d, 2H, J=9 Hz), 7.38 (d, 2H, 9 Hz), 4.76 (s, 2H), 2.89 (d, 3H, J=4.8 Hz). MS: m/z Calcd 317.8 Found MH$^+$ 318.0

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

We claim:

1. A method for inhibiting activity of a type III secretion system of a bacterium, comprising contacting a bacterium having a type III secretion system with an effective amount of at least one compound selected from the formula:

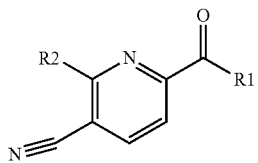

and a pharmaceutically acceptable salt thereof,
wherein:
R1 is selected from the group consisting of:
—O—(C1-C5)alkyl,
—NH—(C1-C5)alkyl,
—NH$_2$, and
—OH, and
R2 is

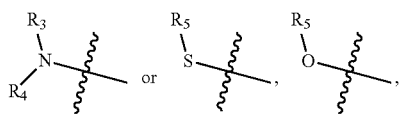

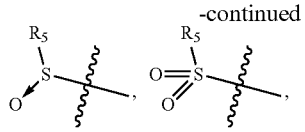

wherein:
R3 and R4 are joined as a five- or six-member heterocyclic ring that may be further substituted at any one position with —CO—O—(C1-C5)alkyl or (C1-C5)alkyl, or
R3 is —H or —(C1-C5)alkyl and
R4 is selected from the group consisting of:
—(C1-C5)alkyl,
—(C3-C8)cycloalkyl,
—(C1-C5)alkyl-O—(C1-C5)alkyl,
—(C1-C5)alkyl-hydroxyl,
-phenyl, and
—(C1-C5)alkyl-phenyl,
wherein the phenyl group may be independently substituted at one, two, or three positions with —(C1-C5)alkyl or -halogen, and
R5 is selected from the group consisting of:
—(C1-C5)alkyl,
—(C3-C8)cycloalkyl,
-phenyl, and
—(C1-C5)alkyl-phenyl,
wherein the phenyl group may be substituted at one, two, or three positions with a substituent independently selected from the group consisting of:
—(C1-C5)alkyl,
—O—(C1-C5)alkyl,
-halogen,
—NO$_2$,
—CF$_3$, and
—OCF$_3$.

2. The method of claim 1, wherein the at least one compound has a structure selected from the group consisting of:

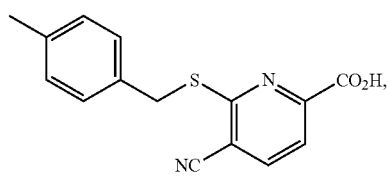

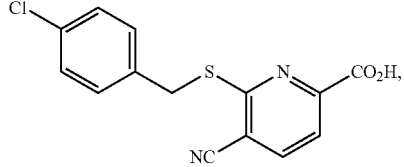

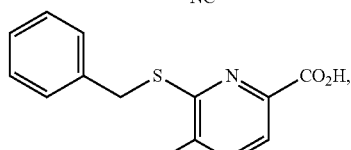

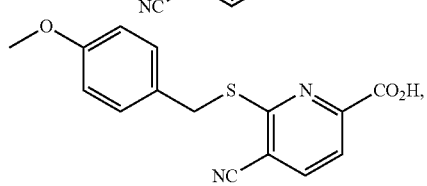

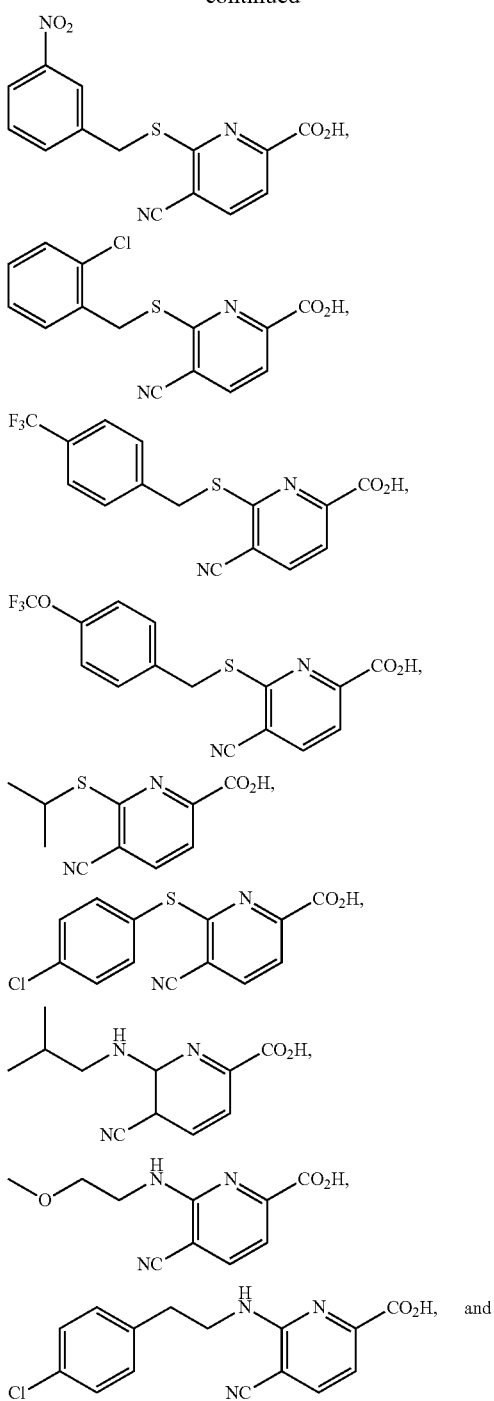

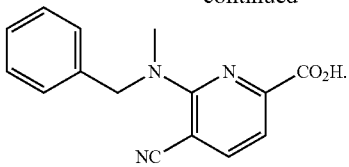

3. The method of claim 1, wherein the bacterium is a *Yersinia* species.

4. The method of claim 3, wherein the *Yersinia* species is *Yersinia pestis*, *Yersinia pseudotuberculosis*, or *Yersinia enterocolitica*.

5. The method of claim 1, wherein the bacterium is selected from the group consisting of: *Yersinia pestis*, *Yersinia enterocolitica*, *Yersinia pseudotuberculosis*, *Salmonella enterica*, *Escherichia coli*, *Shigella dysenteriae*, *Shigella flexneri*, *Shigella boydii*, *Shigella sonnei*, *Bordetella pertussis*, *Bordetella parapertussis*, *Bordetella bronchiseptica*, *Pseudomonas aeruginosa*, *Burkholderia pseudomallei*, *Vibrio parahaemolyticus*, *Vibrio cholerae*, *Chlamydia trachomatis*, *Chlamydia pneumoniae*, and *Chlamydia psittaci*.

6. The method of claim 1, wherein the bacterium is in a subject.

7. The method of claim 6, wherein the subject has a disease, or is at risk of a disease, caused by the bacterium.

8. The method of claim 7, wherein the disease is selected from the group consisting of: bubonic plague, pneumonic plague, septicemic plague, enterocolitis, mesenteric lymphadenitis, typhlitis, typhoid-like disease, enteric fever, intestinal inflammation, bacteremia, septicemia, bloody diarrhea, renal failure, septic shock, bacillary dysentery (shigellosis), sporadic dysentery, whooping cough, kennel cough, atrophic rhinitis, respiratory illness, pneumonia, chronic airway infection, urinary tract infection, clinical infections, melioidosis, noninflammatory secretory diarrhea, inflammatory diarrhea, sexually transmitted infection, and psittacosis.

9. The method of claim 6, wherein the subject is a human.

10. The method of claim 1, wherein the bacterium is a biowarfare agent.

11. The method of claim 1, wherein if R1 is —OH, then R5 is not

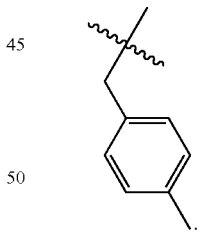

\* \* \* \* \*